US012644139B2

(12) United States Patent
Pfleger et al.

(10) Patent No.: US 12,644,139 B2
(45) Date of Patent: Jun. 2, 2026

(54) CELLS AND METHODS FOR PRODUCING METHYL KETONES

(71) Applicant: Wisconsin Alumni Research Foundation, Madison, WI (US)

(72) Inventors: Brian F. Pfleger, Madison, WI (US); Qiang Yan, Madison, WI (US); Trevor R. Simmons, Austin, TX (US); Nestor Hernandez-Lozada, Jena (DE)

(73) Assignee: Wisconsin Alumni Research Foundation, Madison, WI (US)

( * ) Notice: Subject to any disclaimer, the term of this patent is extended or adjusted under 35 U.S.C. 154(b) by 664 days.

(21) Appl. No.: 17/926,487

(22) PCT Filed: May 20, 2021

(86) PCT No.: PCT/US2021/033382
§ 371 (c)(1),
(2) Date: Nov. 18, 2022

(87) PCT Pub. No.: WO2021/236919
PCT Pub. Date: Nov. 25, 2021

(65) Prior Publication Data
US 2023/0183759 A1       Jun. 15, 2023

Related U.S. Application Data

(60) Provisional application No. 63/027,872, filed on May 20, 2020.

(51) Int. Cl.
| | |
|---|---|
| *C12P 7/26* | (2006.01) |
| *C12N 9/00* | (2006.01) |
| *C12N 9/04* | (2006.01) |
| *C12N 9/16* | (2006.01) |
| *C12N 15/52* | (2006.01) |
| *C12N 15/74* | (2006.01) |

(52) U.S. Cl.
CPC .............. *C12P 7/26* (2013.01); *C12N 9/0006* (2013.01); *C12N 9/16* (2013.01); *C12N 9/93* (2013.01); *C12N 15/52* (2013.01); *C12N 15/74* (2013.01); *C12N 2330/50* (2013.01); *C12Y 101/01035* (2013.01); *C12Y 301/0202* (2013.01); *C12Y 301/02021* (2013.01); *C12Y 402/01017* (2013.01); *C12Y 602/01001* (2013.01)

(58) Field of Classification Search
None
See application file for complete search history.

(56) References Cited

U.S. PATENT DOCUMENTS

| | | |
|---|---|---|
| 4,837,148 A | 6/1989 | Cregg |
| 4,929,555 A | 5/1990 | Cregg |
| 5,077,214 A | 12/1991 | Guarino |

| | | |
|---|---|---|
| 5,679,543 A | 10/1997 | Lawlis |
| 7,786,355 B2 | 8/2010 | Aquin |
| 10,421,951 B2 | 9/2019 | Pfleger |
| 10,844,410 B2 | 11/2020 | Pfleger |
| 2011/0165637 A1 | 7/2011 | Pfleger |
| 2014/0073022 A1 | 3/2014 | Pfleger et al. |
| 2014/0370560 A1* | 12/2014 | Beller ....................... C12P 7/26 |
| | | 435/252.33 |
| 2019/0284588 A1 | 9/2019 | Pfleger et al. |

FOREIGN PATENT DOCUMENTS

| | | |
|---|---|---|
| EP | 238 023 A2 | 9/1987 |
| EP | 2771381 A1 | 9/2014 |
| WO | WO 96/00787 A1 | 1/1996 |

OTHER PUBLICATIONS

Uniprot, Accession No. K8WBA2, Feb. 2020, www.uniprot.org. (Year: 2020).*
Yan et al., Metabolic engineering of β-oxidation to leverage thioesterases for production of 2-heptanone, 2-nonanone and 2-undecanone, Metabolic Eng. 61, May 29, 2020, 335-43 (Year: 2020).*
Genbank, Accession No. WP_008916720.1, 2017, ncbi.nlm.nih.gov. (Year: 2017).*
DiRusso et al., Characterization of FadR, a Global Transcriptional Regulator of Fatty Acid Metabolism in *Escherichia coli*, J. Biol. Chem. 267, 1992, 8685-91. (Year: 1992).*
International Preliminary Report on Patentability dated Dec. 1, 2022, for PCT application PCT/US2021/033382.
International Search Report and Written Opinion dated Sep. 22, 2021, for PCT application PCT/US2021/033382.
Agnew, D.E., Stevermer, A.K., Youngquist, J.T., Pfleger, B.F., 2012. Engineering *Escherichia coli* for production of C12-C14 polyhydroxyalkanoate from glucose. Metab. Eng. 14, 705-713.
Altschul et al., Basic local alignment search tool, *J. Mol. Biol.* 215:403-410 (1990).
Beach et al. Functionally homologous cell cycle control genes in budding and fission yeast, (1981) *Nature* 300:706.
Beller, Harry R., et al. "Natural products as biofuels and bio-based chemicals: fatty acids and isoprenoids," Natural Product Reports, vol. 32, No. 10. 2015. 1508-1526.
Benoist et al. In vivo sequence requirements of the SV40 early promotor region, (1981) Nature (London) 290:304.
Bitter et al. Expression and secretion vectors for yeast, (1987) *Methods in Enzymology*, 153:516-544).
Black et al. Cloning, sequencing, and expression of the fadD gene of *Escherichia coli* encoding acyl coenzyme A synthetase, 1992, *J. Biol. Chem.* 267:25513-25520.

(Continued)

*Primary Examiner* — Todd M Epstein
(74) *Attorney, Agent, or Firm* — Daniel A. Blasiole; DeWitt LLP

(57) ABSTRACT

Recombinant cells and methods for producing methyl ketones, such as medium-chain methyl ketones. The recombinant cells include recombinant acyl-ACP thioesterase genes, recombinant β-ketoacyl-CoA thioesterase genes, and recombinant acyl-CoA synthetase genes, in addition to other modifications. The methods include culturing the recombinant cells to produce the methyl ketones and isolating the produced methyl ketones.

11 Claims, 31 Drawing Sheets

Specification includes a Sequence Listing.

(56)            References Cited

OTHER PUBLICATIONS

Cantu, D.C., Chen, Y., Lemons, M.L., Reilly, P.J., 2011. ThYme: a database for thioester-active enzymes. Nucleic Acids Res. 39, D342-D346.

Chakrabarty, A.M., Chou, G., Gunsalus, I.C., 1973. Genetic Regulation of Octane Dissimilation Plasmid in *Pseudomonas*. Proc. Natl. Acad. Sci. 70, 1137-1140.

Chang and Cohen. High frequency transformation of Bacillus subtilis protoplasts by plasmid DNA, (1979) *Molecular General Genetics*, 168:111-115.

Clomburg, J.M., Vick, J.E., Blankschien, M.D., Rodríguez-Moyá, M., Gonzalez, R., 2012. A Synthetic Biology Approach to Engineer a Functional Reversal of the β-Oxidation Cycle. ACS Synth. Biol. 1, 541-554.

Collins, Y.F., McSweeney, P.L.H., Wilkinson, M.G., 2003. Lipolysis and free fatty acid catabolismin cheese: a review of current knowledge. Int. Dairy J. 13, 841-866.

Cregg et al. Pichia pastoris as a host system for transformations, (1985) *Mol. Cell. Biol.* 5:3376.

Das et al. Transformation of Kluyveromyces fragilis, (1984) *J. Bacteriol.* 158:1165.

Davidow et al. (1985) *Curr. Genet.* 10:380-471.

Dellomonaco, C., Clomburg, J.M., Miller, E.N., Gonzalez, R., 2011. Engineered reversal of the β-oxidation cycle for the synthesis of fuels and chemicals. Nature 476, 355-359.

De Louvencourt et al. Transformation of Kluyveromyces lactis by killer plasmid DNA, (1983) *J. Bacteriol.* 154:737.

Dong, J., Chen, Y., Benites, V.T., Baidoo, E.E.K., Petzold, C.J., Beller, H.R., Eudes, A., Scheller, H. V., Adams, P.D., Mukhopadhyay, A., Simmons, B.A., Singer, S.W., 2019. Methyl ketone production by *Pseudomonas putida* is enhanced by plant-derived amino acids. Biotechnol. Bioeng. 116, 1909-1922.

Dubnau and Davidoff-Abelson. Fate of transforming DNA following uptake by competent Bacillus subtilis. I. Formation and properties of the donor-recipient complex, (1971) *Journal of Molecular Biology*, 56: 209-221.

Dyrløv Bendtsen, J., Nielsen, H., von Heijne, G., Brunak, S., 2004. Improved Prediction of Signal Peptides: SignalP 3.0. J. Mol. Biol. 340, 783-795.

Foecking et al. Powerful and versatile enhancer-promoter unit for mammalian expression vectors, (1980) Gene 45:101).

Forney, F., Markovetz, A., 1971. The biology of methyl ketones. J. Lipid Res. 12, 383-395.

Frias, J.A., Richman, J.E., Erickson, U.S., Wackett, L.P., 2011. Purification and Characterization of OleA from Xanthomonas campestris and Demonstration of a Non-decarboxylative Claisen Condensation Reaction. J. Biol. Chem. 286, 10930-10938.

Gaillardin et al. (1985) *Curr. Genet.* 10:49.

Ganeva et al. Influence of glucose and other substrates on electric field and polyethylene glycol-mediated transformation of intact yeast cells, (1994) *FEMS Microbiology Letters* 121:159-64.

Gibson, D.G., Young, L., Chuang, R.-Y., Venter, J.C., Hutchison, C.A., Smith, H.O., 2009. Enzymatic assembly of DNA molecules up to several hundred kilobases. Nat. Methods 6, 343-345.

Gleeson et al. Transformation of the Methylotrophic Yeast *Hansenula polymorpha*, (1986) *J. Gen. Microbiol.* 132:3459.

Glick and Whiteney. Factors affecting the expression of foreign proteins n *Escherichia coli, J. Ind. Microbiol.* 1:277 (1987).

Goh, E.-B., Baidoo, E.E.K., Keasling, J.D., Beller, H.R., 2012. Engineering of Bacterial Methyl Ketone Synthesis for Biofuels. Appl. Environ. Microbiol. 78, 70-80.

Goh, E.-B., Baidoo, E.E.K., Burd, H., Lee, T.S., Keasling, J.D., Beller, H.R., 2014. Substantial improvements in methyl ketone production in *E. coli* and insights on the pathway from in vitro studies. Metab. Eng. 26, 67-76.

Goh, E.-B., Chen, Y., Petzold, C.J., Keasling, J.D., Beller, H.R., 2018. Improving methyl ketone production in *Escherichia coli* by heterologous expression of NADH-dependent FabG. Biotechnol. Bioeng. 115, 1161-1172.

Grisewood, M.J., Hernández-Lozada, N.J., Thoden, J.B., Gifford, N.P., Mendez-Perez, D., Schoenberger, H.A., Allan, M.F., Floy, M.E., Lai, R.-Y., Holden, H.M., Pfleger, B.F., Maranas, C.D., 2017. Computational Redesign of Acyl-ACP Thioesterase with Improved Selectivity toward Medium-Chain-Length Fatty Acids. ACS Catal. 7, 3837-3849.

Hamer et al. Regulation in vivo of a cloned mammalian gene: cadmium induces the transcription of a mouse metallothionein gene in SV40 vectors, (1982) *J. Mol. Appl. Gen.* 1:273).

Hanko, E.K.R., Denby, C.M., Sànchez i Nogué, V., Lin, W., Ramirez, K.J., Singer, C.A., Beckham, G.T., Keasling, J.D., 2018. Engineering β-oxidation in *Yarrowia lipolytica* for methyl ketone production. Metab. Eng. 48, 52-62.

Harrison, K.W., Harvey, B.G., 2018. High cetane renewable diesel fuels prepared from bio-based methyl ketones and diols. Sustain. Energy Fuels 2, 367-371.

Henikoff & Henikoff. Amino acid substitution matrices from protein blocks, (1989) Proc. Natl. Acad. Sci. USA 89:10915).

Hernández Lozada, N.J., Lai, R.-Y., Simmons, T.R., Thomas, K.A., Chowdhury, R., Maranas, C.D., Pfleger, B.F., 2018. Highly Active $C_8$-Acyl-ACP Thioesterase Variant Isolated by a Synthetic Selection Strategy. ACS Synth. Biol. 7, 2205-2215.

Hernández Lozada, N.J., Simmons, T.R., Xu, K., Jindra, M.A., Pfleger, B.F., 2020. Production of 1-octanol in *Escherichia coli* by a high flux thioesterase route. doi: Under review.

Hinnen et al. Transformation of yeast, (1978) *Proc. Natl. Acad. Sci.* USA 75:1929.

Hoekman, S.K., Broch, A., Robbins, C., Ceniceros, E., Natarajan, M., 2012. Review of biodiesel composition, properties, and specifications. Renew. Sustain. Energy Rev. 16, 143-169.

Hoffmann, N., Rehm, B.H .., 2004. Regulation of polyhydroxyalkanoate biosynthesis in *Pseudomonas putida* and *Pseudomonas aeruginosa*. FEMS Microbiol. Lett. 237, 1-7.

Hoffmann, N., Rehm, B.H.A., 2005. Nitrogen-dependent regulation of medium-chain length polyhydroxyalkanoate biosynthesis genes in pseudomonads. Biotechnol. Lett. 27, 279-282.

Ito et al. Transformation of intact yeast cells treated with alkali cations, (1983) *J. Bacteriol.* 153:163.

Iram, S.H., Cronan, J.E., 2006. The β-Oxidation Systems of *Escherichia coli* and *Salmonella enterica* Are Not Functionally Equivalent. J. Bacteriol. 188, 599-608.

Jeon, E. et al. Development of *Escherichia coli* MG1655 strains to produce long chain fatty acids by engineering fatty acid synthesis (FAS) metabolism, (2011) *Enzyme Microb. Technol.* 49, 44-51.

Johnston et al. Isolation of the yeast regulatory gene GAL4 and analysis of its dosage effects on the galactose/melibiose regulon, (1982) *PNAS (USA)* 79:6971.

Karlin & Altschul, Applications and statistics for multiple high-scoring segments in molecular sequences, .Proc. Natl. Acad. Sci. USA 90:5873-5787 (1993).

Kennedy, G.G., 2003. Tomato, pests, parasitoids, and predators: tritrophic interactions involving the genus Lycopersicon. Annu. Rev. Entomol. 48, 51-72.

Koehler and Thorne. Bacillus subtilis (natto) plasmid pLS20 mediates interspecies plasmid transfer, (1987) *Journal of Bacteriology*, 169:5771-5278.

Kornberg, A., Ochoa, S., Mehler, A.H., 1948. Spectrophotometric studies on the decarboxylation of β-keto acids. J. Biol. Chem. 174, 159.

Kim, E.-J., Son, H.F., Kim, S., Ahn, J.-W., Kim, K.-J., 2014. Crystal structure and biochemical characterization of beta-keto thiolase B from polyhydroxyalkanoate-producing bacterium *Ralstonia eutropha* H16. Biochem. Biophys. Res. Commun. 444, 365-369.

Kunze et al. Transformation of the industrially important yeasts *Candida maltosa* and *Pichia guilliermondii*, (1985) *J. Basic Microbiol.* 25:141.

Kurtz, et al. Integrative transformation of Candida albicans, using a cloned Candida ADE2 gene, (1986) *Mol. Cell. Biol.* 6:142.

Kutralam-Muniasamy, Gurusamy, et al. "Genome characteristics dictate poly-R-(3)-hydroxyalkanoate production inCupriavidus necatorH16," World Journal of Microbiology & Biotechnology, Rapid Communications of Oxford, vol. 34, No. 6. 2018. 1-23.

(56)　　　　　References Cited

OTHER PUBLICATIONS

Lan, E.I., Dekishima, Y., Chuang, D.S., Liao, J.C., 2013. Metabolic engineering of 2-pentanone synthesis in *Escherichia coli*. AIChE J. 59, 3167-3175.

Lennen, R.M., Braden, D.J., West, R.M., Dumesic, J.A., Pfleger, B.F., 2010. A process for microbial hydrocarbon synthesis: Overproduction of fatty acids in *Escherichia coli* and catalytic conversion to alkanes. Biotechnol. Bioeng. 106, 193-202.

Lennen, R.M. et al. Membrane stresses induced by overproduction of free fatty acids in *Escherichia coli*, (2011) *Appl. Environ. Microbiol.* 77, 8114-8128.

Lennen et al. Engineering *Escherichia coli* to synthesize free fatty acids, (2012) *Trends in Biotechnology* 30(12), 659-667.

Li, M. et al. Effect of acetate formation pathway and long chain fatty acid CoA-ligase on the free fatty acid production in *E. coli* expressing acy-ACP thioesterase from Ricinus communis, (2012) *Metab. Eng.* 14, 380-387.

Lian, J., Zhao, H., 2015. Reversal of the β-Oxidation Cycle in *Saccharomyces cerevisiae* for Production of Fuels and Chemicals. ACS Synth. Biol. 4, 332-341.

Liu, T. et al. Quantitative analysis and engineering of fatty acid biosynthesis in *E. coli*, (2010) *Metab. Eng.* 12, 378-386.

Liu, H. et al. Production of extracellular fatty acid using engineered *Escherichia coli*, (2012) *Microb. Cell Fact.* 11, 41.

Lu, X. et al. Overproduction of free fatty acids in *E. coli*: implications for biodiesel production, (2008) *Metab. Eng.* 10, 333-339.

Malardier et al., Cloning of the nitrate reductase gene (niaD) of Aspergillus nidulans and its use for transformation of Fusarium oxysporum, *Gene*, 1989, 78:147-56.

Manivasakam and Schiestl. High efficiency transformation of *Saccharomyces cerevisiae* by electroporation, (1993) *Nucleic Acids Research* 21(18):4414-5.

Matesanz et al. The cloning and expression of Pfacs1, a Plasmodium falciparum fatty acyl coenzyme A synthetase-1 targeted to the host erythrocyte cytoplasm, 1999, *J. Mol. Biol.* 291:59-70.

McKnight. Functional relationships between transcriptional control signals of the thymidine kinase gene of herpes simplex virus, (1982) *Cell* 31:355.

Mehrer, C.R., Incha, M.R., Politz, M.C., Pfleger, B.F., 2018. Anaerobic production of medium-chain fatty alcohols via a β-reduction pathway. Metab. Eng. 48, 63-71.

Mehrer, C.R., Rand, J.M., Incha, M.R., Cook, T.B., Demir, B., Motagamwala, A.H., Kim, D., Dumesic, J.A., Pfleger, B.F., 2019. Growth-coupled bioconversion of levulinic acid to butanone. Metab. Eng. 55, 92-101.

Muller, J., MacEachran, D., Burd, H., Sathitsuksanoh, N., Bi, C., Yeh, Y.-C., Lee, T.S., Hillson, N.J., Chhabra, S.R., Singer, S.W., Beller, H.R., 2013. Engineering of *Ralstonia eutropha* H16 for Autotrophic and Heterotrophic Production of Methyl Ketones. Appl. Environ. Microbiol. 79, 4433-4439.

Needleman & Wunsch, A general method applicable to the search for similarities in the amino acid sequence of two proteins, J. Mol. Biol. 48:443 (1970).

Nie, L., Ren, Y., Schulz, H., 2008. Identification and Characterization of *Escherichia coli* Thioesterase III That Functions in Fatty Acid β-Oxidation. Biochemistry 47, 7744-7751.

Orlandi et al. Cloning immunoglobulin variable domains for expression by the polymerase chain reaction, (1989) *PNAS* (USA) 86:3833.

Park, J., Rodríguez-Moyá, M., Li, M., Pichersky, E., San, K.-Y., Gonzalez, R., 2012. Synthesis of methyl ketones by metabolically engineered *Escherichia coli*. J. Ind. Microbiol. Biotechnol. 39, 1703-1712.

Pearson & Lipman, Improved tools for biological sequence comparison, Proc. Nat'l. Acad. Sci. USA 85:2444 (1988).

Reeves et al. Multiple transformation of *Saccaromyces cerevisiae* by protoplast fusion, (1992) *FEMS Microbiology Letters* 99:193-198.

Roggenkamp et al. Transformation of the methylotrophic yeast Hansenula polymorpha by autonomous replication and integration vectors, (1986) *Mol. Gen. Genet.* 202:302.

Silver et al. Amino terminus of the yeast GAL4 gene product is sufficient for nuclear localization, (1984) *PNAS* (USA) 81:5951.

Smith & Waterman, Comparison of Biosequences, Adv. Appl. Math. 2:482 (1981).

Srirangan, K., Liu, X., Akawi, L., Bruder, M., Moo-Young, M., Chou, C.P., 2016. Engineering *Escherichia coli* for Microbial Production of Butanone. Appl. Environ. Microbiol. 82, 2574-2584.

Steen, E.J. et al. Microbial production of fatty-acid-derived fuels and chemicals from plant biomass, (2010) *Nature* 463, 559-562.

Van Beilen et al. DNA sequence determination and functional characterization of the OCT-plasmid-encoded alkJKL genes of Pseudomonas oleovorans, 1992, *Molecular Microbiology* 6:3121-3136.

Van den Berg et al. Kluyveromyces as a host for heterologous gene expression: expression and secretion of prochymosin, (1990) Bio/Technology 8:135.

Voelker, T.A., Davies, H.M., 1994. Alteration of the specificity and regulation of fatty acid synthesis of *Escherichia coli* by expression of a plant medium-chain acyl-acyl carrier protein thioesterase. J. Bacteriol. 176, 7320-7327.

Wang, F., Langley, R., Gulten, G., Wang, L., Sacchettini, J.C. 2007. Identification of a type III thioesterase reveals the function of an operon crucial for Mtb virulence. Chem. Biol. 14, 543-551.

Yan, Q., Pfleger, B.F., 2019. Revisiting metabolic engineering strategies for microbial synthesis of oleochemicals. Metab. Eng. 58:35-46.

Young and Spizizen. Physiological and genetic factors affecting transformation of Bacillus subtilis, (1961) *Journal of Bacteriology*, 81:823-829.

Youngquist, J.T., Schumacher, M.H., Rose, J.P., Raines, T.C., Politz, M.C., Copeland, M.F., Pfleger, B.F., 2013. Production of medium chain length fatty alcohols from glucose in *Escherichia coli*. Metab. Eng. 20, 177-186.

Youngquist, J.T et al. Kinetic modeling of free fatty acid production in *Escherichia coli* based on continuous cultivation of a plasmid free strain, (2012) *Biotechnol. Bioeng.* 109, 1518-1527.

Yu, Ai-Qun, et al. "Production of Fatty Acid-Derived Valuable Chemicals in Synthetic Microbes," Frontiers in Bioenginerring and Biotechnology, vol. 2, 2014.

Yu, G., Nguyen, T.T.H., Guo, Y., Schauvinhold, I., Auldridge, M.E., Bhuiyan, N., Ben-Israel, I., Iijima, Y., Fridman, E., Noel, J.P., Pichersky, E., 2010. Enzymatic Functions of Wild Tomato Methyl ketone Synthases 1 and 2. Plant Physiol. 154, 67-77.

Yu, X et al. In vitro reconstitution and steady-state analysis of the fatty acid synthase from *Escherichia coli*, (2011) *Proc. Natl. Acad. Sci. U.S.A.* 108, 18643-18648.

Yuzawa, S., Deng, K., Wang, G., Baidoo, E.E.K., Northen, T.R., Adams, P.D., Katz, L., Keasling, J.D., 2017. Comprehensive in Vitro Analysis of Acyltransferase Domain Exchanges in Modular Polyketide Synthases and Its Application for Short-Chain Ketone Production. ACS Synth. Biol. 6, 139-147.

Yuzawa, S., Mirsiaghi, M., Jocic, R., Fujii, T., Masson, F., Benites, V.T., Baidoo, E.E.K., Sundstrom, E., Tanjore, D., Pray, T.R., George, A., Davis, R.W., Gladden, J.M., Simmons, B.A., Katz, L., Keasling, J.D., 2018. Short-chain ketone production by engineered polyketide synthases in *Streptomyces albus*. Nat. Commun. 9, 4569.

Zhang, F. et al. Design of a dynamic sensor-regulator system for production of chemicals and fuels derived from fatty acids, (2012) *Nat. Biotechnol.* 30, 354-359.

Zhang, X. et al. Efficient free fatty acid production in *Escherichia coli* using plant acyl-ACP thioesterases, (2011) *Metab. Eng.* 13, 713-722.

Zhang, X. et al. Improving fatty acid production in *Escherichia coli* through the overexpression of malonyl coA-acyl carrier protein transacylase, (2012) *Biotechnol. Prog.* 28, 60-65.

Zhu, M., Xu, X., Li, Y., Wang, P., Niu, S., Zhang, K., Huang, X., 2019. Biosynthesis of the Nematode Attractant 2-Heptanone and Its Co-evolution Between the Pathogenic Bacterium *Bacillus nematocida* and Non-pathogenic Bacterium *Bacillus subtilis*. Front. Microbiol. 10.

Zhu, J., Dhammi, A., van Kretschmar, J.B., Vargo, E.L., Apperson, C.S., Michael Roe, R., 2018. Novel use of aliphatic n-methyl

(56) References Cited

OTHER PUBLICATIONS ketones as a fumigant and alternative to methyl bromide for insect control. Pest Manag. Sci. 74, 648-657.

Zhu, Z., Zhou, Y.J., Krivoruchko, A., Grininger, M., Zhao, Z.K., Nielsen, J., 2017. Expanding the product portfolio of fungal type I fatty acid synthases. Nat. Chem. Biol. 13, 360-362.

\* cited by examiner

1  Escherichia coli (Ec) / Salmonella enterica (Se)
2  Beauveriabassiana(Ba)
3  Buttiauxellaagrestis(Ba)
4  Neisseria gonorrhoeae (Ng)
5  Providenciasneebia(Ps)
6  Serratia odorifera (So)
7  Marinomonas ushuaiensis (Mu)
8  Mycobacterium tuberculosis (Mt1~ Mt5)
9  Cronobacter turicensis (Ct)
10  Enterobactercloacae(Eel)
11  Pseudomonasaeruginosa(Pa)

| | | EcFadM | SeFadM | CsFadM | CtFadM | BbFadM | BaFadM | SoFadM | MtFadM1 | PsFadM | NgFadM | MuFadM | MtFadM2 | PaFadM | MtFadM3 | MtFadM4 | MtFadM5 |
|---|---|---|---|---|---|---|---|---|---|---|---|---|---|---|---|---|---|
| Escherichia coli | EcFadM | 100 | 95 | 91 | 87 | 82 | 82 | 76 | 58 | 48 | 41 | 39 | 31 | 30 | 26 | 24 | 24 |
| Salmonella enterica | SeFadM | 95 | 100 | 93 | 88 | 80 | 79 | 77 | 58 | 50 | 45 | 45 | 35 | 38 | 30 | 28 | 28 |
| Cucumis sativus | CsFadM | 91 | 93 | 100 | 88 | 82 | 82 | 77 | 57 | 48 | 43 | 42 | 33 | 32 | 28 | 24 | 25 |
| Cranobacter turicensis | CtFadM | 87 | 88 | 88 | 100 | 78 | 80 | 76 | 57 | 51 | 41 | 41 | 31 | 31 | 25 | 26 | 24 |
| Beauveria bassiana | BbFadM | 82 | 80 | 82 | 78 | 100 | 94 | 80 | 55 | 44 | 43 | 38 | 29 | 32 | 27 | 24 | 24 |
| Butbiauxella agrestis | BaFadM | 82 | 79 | 82 | 80 | 94 | 100 | 77 | 53 | 46 | 41 | 38 | 30 | 34 | 26 | 24 | 25 |
| Serratia odorifera | SoFadM | 76 | 77 | 77 | 76 | 80 | 77 | 100 | 55 | 49 | 41 | 39 | 26 | 31 | 26 | 23 | 25 |
| Mycobacterium tuberculosis | MtFadM1 | 58 | 58 | 57 | 57 | 55 | 53 | 55 | 100 | 45 | 33 | 37 | 34 | 33 | 35 | 44 | 44 |
| Providencia sneebie | PsFadM | 48 | 50 | 48 | 51 | 44 | 46 | 49 | 45 | 100 | 36 | 36 | 26 | 30 | 34 | 36 | 35 |
| Neisseria gonorrhoeae | NgFadM | 41 | 45 | 43 | 41 | 43 | 41 | 41 | 33 | 36 | 100 | 40 | 26 | 26 | 33 | 36 | 37 |
| Marinomonas ushuaiensis | MuFadM | 39 | 45 | 42 | 41 | 38 | 38 | 39 | 37 | 36 | 40 | 100 | 28 | 30 | 37 | 36 | 30 |
| Mycobacterium tuberculosis | MtFadM2 | 31 | 35 | 33 | 31 | 29 | 30 | 26 | 25 | 26 | 30 | 28 | 100 | 25 | 25 | 24 | 36 |
| Pseudomonas aeruginosa | PaFadM | 30 | 38 | 32 | 31 | 32 | 34 | 31 | 33 | 30 | 26 | 30 | 25 | 100 | 28 | 25 | 36 |
| Mycobacterium tuberculosis | MtFadM3 | 26 | 30 | 28 | 25 | 27 | 28 | 26 | 26 | 34 | 33 | 37 | 25 | 28 | 100 | 74 | 70 |
| Mycobacterium tuberculosis | MtFadM4 | 24 | 28 | 24 | 26 | 24 | 24 | 23 | 44 | 36 | 36 | 36 | 24 | 25 | 74 | 100 | 84 |
| Mycobacterium tuberculosis | MtFadM5 | 24 | 28 | 25 | 24 | 24 | 25 | 25 | 44 | 35 | 37 | 30 | 36 | 36 | 70 | 84 | 100 |

FIG. 2B

A. Schematic of Bioprospecting Assay

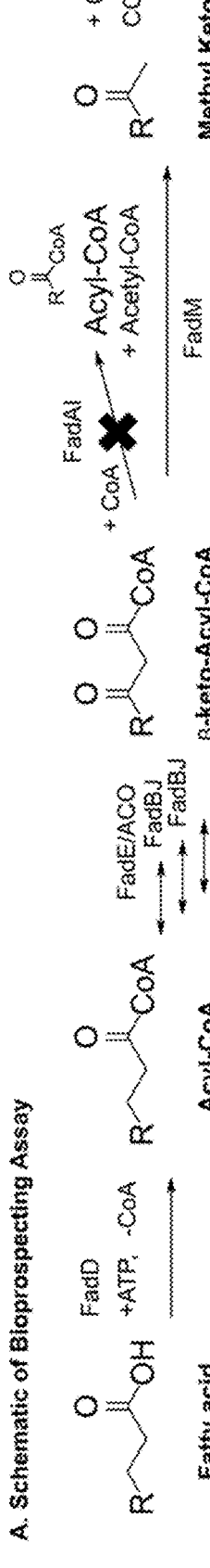

Fatty acid → (FadD, +ATP, –CoA) → Acyl-CoA → (FadE/ACO, FadBJ, FadBJ) → β-keto-Acyl-CoA → (FadAi ✕ +CoA) ... FadM → Acyl-CoA + Acetyl-CoA → Methyl Ketone (+CoA, CO2)

B. Evaluation of FadM Homologs

| | C7 MK Titer (mg/L) | C8 FFA Consump. (mg/L/h) | C9 MK Titer (mg/L) | C10 FFA Consump. (mg/L/h) | C11 MK Titer (mg/L) | C12 FFA Consump. (mg/L/h) | C13 MK Titer (mg/L) | C14 FFA Consump. (mg/L/h) | C15 MK Titer (mg/L) | C16 FFA Consump. (mg/L/h) |
|---|---|---|---|---|---|---|---|---|---|---|
| Control | 0.4 ± 0.1 | 14.5 ± 2.7 | 2.3 ± 0.1 | 2.1 ± 0.4 | 0.5 ± 0.0 | 2.3 ± 0.2 | 7.4 ± 1.2 | 6.8 ± 1.5 | 1.2 ± 0.8 | 3.5 ± 0.2 |
| SeFadM | 4.7 ± 0.7 | 18.1 ± 3.5 | 10.9 ± 0.6 | 3.9 ± 0.4 | 16.0 ± 2.3 | 9.7 ± 0.6 | 22.3 ± 2.7 | 17.5 ± 0.9 | 36.2 ± 4.7 | 6.0 ± 1.0 |
| NgFadM | 4.9 ± 0.5 | 5.2 ± 3.4 | 8.1 ± 0.4 | 6.0 ± 0.3 | 22.8 ± 1.5 | 13.7 ± 0.9 | 18.5 ± 2.5 | 15.4 ± 3.8 | 22.0 ± 10.1 | 7.6 ± 1.0 |
| MtFadM5 | 5.3 ± 0.3 | 5.2 ± 2.9 | 10.0 ± 0.4 | 5.3 ± 0.2 | 27.7 ± 0.1 | 12.9 ± 1.0 | 22.9 ± 1.7 | 17.4 ± 0.5 | 35.1 ± 1.6 | 6.2 ± 1.8 |
| MuFadM | 5.6 ± 0.0 | 10.2 ± 1.3 | 6.5 ± 0.7 | 6.5 ± 0.4 | 17.7 ± 0.0 | 10.9 ± 0.5 | 21.9 ± 2.1 | 14.4 ± 1.2 | 17.1 ± 1.0 | 7.0 ± 0.4 |
| PaFadM | 5.9 ± 0.1 | 2.5 ± 2.1 | 2.3 ± 0.1 | 2.1 ± 0.4 | 13.9 ± 2.3 | 7.0 ± 0.5 | 18.1 ± 0.1 | 9.1 ± 2.7 | 6.0 ± 4.2 | 5.7 ± 0.1 |
| BaFadM | 7.9 ± 0.4 | 17.2 ± 2.0 | 6.3 ± 0.4 | 16.4 ± 0.5 | 21.9 ± 2.1 | 13.2 ± 0.2 | 32.2 ± 7.7 | 14.5 ± 0.7 | 31.8 ± 4.2 | 7.5 ± 0.8 |
| MtFadM1 | 8.0 ± 0.3 | 26.9 ± 7.8 | 14.4 ± 1.1 | 26.2 ± 0.6 | 37.9 ± 9.1 | 15.0 ± 0.2 | 29.8 ± 3.2 | 17.0 ± 1.7 | 28.1 ± 4.7 | 9.1 ± 1.0 |
| MtFadM4 | 10.0 ± 0.2 | 25.8 ± 2.8 | 12.0 ± 0.2 | 25.8 ± 0.7 | 31.6 ± 1.2 | 14.7 ± 0.4 | 29.8 ± 4.2 | 16.3 ± 2.6 | 28.4 ± 10.6 | 7.9 ± 3.5 |
| MtFadM3 | 11.4 ± 0.0 | 26.2 ± 9.3 | 9.0 ± 0.6 | 26.9 ± 0.6 | 13.9 ± 1.4 | 6.1 ± 0.6 | 19.8 ± 4.0 | 4.3 ± 0.5 | 32.8 ± 2.4 | 6.2 ± 0.2 |
| MtFadM2 | 11.8 ± 0.3 | 41.9 ± 3.6 | 18.8 ± 0.8 | 28.9 ± 0.2 | 43.5 ± 5.0 | 14.4 ± 0.9 | 33.2 ± 1.2 | 15.2 ± 2.4 | 35.4 ± 1.5 | 8.2 ± 0.8 |
| SoFadM | 13.9 ± 0.1 | 104.9 ± 17.1 | 25.3 ± 0.8 | 77.4 ± 1.2 | 32.0 ± 1.0 | 15.6 ± 1.4 | 39.0 ± 6.6 | 15.4 ± 0.5 | 40.2 ± 12.0 | 8.3 ± 2.9 |
| BbFadM | 15.5 ± 0.5 | 89.2 ± 4.8 | 25.2 ± 1.2 | 64.2 ± 0.4 | 20.2 ± 4.4 | 8.4 ± 0.3 | 29.1 ± 6.4 | 13.4 ± 0.3 | 34.2 ± 1.5 | 8.3 ± 1.9 |
| EciFadM | 24.7 ± 0.5 | 102.5 ± 7.6 | 29.1 ± 0.2 | 71.7 ± 1.0 | 41.6 ± 5.2 | 14.8 ± 0.3 | 39.9 ± 0.3 | 17.2 ± 0.8 | 38.7 ± 0.5 | 11.6 ± 2.7 |
| CtFadM | 26.4 ± 0.7 | 115.6 ± 3.1 | 20.5 ± 0.4 | 32.9 ± 1.1 | 20.6 ± 3.8 | 12.3 ± 2.1 | 27.8 ± 7.3 | 9.6 ± 1.5 | 38.6 ± 8.4 | 11.0 ± 2.0 |
| EcFadM | 33.3 ± 0.2 | 105.7 ± 0.8 | 30.3 ± 1.0 | 58.9 ± 0.8 | 40.0 ± 1.4 | 14.5 ± 1.0 | 44.6 ± 9.7 | 17.1 ± 0.0 | 45.3 ± 11.6 | 9.5 ± 1.2 |
| PsFadM | 50.0 ± 0.2 | 142.9 ± 7.0 | 43.3 ± 1.0 | 137.0 ± 0.2 | 49.5 ± 1.3 | 13.6 ± 0.3 | 39.0 ± 3.4 | 15.4 ± 3.5 | 36.9 ± 0.7 | 7.4 ± 0.8 |

FIG. 3

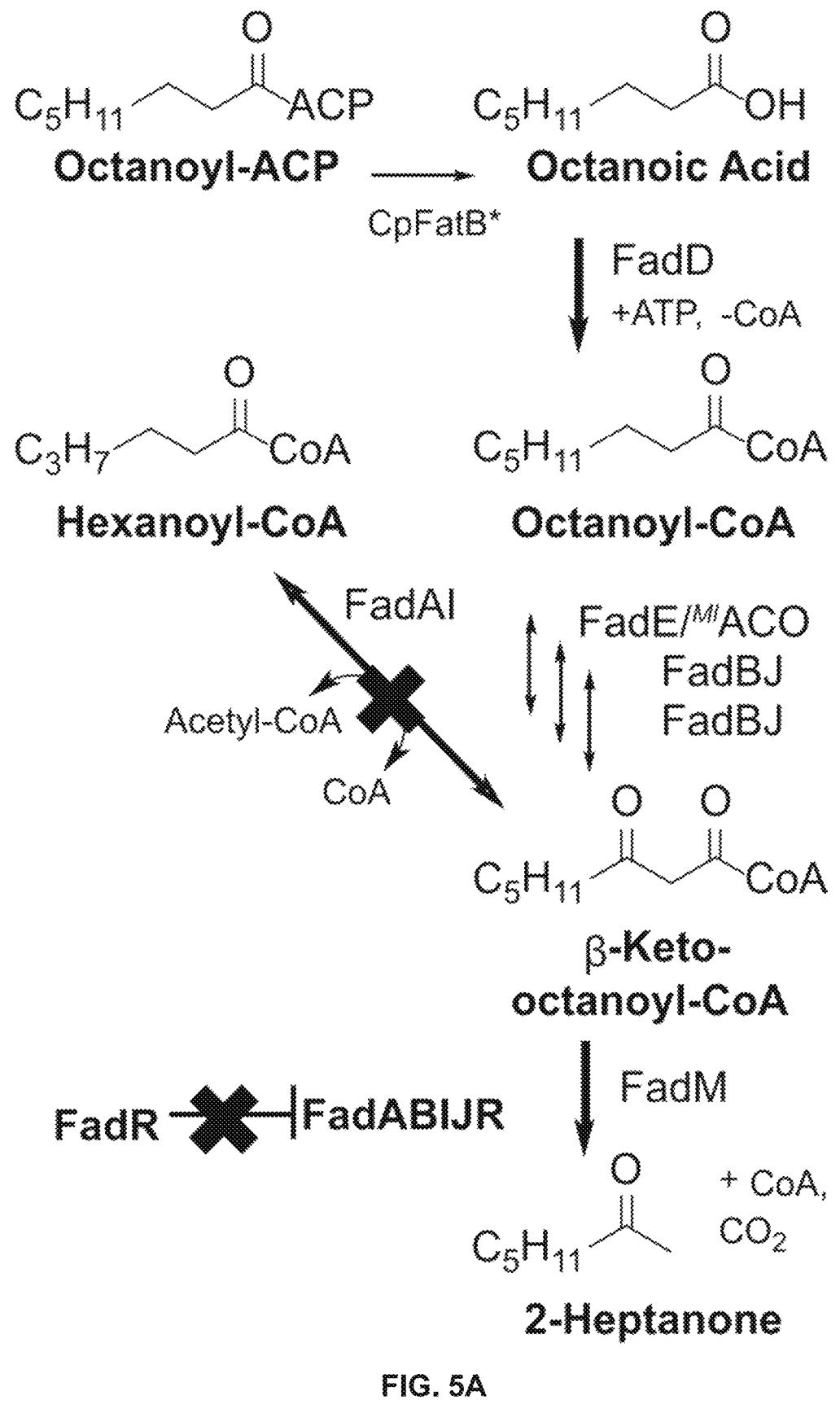

Octanoyl-ACP → Octanoic Acid
CpFatB*

FadD
+ATP, -CoA

Hexanoyl-CoA    Octanoyl-CoA

FadAI

Acetyl-CoA

CoA

FadE/$^{MI}$ACO
FadBJ
FadBJ

β-Keto-octanoyl-CoA

FadR —✗—|FadABIJR

FadM

+ CoA,
$CO_2$

2-Heptanone

FIG. 5A

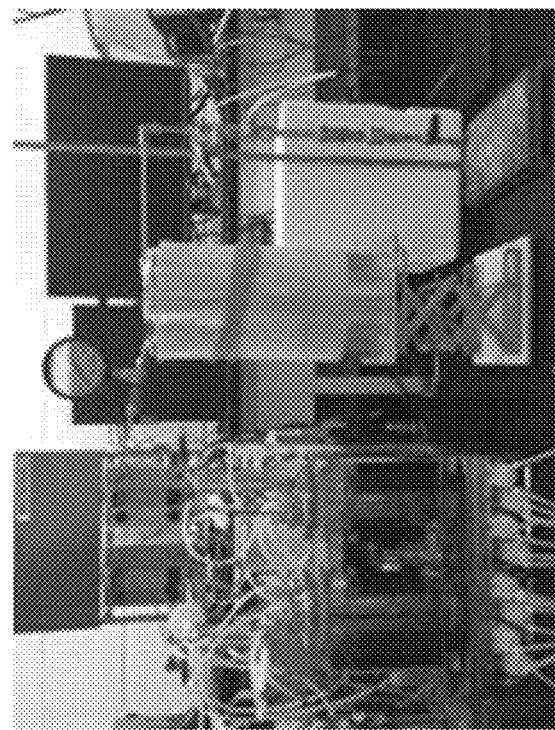
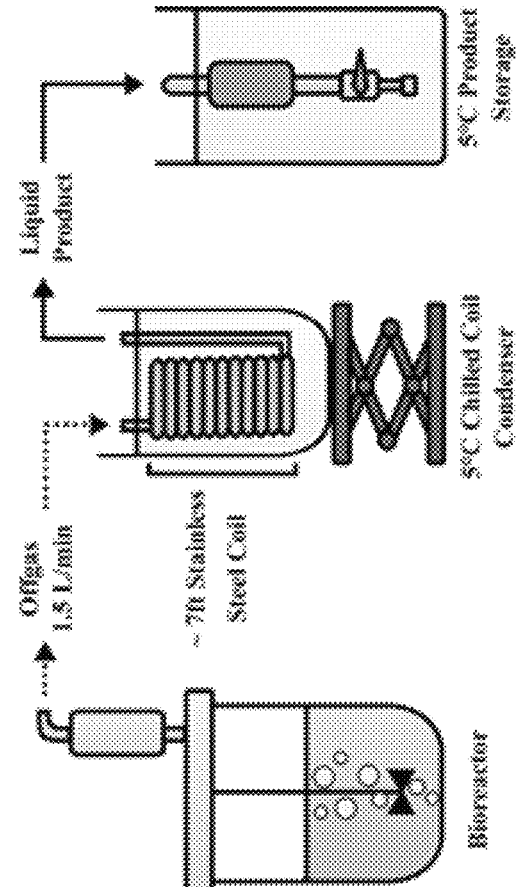
FIG. 7

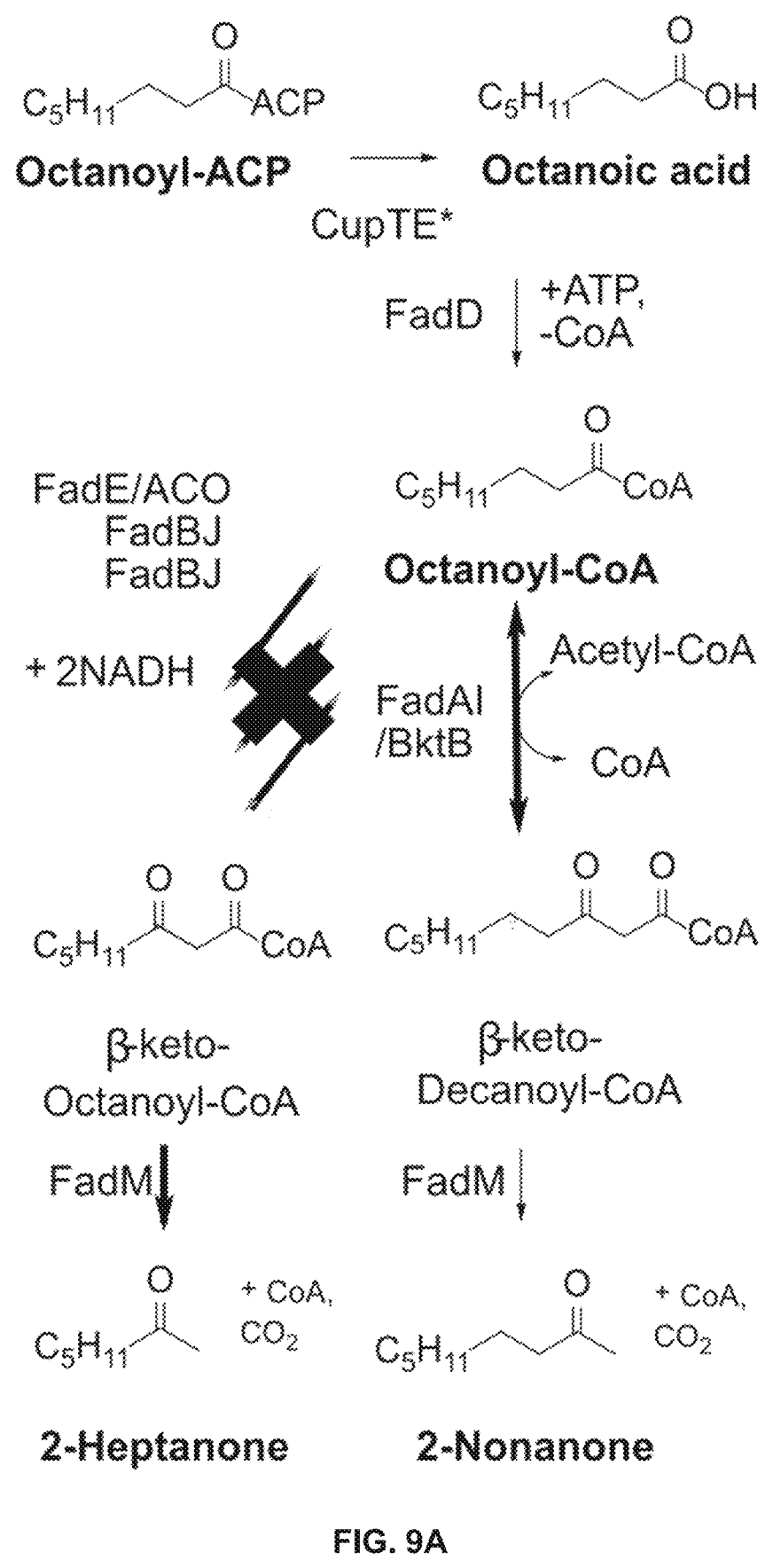

Octanoyl-ACP → Octanoic acid

CupTE*

FadD | +ATP, -CoA

FadE/ACO
FadBJ
FadBJ

+ 2NADH

Octanoyl-CoA

FadAl /BktB

Acetyl-CoA

CoA

β-keto-
Octanoyl-CoA

β-keto-
Decanoyl-CoA

FadM

FadM

+ CoA, $CO_2$

+ CoA, $CO_2$

2-Heptanone

2-Nonanone

FIG. 9A

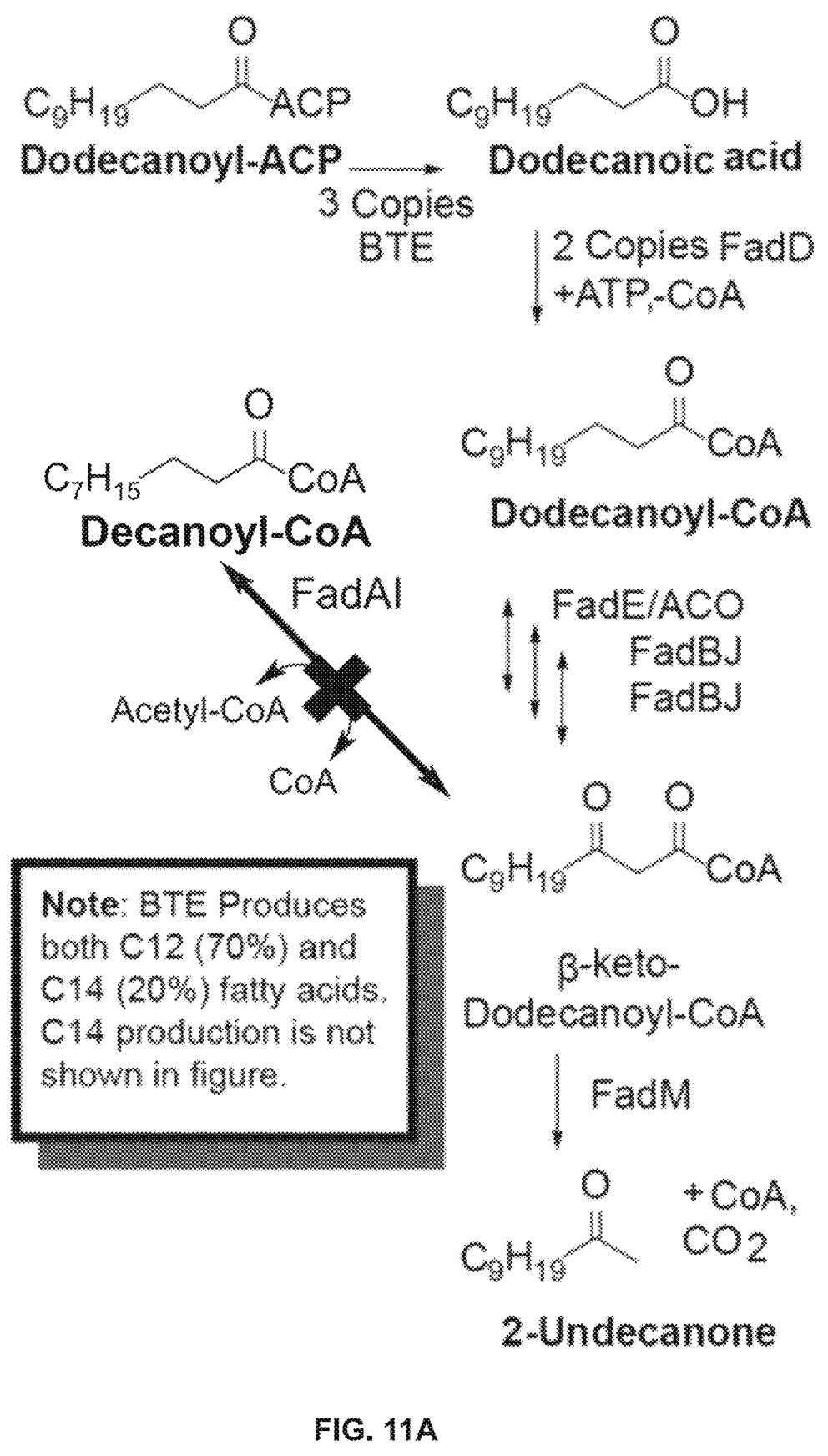

Dodecanoyl-ACP → Dodecanoic acid

3 Copies BTE

2 Copies FadD +ATP, -CoA

Decanoyl-CoA  Dodecanoyl-CoA

FadAl

Acetyl-CoA

CoA

FadE/ACO
FadBJ
FadBJ

Note: BTE Produces both C12 (70%) and C14 (20%) fatty acids. C14 production is not shown in figure.

β-keto-Dodecanoyl-CoA

FadM

+ CoA, $CO_2$

2-Undecanone

FIG. 11A

| -1 Pathway | | Enzyme | +1 Pathway | |
|---|---|---|---|---|
| CpFatB* | Heterologous Express | Acyl-ACP Thioesterase | Heterologous Express | CpFatB* |
| FadD6 | Upregulate or HE | Acyl-CoA Synthetase | Upregulate or HE | FadD6 |
| FadE/*ACO | Upregulate or HE | Acyl-CoA Dehydrogenase | Detrimental - Delete | FadE |
| FadBJ | Upregulate or HE | 3-OH-Acyl CoA Dehydrogenase | Detrimental - Delete | FadBJ |
| FadBJ | Upregulate or HE | Enoyl-CoA Hydratase | Detrimental - Delete | FadBJ |
| FadAA | Detrimental - Delete | Thiolase | Heterologous Express | BktB |
| PsFadM | Heterologous Express | Beta-Keto Acyl-CoA Thioesterase | Heterologous Express | PsFadM |
| FadR | Can Delete | Beta-Ox regulator | Can Delete | FadR |

FIG. 13

SEQUENCE LISTING

<160> NUMBER OF SEQ ID NOS: 60

<210> SEQ ID NO 1
<211> LENGTH: 900
<212> TYPE: DNA
<213> ORGANISM: Cuphea palustris

<400> SEQUENCE: 1

```
atgtttgacc gcaaatctaa acgtccgagc atgctgatgg atagcttcgg tctggaacgt      60
gttgtccagg atggtctggt tttccgccaa tccttctcca ttcgtagcta cgaaatctgt     120
gcggaccgca cggcgagcat ggagaccgtg atgaaccacg ttcaggaaac cagcctgaac     180
cagtgtaagt ccatcggcct gctggacgac ggtttcggtc gctcaccgga aatgtgtaaa     240
cgcgacctga tttgggttgt aacccgtatg aaaattatgg taaaccgtta tccgacctgg     300
ggcgacacca ttgaagtctc cacctggctg tcccagtccg gtaaaattgg catgggtcgc     360
gactggctga ttagcgattg taataccggt gaaatactgg ttcgtgcaac ctcagtttac     420
gccatgatga accagaaaac gcgtcgcttc tctaaactgc cccacgaagt acgccaggag     480
```

```
ttcgcgccgc acttcttaga ctccccgccg gccattgaag acaacgacgg taaactgcag    540
aaattcgatg tgaaaaccgg tgattccatc cgcaaaggtc tgaccccggg ctggtacgac    600
ctggacgtaa accagcacgt ttccaatgtc aaatatatcg gttggatcct ggaatccatg    660
ccgaccgaag ttctggaaac ccaagaactt tgcagcctga ctctcgaata ccgtcgcgaa    720
tgcggtcgcg actcagtact tgagagcgta acctccatgg accgtctaa agttggtgat     780 cgttttcagt atcgtcatct gctgcgtctg gaagatggtg cggacattat gaagggccgt    840
accgaatggc gtccgaaaaa cgcgggcact aatggtgcta tctccactgg gaaaacataa    900
```

<210> SEQ ID NO 2
<211> LENGTH: 299
<212> TYPE: PRT
<213> ORGANISM: Cuphea palustris

<400> SEQUENCE: 2

```
Met Phe Asp Arg Lys Ser Lys Arg Pro Ser Met Leu Met Asp Ser Phe
1               5                   10                  15

Gly Leu Glu Arg Val Val Gln Asp Gly Leu Val Phe Arg Gln Ser Phe
                20                  25                  30

Ser Ile Arg Ser Tyr Glu Ile Cys Ala Asp Arg Thr Ala Ser Met Glu
            35                  40                  45

Thr Val Met Asn His Val Gln Glu Thr Ser Leu Asn Gln Cys Lys Ser
        50                  55                  60

Ile Gly Leu Leu Asp Asp Gly Phe Gly Arg Ser Pro Glu Met Cys Lys
65                  70                  75                  80

Arg Asp Leu Ile Trp Val Val Thr Arg Met Lys Ile Met Val Asn Arg
                85                  90                  95

Tyr Pro Thr Trp Gly Asp Thr Ile Glu Val Ser Thr Trp Leu Ser Gln
            100                 105                 110

Ser Gly Lys Ile Gly Met Gly Arg Asp Trp Leu Ile Ser Asp Cys Asn
        115                 120                 125

Thr Gly Glu Ile Leu Val Arg Ala Thr Ser Val Tyr Ala Met Met Asn
        130                 135                 140

Gln Lys Thr Arg Arg Phe Ser Lys Leu Pro His Glu Val Arg Gln Glu
145                 150                 155                 160

Phe Ala Pro His Phe Leu Asp Ser Pro Pro Ala Ile Glu Asp Asn Asp
                165                 170                 175

Gly Lys Leu Gln Lys Phe Asp Val Lys Thr Gly Asp Ser Ile Arg Lys
            180                 185                 190

Gly Leu Thr Pro Gly Trp Tyr Asp Leu Asp Val Asn Gln His Val Ser
        195                 200                 205

Asn Val Lys Tyr Ile Gly Trp Ile Leu Glu Ser Met Pro Thr Glu Val
        210                 215                 220

Leu Glu Thr Gln Glu Leu Cys Ser Leu Thr Leu Glu Tyr Arg Arg Glu
225                 230                 235                 240

Cys Gly Arg Asp Ser Val Leu Glu Ser Val Thr Ser Met Asp Pro Ser
                245                 250                 255

Lys Val Gly Asp Arg Phe Gln Tyr Arg His Leu Leu Arg Leu Glu Asp
            260                 265                 270

Gly Ala Asp Ile Met Lys Gly Arg Thr Glu Trp Arg Pro Lys Asn Ala
        275                 280                 285

Gly Thr Asn Gly Ala Ile Ser Thr Gly Lys Thr
        290                 295
```

```
<210> SEQ ID NO 3
<211> LENGTH: 906
<212> TYPE: DNA
<213> ORGANISM: Umbellularia californica

<400> SEQUENCE: 3
atgactctag agtggaaacc gaaaccaaaa ctgcctcaac tgctggatga tcacttcggt      60
ctgcacggtc tggtgtttcg tcgtactttc gcaattcgtt cttatgaagt gggtccagat     120
cgttctacct ccatcctggc cgtcatgaac cacatgcagg aagccaccct gaatcacgcg     180
aaatctgttg gtatcctggg tgatggtttc ggcactactc tggaaatgtc taaacgtgac     240
ctgatgtggg tagtgcgtcg cacccacgta gcagtagagc gctaccctac ttggggtgac     300
actgtggaag tcgagtgttg gattggcgcg tccggtaaca atggtatgcg tcgcgatttt     360
ctggtccgtg actgtaaaac gggcgaaatc ctgacgcgtt gcacctccct gagcgttctg     420
atgaacaccc gcactcgtcg cctgtctacc atcccggacg aagtgcgcgg tgagatcggt     480
cctgctttca tcgataacgt ggcagttaaa gacgacgaaa tcaagaaact gcaaaaactg     540
aacgactcca ccgcggacta catccagggc ggtctgactc cgcgctggaa cgacctggat     600
gttaatcagc atgtgaacaa cctgaaatac gttgcttggg tcttcgagac tgtgccggac     660 agcatttttcg aaagccatca catttcctct tttactctgg agtaccgtcg cgaatgtact     720
cgcgactccg ttctgcgcag cctgaccacc gtaagcggcg ttctagcga ggcaggtctg     780 gtctgcgacc atctgctgca actggaaggc ggctccgaag tcctgcgtgc gcgtacggag     840
tggcgtccaa agctgacgga ttctttccgc ggcatctccg taattccggc ggaacctcgt     900
gtttaa                                                                906

<210> SEQ ID NO 4
<211> LENGTH: 301
<212> TYPE: PRT
<213> ORGANISM: Umbellularia californica

<400> SEQUENCE: 4

Met Thr Leu Glu Trp Lys Pro Lys Pro Lys Leu Pro Gln Leu Leu Asp
1               5                   10                  15

Asp His Phe Gly Leu His Gly Leu Val Phe Arg Arg Thr Phe Ala Ile
            20                  25                  30

Arg Ser Tyr Glu Val Gly Pro Asp Arg Ser Thr Ser Ile Leu Ala Val
        35                  40                  45

Met Asn His Met Gln Glu Ala Thr Leu Asn His Ala Lys Ser Val Gly
    50                  55                  60

Ile Leu Gly Asp Gly Phe Gly Thr Thr Leu Glu Met Ser Lys Arg Asp
65                  70                  75                  80

Leu Met Trp Val Val Arg Arg Thr His Val Ala Val Glu Arg Tyr Pro
                85                  90                  95

Thr Trp Gly Asp Thr Val Glu Val Glu Cys Trp Ile Gly Ala Ser Gly
            100                 105                 110

Asn Asn Gly Met Arg Arg Asp Phe Leu Val Arg Asp Cys Lys Thr Gly
        115                 120                 125

Glu Ile Leu Thr Arg Cys Thr Ser Leu Ser Val Leu Met Asn Thr Arg
    130                 135                 140

Thr Arg Arg Leu Ser Thr Ile Pro Asp Glu Val Arg Gly Glu Ile Gly
145                 150                 155                 160
```

```
Pro Ala Phe Ile Asp Asn Val Ala Val Lys Asp Asp Glu Ile Lys Lys
            165                 170                 175

Leu Gln Lys Leu Asn Asp Ser Thr Ala Asp Tyr Ile Gln Gly Gly Leu
            180                 185                 190

Thr Pro Arg Trp Asn Asp Leu Asp Val Asn Gln His Val Asn Asn Leu
            195                 200                 205

Lys Tyr Val Ala Trp Val Phe Glu Thr Val Pro Asp Ser Ile Phe Glu
    210                 215                 220

Ser His His Ile Ser Ser Phe Thr Leu Glu Tyr Arg Arg Glu Cys Thr
225                 230                 235                 240

Arg Asp Ser Val Leu Arg Ser Leu Thr Thr Val Ser Gly Gly Ser Ser
            245                 250                 255

Glu Ala Gly Leu Val Cys Asp His Leu Leu Gln Leu Glu Gly Gly Ser
            260                 265                 270

Glu Val Leu Arg Ala Arg Thr Glu Trp Arg Pro Lys Leu Thr Asp Ser
            275                 280                 285

Phe Arg Gly Ile Ser Val Ile Pro Ala Glu Pro Arg Val
            290                 295                 300

<210> SEQ ID NO 5
<211> LENGTH: 399
<212> TYPE: DNA
<213> ORGANISM: Escherichia coli

<400> SEQUENCE: 5
atgcaaacac aaatcaaagt tcgtggatat catctcgacg tttaccagca cgtcaacaac      60
gcccgctacc ttgaatttct cgaagaagcc cgctgggatg ggttggaaaa tagcgacagt     120
tttcagtgga tgacggccca taacatcgcc ttcgtcgtgg tcaatatcaa tattaactat     180
cgtcgcccag cggtattaag tgacctgtta actattacca gtcagttgca gcaattaaac     240
ggtaaaagcg gcatcttaag ccaggtcatt acactggagc cggaagggca ggtggtagcg     300
gatgcgctta ttacgtttgt ttgtattgat cttaaaacgc agaaagcatt agctctggaa     360
ggggaattgc gcgaaaagct ggagcagatg gttaagtaa                            399

<210> SEQ ID NO 6
<211> LENGTH: 132
<212> TYPE: PRT
<213> ORGANISM: Escherichia coli

<400> SEQUENCE: 6

Met Gln Thr Gln Ile Lys Val Arg Gly Tyr His Leu Asp Val Tyr Gln
1               5                   10                  15

His Val Asn Asn Ala Arg Tyr Leu Glu Phe Leu Glu Glu Ala Arg Trp
            20                  25                  30

Asp Gly Leu Glu Asn Ser Asp Ser Phe Gln Trp Met Thr Ala His Asn
            35                  40                  45

Ile Ala Phe Val Val Asn Ile Asn Ile Asn Tyr Arg Arg Pro Ala
    50                  55                  60

Val Leu Ser Asp Leu Leu Thr Ile Thr Ser Gln Leu Gln Gln Leu Asn
65                  70                  75                  80

Gly Lys Ser Gly Ile Leu Ser Gln Val Ile Thr Leu Glu Pro Glu Gly
            85                  90                  95

Gln Val Val Ala Asp Ala Leu Ile Thr Phe Val Cys Ile Asp Leu Lys
            100                 105                 110

Thr Gln Lys Ala Leu Ala Leu Glu Gly Glu Leu Arg Glu Lys Leu Glu
```

```
            115               120               125

Gln Met Val Lys
    130

<210> SEQ ID NO 7
<211> LENGTH: 432
<212> TYPE: DNA
<213> ORGANISM: Providencia sneebia

<400> SEQUENCE: 7
atggctaccc agattaaagt ttacgggcac catatcgatg tgtttaacca cgtgaataat      60
gcgcgctacc ttgagttcta cgaggaagcg cgctgggcct ggttggagaa tcacaacctg     120
ctgaacttct tgttaaaaaa caatttaggt atggtggcgg ttaacatcaa cattaattat     180
tgccaaggtg ctgtcttgtt tgatcaattg acggttatca gtcgtttgga acgcatcgga     240
acgaaatcag cttcctgcta ccagcaaatc atccgtgaga agaacggaaa aaagaccttg     300
atctcggatg tcaccgtcac gtttgtcttc gttgaattgg ctaccaacaa atcagtagtt     360
atcagcggag agttgttgga acacttggaa cctttgcttc aaggggaatc cgaccaattt     420
atcgaagtta at                                                         432

<210> SEQ ID NO 8
<211> LENGTH: 144
<212> TYPE: PRT
<213> ORGANISM: Providencia sneebia

<400> SEQUENCE: 8

Met Ala Thr Gln Ile Lys Val Tyr Gly His His Ile Asp Val Phe Asn
1               5                   10                  15

His Val Asn Asn Ala Arg Tyr Leu Glu Phe Tyr Glu Glu Ala Arg Trp
            20                  25                  30

Ala Trp Leu Glu Asn His Asn Leu Leu Asn Phe Leu Leu Lys Asn Asn
        35                  40                  45

Leu Gly Met Val Ala Val Asn Ile Asn Ile Asn Tyr Cys Gln Gly Ala
    50                  55                  60

Val Leu Phe Asp Gln Leu Thr Val Ile Ser Arg Leu Glu Arg Ile Gly
65                  70                  75                  80

Thr Lys Ser Ala Ser Cys Tyr Gln Gln Ile Ile Arg Glu Lys Asn Gly
                85                  90                  95

Lys Lys Thr Leu Ile Ser Asp Val Thr Val Thr Phe Val Phe Val Glu
            100                 105                 110

Leu Ala Thr Asn Lys Ser Val Val Ile Ser Gly Glu Leu Leu Glu His
        115                 120                 125

Leu Glu Pro Leu Leu Gln Gly Glu Ser Asp Gln Phe Ile Glu Val Asn
    130                 135                 140

<210> SEQ ID NO 9
<211> LENGTH: 1686
<212> TYPE: DNA
<213> ORGANISM: Escherichia coli

<400> SEQUENCE: 9
ttgaagaagg tttggcttaa ccgttatccc gcggacgttc cgacggagat caaccctgac      60
cgttatcaat ctctggtaga tatgtttgag cagtcggtcg cgcgctacgc cgatcaacct     120
gcgtttgtga atatggggga ggtaatgacc ttccgcaagc tggaagaacg cagtcgcgcg     180
tttgccgctt atttgcaaca agggttgggg ctgaagaaag cgatcgcgt tgcgttgatg     240
```

-continued

```
atgcctaatt tattgcaata tccggtggcg ctgtttggca ttttgcgtgc cgggatgatc    300
gtcgtaaacg ttaacccgtt gtataccccg cgtgagcttg agcatcagct taacgatagc    360
ggcgcatcgg cgattgttat cgtgtctaac tttgctcaca cactggaaaa agtggttgat    420
aaaaccgccg ttcagcacgt aattctgacc cgtatgggcg atcagctatc tacggcaaaa    480
ggcacggtag tcaatttcgt tgttaaatac atcaagcgtt tggtgccgaa ataccatctg    540
ccagatgcca tttcatttcg tagcgcactg cataacggct accggatgca gtacgtcaaa    600
cccgaactgg tgccggaaga tttagctttt ctgcaataca ccggcggcac cactggtgtg    660
gcgaaaggcg cgatgctgac tcaccgcaat atgctggcga acctggaaca ggttaacgcg    720
acctatggtc cgctgttgca tccgggcaaa gagctggtgg tgacggcgct gccgctgtat    780 cacattttg ccctgaccat taactgcctg ctgtttatcg aactgggtgg gcagaacctg    840
cttatcacta acccgcgcga tattccaggg ttggtaaaag agttagcgaa atatccgttt    900
accgctatca cgggcgttaa caccttgttc aatgcgttgc tgaacaataa agagttccag    960
cagctggatt tctccagtct gcatctttcc gcaggcggtg ggatgccagt gcagcaagtg   1020
gtggcagagc gttgggtgaa actgaccgga cagtatctgc tggaaggcta tggccttacc   1080
gagtgtgcgc cgctggtcag cgttaaccca tatgatattg attatcatag tggtagcatc   1140
ggtttgccgg tgccgtcgac ggaagccaaa ctggtggatg atgatgataa tgaagtacca   1200
ccaggtcaac cgggtgagct ttgtgtcaaa ggaccgcagg tgatgctggg ttactggcag   1260
cgtcccgatg ctaccgatga aatcatcaaa aatggctggt tacacaccgg cgacatcgcg   1320
gtaatggatg aagaaggatt cctgcgcatt gtcgatcgta aaaaagacat gattctggtt   1380
tccggtttta acgtctatcc caacgagatt gaagatgtcg tcatgcagca tcctggcgta   1440
caggaagtcg cggctgttgg cgtaccttcc ggctccagtg gtgaagcggt gaaaatcttc   1500
gtagtgaaaa aagatccatc gcttaccgaa gagtcactgg tgacttttg ccgccgtcag   1560 ctcacgggat acaaagtacc gaagctggtg gagtttcgtg atgagttacc gaaatctaac   1620
gtcggaaaaa ttttgcgacg agaattacgt gacgaagcgc gcggcaaagt ggacaataaa   1680
gcctga                                                             1686
```

<210> SEQ ID NO 10  
<211> LENGTH: 561  
<212> TYPE: PRT  
<213> ORGANISM: Escherichia coli

<400> SEQUENCE: 10

```
Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110
```

```
Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
    130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
                180                 185                 190

Gly Tyr Arg Met Gln Tyr Val Lys Pro Glu Leu Val Pro Glu Asp Leu
                195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
                260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro
                325                 330                 335

Val Gln Gln Val Val Ala Glu Arg Trp Val Lys Leu Thr Gly Gln Tyr
                340                 345                 350

Leu Leu Glu Gly Tyr Gly Leu Thr Glu Cys Ala Pro Leu Val Ser Val
        355                 360                 365

Asn Pro Tyr Asp Ile Asp Tyr His Ser Gly Ser Ile Gly Leu Pro Val
    370                 375                 380

Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
                405                 410                 415

Gly Tyr Trp Gln Arg Pro Asp Ala Thr Asp Glu Ile Ile Lys Asn Gly
                420                 425                 430

Trp Leu His Thr Gly Asp Ile Ala Val Met Asp Glu Glu Gly Phe Leu
        435                 440                 445

Arg Ile Val Asp Arg Lys Lys Asp Met Ile Leu Val Ser Gly Phe Asn
    450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Ser Gly Glu Ala
                485                 490                 495

Val Lys Ile Phe Val Val Lys Lys Asp Pro Ser Leu Thr Glu Glu Ser
                500                 505                 510

Leu Val Thr Phe Cys Arg Arg Gln Leu Thr Gly Tyr Lys Val Pro Lys
                515                 520                 525
```

-continued

```
Leu Val Glu Phe Arg Asp Glu Leu Pro Lys Ser Asn Val Gly Lys Ile
    530                 535                 540

Leu Arg Arg Glu Leu Arg Asp Glu Ala Arg Gly Lys Val Asp Asn Lys
545                 550                 555                 560

Ala

<210> SEQ ID NO 11
<211> LENGTH: 1797
<212> TYPE: DNA
<213> ORGANISM: Mycobacterium tuberculosis

<400> SEQUENCE: 11
atgagcgatt attatggtgg tgcacatacc accgttcgtc tgattgatct ggcaacccgt      60
atgcctcgtg ttctggcaga tacaccggtt attgttcgtg gtgcaatgac cggtctgctg     120
gcacgtccga atagcaaagc aagcattggc accgtttttc aggatcgtgc agcacgttat     180
ggtgatcgtg tttttctgaa atttggtgat cagcaactga cctatcgtga tgcaaatgca     240
accgcaaatc gttatgcagc agtgctggca gcacgtggtg ttggtccggg tgatgttgtt     300
ggtattatgc tgcgtaatag cccgagcacc gttctggcaa tgctggcaac cgttaaatgt     360
ggtgccattg caggtatgct gaattatcat cagcgtggtg aagttctggc acatagcctg     420
ggcctgctgg atgcaaaagt tctgattgca gaaagcgatc tggttagcgc agttgcagaa     480
tgcggtgcaa gccgtggtcg tgttgccggt gatgttctga ccgttgaaga tgttgaacgt     540
tttgcaacca ccgctccggc aaccaatccg gcaagcgcaa gcgcagttca ggcaaaagat     600
accgcctttt atatctttac cagcggcacc accggttttc gaaagcaag cgttatgacc       660 catcatcgtt ggctgcgtgc actggcagtt tttggtggta tgggtctgcg tctgaaaggt     720
agcgataccc tgtatagctg tctgccgctg tatcataata tgcactgac cgtggcagtt       780 tccagcgtga ttaatagcgg tgcaaccctg gcactgggta aaagttttag cgcaagccgt     840
ttttgggatg aagttattgc aaatcgtgca accgcctttg tgtatattgg tgaaatttgt     900
cgctatctgc tgaatcagcc tgcaaaaccg accgatcgtg cacatcaggt tcgtgttatt     960
tgtggtaatg cctgcgtcc ggaaatctgg atgaattta ccacccgttt tggtgttgca      1020
cgtgtttgtg agttttatgc agccagcgaa ggtaatagcg cctttattaa cattttttaac   1080 gttccgcgta ccgcaggcgt tagcccgatg ccgctggcat ttgttgaata tgatctggat    1140
accggtgatc cgctgcgtga tgcgagcggt cgtgttcgtc gtgtgccgga tggtgaaccg    1200
ggtctgctgc tgagccgtgt taatcgtctg caaccgtttg atggttatac cgatccggtt    1260
gcaagcgaaa aaaactggt tcgtaatgca tttcgtgatg cgattgttg gtttaataca     1320 ggtgatgtta tgagtccgca gggtatgggc catgcagcct ttgttgatcg tctgggtgat    1380
acctttcgtt ggaaaggtga aaatgttgcc accacccagg ttgaagcagc actggcaagc    1440
gatcagaccg tggaagaatg taccgtttat ggtgtgcaga ttcctcgtac cggtggtcgt    1500
gccggtatgg cagcaattac cctgcgtgcc ggtgcagaat ttgatggtca ggcactggca    1560
cgcaccgtgt atggtcatct gcctggttat gcactgcctc tgtttgttcg tgttgtgggt    1620
agcctggcgc ataccacaac ctttaaaagc cgtaaagttg aactgcgtaa tcaggcctat    1680
ggtgcagata ttgaagatcc gctgtatgta ctggcaggtc cggatgaagg ttatgttccg    1740
tattatgcag aatatccgga agaagttagc ctgggtcgtc gtcctcaggg ttaataa      1797

<210> SEQ ID NO 12
<211> LENGTH: 597
```

```
<212> TYPE: PRT
<213> ORGANISM: Mycobacterium tuberculosis

<400> SEQUENCE: 12

Met Ser Asp Tyr Tyr Gly Gly Ala His Thr Thr Val Arg Leu Ile Asp
1               5                   10                  15

Leu Ala Thr Arg Met Pro Arg Val Leu Ala Asp Thr Pro Val Ile Val
            20                  25                  30

Arg Gly Ala Met Thr Gly Leu Leu Ala Arg Pro Asn Ser Lys Ala Ser
        35                  40                  45

Ile Gly Thr Val Phe Gln Asp Arg Ala Ala Arg Tyr Gly Asp Arg Val
    50                  55                  60

Phe Leu Lys Phe Gly Asp Gln Gln Leu Thr Tyr Arg Asp Ala Asn Ala
65                  70                  75                  80

Thr Ala Asn Arg Tyr Ala Ala Val Leu Ala Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
        355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Arg Val Pro Asp Gly Glu Pro
385                 390                 395                 400
```

-continued

```
Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
        435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
            485                 490                 495

Thr Gly Gly Arg Ala Gly Met Ala Ala Ile Thr Leu Arg Ala Gly Ala
        500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
            565                 570                 575

Gly Tyr Val Pro Tyr Tyr Ala Glu Tyr Pro Glu Glu Val Ser Leu Gly
            580                 585                 590

Arg Arg Pro Gln Gly
        595

<210> SEQ ID NO 13
<211> LENGTH: 2190
<212> TYPE: DNA
<213> ORGANISM: Escherichia coli

<400> SEQUENCE: 13
atgctttaca aaggcgacac cctgtacctt gactggctgg aagatggcat tgccgaactg       60
gtatttgatg ccccaggttc agttaataaa ctcgacactg cgaccgtcgc cagcctcggc      120
gaggccatcg gcgtgctgga acagcaatca gatctaaaag ggctgctgct gcgttcgaac      180
aaagcagcct ttatcgtcgg tgctgatatc accgaatttt tgtccctgtt cctcgttcct      240
gaagaacagt taagtcagtg gctgcacttt gccaatagcg tgtttaatcg cctggaagat      300
ctgccggtgc cgaccattgc tgccgtcaat ggctatgcgc tgggcggtgg ctgcgaatgc      360
gtgctggcga ccgattatcg tctggcgacg ccggatctgc gcatcggtct gccggaaacc      420
aaactgggca tcatgcctgg ctttggcggt tctgtacgta tgccacgtat gctgggcgct      480
gacagtgcgc tggaaatcat tgccgccggt aaagatgtcg cgcgcgatca ggcgctgaaa      540
atcggtctgg tggatggcgt agtcaaagca gaaaaactgg ttgaaggcgc aaaggcggtt      600
ttacgccagg ccattaacgg cgacctcgac tggaaagcaa aacgtcagcc gaagctggaa      660
ccactaaaac tgagcaagat tgaagccacc atgagcttca ccatcgctaa agggatggtc      720
gcacaaacag cggggaaaca ttatccggcc cccatcaccg cagtaaaaac cattgaagct      780
gcggcccgtt ttggtcgtga agaagcctta aacctggaaa acaaaagttt tgtcccgctg      840
gcgcatacca cgaagcccg cgcactggtc ggcattttcc ttaacgatca atatgtaaaa      900
ggcaaagcga agaaactcac caaagacgtt gaaaccccga acaggccgc ggtgctgggt      960
```

```
gcaggcatta tgggcggcgg catcgcttac cagtctgcgt ggaaaggcgt gccggttgtc    1020
atgaaagata tcaacgacaa gtcgttaacc ctcggcatga ccgaagccgc gaaactgctg    1080
aacaagcagc ttgagcgcgg caagatcgat ggtctgaaac tggctggcgt gatctccaca    1140
atccacccaa cgctcgacta cgccggattt gaccgcgtgg atattgtggt agaagcggtt    1200
gttgaaaacc cgaaagtgaa aaaagccgta ctggcagaaa ccgaacaaaa agtacgccag    1260
gataccgtgc tggcgtctaa cacttcaacc attcctatca gcgaactggc caacgcgctg    1320
gaacgcccgg aaaacttctg cgggatgcac ttctttaacc cggtccaccg aatgccgttg    1380
gtagaaatta ttcgcggcga aaaagctcc gacgaaacca tcgcgaaagt tgtcgcctgg    1440
gcgagcaaga tgggcaagac gccgattgtg gttaacgact gccccggctt ctttgttaac    1500
cgcgtgctgt ccccgtattt cgccggtttc agccagctgc tgcgcgacgg cgcggatttc    1560
cgcaagatcg acaaagtgat ggaaaaacag tttggctggc cgatgggccc ggcatatctg    1620
ctggacgttg tgggcattga taccgcgcat cacgctcagg ctgtcatggc agcaggcttc    1680
ccgcagcgga tgcagaaaga ttaccgcgat gccatcgacg cgctgtttga tgccaaccgc    1740
tttggtcaga gaacggcct cggtttctgg cgttataaag aagacagcaa aggtaagccg    1800
aagaaagaag aagacgccgc cgttgaagac ctgctggcag aagtgagcca gccgaagcgc    1860
gatttcagcg aagaagagat tatcgcccgc atgatgatcc cgatggtcaa cgaagtggtg    1920
cgctgtctgg aggaaggcat tatcgccact ccggcggaag cggatatggc gctggtctac    1980
ggcctgggct ccctccgtt ccacggcggc gcgttccgct ggctggacac cctcggtagc    2040
gcaaaatacc tcgatatggc acagcaatat cagcacctcg gcccgctgta tgaagtgccg    2100
gaaggtctgc gtaataaagc gcgtcataac gaaccgtact atcctccggt tgagccagcc    2160
cgtccggttg cgacctgaa aacggcttaa    2190
```

<210> SEQ ID NO 14
<211> LENGTH: 729
<212> TYPE: PRT
<213> ORGANISM: Escherichia coli

<400> SEQUENCE: 14

```
Met Leu Tyr Lys Gly Asp Thr Leu Tyr Leu Asp Trp Leu Glu Asp Gly
1               5                   10                  15

Ile Ala Glu Leu Val Phe Asp Ala Pro Gly Ser Val Asn Lys Leu Asp
            20                  25                  30

Thr Ala Thr Val Ala Ser Leu Gly Glu Ala Ile Gly Val Leu Glu Gln
        35                  40                  45

Gln Ser Asp Leu Lys Gly Leu Leu Leu Arg Ser Asn Lys Ala Ala Phe
    50                  55                  60

Ile Val Gly Ala Asp Ile Thr Glu Phe Leu Ser Leu Phe Leu Val Pro
65                  70                  75                  80

Glu Glu Gln Leu Ser Gln Trp Leu His Phe Ala Asn Ser Val Phe Asn
                85                  90                  95

Arg Leu Glu Asp Leu Pro Val Pro Thr Ile Ala Ala Val Asn Gly Tyr
            100                 105                 110

Ala Leu Gly Gly Gly Cys Glu Cys Val Leu Ala Thr Asp Tyr Arg Leu
        115                 120                 125

Ala Thr Pro Asp Leu Arg Ile Gly Leu Pro Glu Thr Lys Leu Gly Ile
    130                 135                 140

Met Pro Gly Phe Gly Gly Ser Val Arg Met Pro Arg Met Leu Gly Ala
```

-continued

```
145             150             155             160

Asp Ser Ala Leu Glu Ile Ile Ala Ala Gly Lys Asp Val Gly Ala Asp
            165             170             175

Gln Ala Leu Lys Ile Gly Leu Val Asp Gly Val Val Lys Ala Glu Lys
            180             185             190

Leu Val Glu Gly Ala Lys Ala Val Leu Arg Gln Ala Ile Asn Gly Asp
            195             200             205

Leu Asp Trp Lys Ala Lys Arg Gln Pro Lys Leu Glu Pro Leu Lys Leu
            210             215             220

Ser Lys Ile Glu Ala Thr Met Ser Phe Thr Ile Ala Lys Gly Met Val
225             230             235             240

Ala Gln Thr Ala Gly Lys His Tyr Pro Ala Pro Ile Thr Ala Val Lys
            245             250             255

Thr Ile Glu Ala Ala Ala Arg Phe Gly Arg Glu Glu Ala Leu Asn Leu
            260             265             270

Glu Asn Lys Ser Phe Val Pro Leu Ala His Thr Asn Glu Ala Arg Ala
            275             280             285

Leu Val Gly Ile Phe Leu Asn Asp Gln Tyr Val Lys Gly Lys Ala Lys
            290             295             300

Lys Leu Thr Lys Asp Val Glu Thr Pro Lys Gln Ala Ala Val Leu Gly
305             310             315             320

Ala Gly Ile Met Gly Gly Gly Ile Ala Tyr Gln Ser Ala Trp Lys Gly
            325             330             335

Val Pro Val Val Met Lys Asp Ile Asn Asp Lys Ser Leu Thr Leu Gly
            340             345             350

Met Thr Glu Ala Ala Lys Leu Leu Asn Lys Gln Leu Glu Arg Gly Lys
            355             360             365

Ile Asp Gly Leu Lys Leu Ala Gly Val Ile Ser Thr Ile His Pro Thr
            370             375             380

Leu Asp Tyr Ala Gly Phe Asp Arg Val Asp Ile Val Val Glu Ala Val
385             390             395             400

Val Glu Asn Pro Lys Val Lys Lys Ala Val Leu Ala Glu Thr Glu Gln
            405             410             415

Lys Val Arg Gln Asp Thr Val Leu Ala Ser Asn Thr Ser Thr Ile Pro
            420             425             430

Ile Ser Glu Leu Ala Asn Ala Leu Glu Arg Pro Glu Asn Phe Cys Gly
            435             440             445

Met His Phe Phe Asn Pro Val His Arg Met Pro Leu Val Glu Ile Ile
            450             455             460

Arg Gly Glu Lys Ser Ser Asp Glu Thr Ile Ala Lys Val Val Ala Trp
465             470             475             480

Ala Ser Lys Met Gly Lys Thr Pro Ile Val Val Asn Asp Cys Pro Gly
            485             490             495

Phe Phe Val Asn Arg Val Leu Phe Pro Tyr Phe Ala Gly Phe Ser Gln
            500             505             510

Leu Leu Arg Asp Gly Ala Asp Phe Arg Lys Ile Asp Lys Val Met Glu
            515             520             525

Lys Gln Phe Gly Trp Pro Met Gly Pro Ala Tyr Leu Leu Asp Val Val
            530             535             540

Gly Ile Asp Thr Ala His His Ala Gln Ala Val Met Ala Ala Gly Phe
545             550             555             560

Pro Gln Arg Met Gln Lys Asp Tyr Arg Asp Ala Ile Asp Ala Leu Phe
            565             570             575
```

-continued

```
Asp Ala Asn Arg Phe Gly Gln Lys Asn Gly Leu Gly Phe Trp Arg Tyr
        580                 585                 590

Lys Glu Asp Ser Lys Gly Lys Pro Lys Lys Glu Glu Asp Ala Ala Val
        595                 600                 605

Glu Asp Leu Leu Ala Glu Val Ser Gln Pro Lys Arg Asp Phe Ser Glu
        610                 615                 620

Glu Glu Ile Ile Ala Arg Met Met Ile Pro Met Val Asn Glu Val Val
625                 630                 635                 640

Arg Cys Leu Glu Glu Gly Ile Ile Ala Thr Pro Ala Glu Ala Asp Met
                645                 650                 655

Ala Leu Val Tyr Gly Leu Gly Phe Pro Pro Phe His Gly Gly Ala Phe
                660                 665                 670

Arg Trp Leu Asp Thr Leu Gly Ser Ala Lys Tyr Leu Asp Met Ala Gln
        675                 680                 685

Gln Tyr Gln His Leu Gly Pro Leu Tyr Glu Val Pro Glu Gly Leu Arg
        690                 695                 700

Asn Lys Ala Arg His Asn Glu Pro Tyr Tyr Pro Pro Val Glu Pro Ala
705                 710                 715                 720

Arg Pro Val Gly Asp Leu Lys Thr Ala
                725

<210> SEQ ID NO 15
<211> LENGTH: 2148
<212> TYPE: DNA
<213> ORGANISM: Pseudomonas putida

<400> SEQUENCE: 15
atgatttacg aaggtaaagc catcacggtt aaggctcttg aaagtggcat cgtcgagctc      60
aagttcgacc tcaagggtga gtccgtcaac aagttcaacc gccttaccct gaacgagctg     120
cgccaggccg tcgatgccat ccgggccgat gcttcggtca agggcgtgat cgtcaggagt     180
ggcaaggacg tgttcatcgt cggcgccgac atcaccgagt tcgtcgacaa cttcaagctg     240
cctgaggccg aactggtcgc tggcaacctg gaagccaatc gcatcttcaa cgcgttcgaa     300
gacctcgaag tgccgaccgt tgccgccatc aacggcatcg cgctgggcgg cggcctggaa     360
atgtgcctgg cggccgacta ccgggtcatg tccaccagcg ccaggatcgg cctgccggaa     420
gtcaagctgg gtatctaccc gggctttggc ggtaccgtgc cctgccgcg cctgatcggc     480 tcggacaacg ccatcgagtg gatcgccgcc ggcaaggaaa accgtgccga agatgccctg     540
aaagtggggg ccgtcgacgc cgtggtcgcc cctgagctgc tgctggccgg tgccctcgac     600
ctgatcaagc gtgccatcag tggcgagctg gactacaagg ccaagcgcca gccgaagctg     660
gaaaagctca agctcaatgc catcgagcag atgatggcct tcgagactgc caagggcttc     720
gtcgctggcc aggccggccc gaactacccg gccccggtcg aagcgatcaa gagcatccag     780
aaagccgcca acttcggtcg cgacaaggcc ctggaagtcg aagccgcagg ctttgccaag     840
ctggccaaga cctctgtcgc cgagagcctg atcggcttgt cctcaacga tcaggaactc     900 aagcgcaagg ccaaggcgca tgacgagatc gcccacgacg tgaagcaggc cgccgtgctc     960
ggcgccggca tcatgggcgg cggtatcgcc taccagtcgg cggtcaaagg tacgccgatc    1020
ctgatgaagg acatccgcga ggaagccatt cagctgggtc tgaacgaggc ctccaagttg    1080
cttggcaacc gcgtcgagaa gggccgcctg accccggcca agatggccga ggccctcaac    1140
gccattcgcc cgaccctgtc ctatggcgat ttcgccaatg tcgacatcgt cgtcgaggct    1200
```

-continued

```
gtggtcgaga acccgaaggt caagcaagcg gtactggcgg aagtggaagg ccaggtgaag     1260
gacgatgcga tcctcgcttc caacacctct accatctcca tcaacctgct ggccaaggcg     1320
ctcaagcgcc cggaaaactt cgtcggcatg cacttcttca acccggtgca catgatgccg     1380
ctggttgaag tgatccgtgg cgagaagtcc agtgacgtgg cggtcgccac caccgtggcc     1440
tacgccaaga aaatgggcaa gaacccgatc gtggtcaacg actgcccggg cttttttggtc    1500 aaccgcgtgc tgttcccgta ctttggcggt tttgccaagc tggtcagcgc cggtgtcgac     1560
ttcgtgcgca tcgacaaggt catggagaag ttcggctggc cgatgggccc agcctacttg     1620
atggacgtgg tcggcatcga caccggccac cacggccgtg acgtcatggc cgaaggcttc     1680
ccggatcgca tgaaggacga gcgccgctcg gcagtcgacg cgttgtacga ggccaaccgc     1740
ctgggccaga gaacggtaa gggcttctac gcctacgaaa ccgacaagcg cggcaagccg      1800
aagaaggtct tcgatgccac cgtgctcgac gtgctcaaac cgatcgtgtt cgagcagcgt     1860
gaagtcactg acgaagacat catcaactgg atgatggtcc cgctgtgcct tgagaccgtg     1920
cgttgcctgg aagacggcat cgtcgaaacc gctgccgaag ccgacatggg cctggtctac     1980
ggcattggtt tccctccctt ccgcggtggt gcgctgcgtt acatcgactc gatcggtgtg     2040
gccgaattcg tcgccctggc cgatcagtat gccgacctgg ggccgctgta ccacccgacc     2100
gccaagctgc gtgaaatggc caagaacggc cagcgcttct tcaactga               2148
```

```
<210> SEQ ID NO 16
<211> LENGTH: 715
<212> TYPE: PRT
<213> ORGANISM: Pseudomonas putida

<400> SEQUENCE: 16

Met Ile Tyr Glu Gly Lys Ala Ile Thr Val Lys Ala Leu Glu Ser Gly
1               5                   10                  15

Ile Val Glu Leu Lys Phe Asp Leu Lys Gly Glu Ser Val Asn Lys Phe
            20                  25                  30

Asn Arg Leu Thr Leu Asn Glu Leu Arg Gln Ala Val Asp Ala Ile Arg
        35                  40                  45

Ala Asp Ala Ser Val Lys Gly Val Ile Val Arg Ser Gly Lys Asp Val
    50                  55                  60

Phe Ile Val Gly Ala Asp Ile Thr Glu Phe Val Asp Asn Phe Lys Leu
65                  70                  75                  80

Pro Glu Ala Glu Leu Val Ala Gly Asn Leu Glu Ala Asn Arg Ile Phe
                85                  90                  95

Asn Ala Phe Glu Asp Leu Glu Val Pro Thr Val Ala Ala Ile Asn Gly
            100                 105                 110

Ile Ala Leu Gly Gly Gly Leu Glu Met Cys Leu Ala Ala Asp Tyr Arg
        115                 120                 125

Val Met Ser Thr Ser Ala Arg Ile Gly Leu Pro Glu Val Lys Leu Gly
    130                 135                 140

Ile Tyr Pro Gly Phe Gly Gly Thr Val Arg Leu Pro Arg Leu Ile Gly
145                 150                 155                 160

Ser Asp Asn Ala Ile Glu Trp Ile Ala Ala Gly Lys Glu Asn Arg Ala
                165                 170                 175

Glu Asp Ala Leu Lys Val Gly Ala Val Asp Ala Val Val Ala Pro Glu
            180                 185                 190

Leu Leu Leu Ala Gly Ala Leu Asp Leu Ile Lys Arg Ala Ile Ser Gly
        195                 200                 205
```

-continued

```
Glu Leu Asp Tyr Lys Ala Lys Arg Gln Pro Lys Leu Glu Lys Leu Lys
    210             215                 220

Leu Asn Ala Ile Glu Gln Met Met Ala Phe Glu Thr Ala Lys Gly Phe
225             230                 235                 240

Val Ala Gly Gln Ala Gly Pro Asn Tyr Pro Ala Pro Val Glu Ala Ile
                245             250                 255

Lys Ser Ile Gln Lys Ala Ala Asn Phe Gly Arg Asp Lys Ala Leu Glu
                260             265                 270

Val Glu Ala Ala Gly Phe Ala Lys Leu Ala Lys Thr Ser Val Ala Glu
                275             280                 285

Ser Leu Ile Gly Leu Phe Leu Asn Asp Gln Glu Leu Lys Arg Lys Ala
    290             295                 300

Lys Ala His Asp Glu Ile Ala His Asp Val Lys Gln Ala Ala Val Leu
305             310                 315                 320

Gly Ala Gly Ile Met Gly Gly Ile Ala Tyr Gln Ser Ala Val Lys
                325             330                 335

Gly Thr Pro Ile Leu Met Lys Asp Ile Arg Glu Glu Ala Ile Gln Leu
                340             345                 350

Gly Leu Asn Glu Ala Ser Lys Leu Leu Gly Asn Arg Val Glu Lys Gly
    355             360                 365

Arg Leu Thr Pro Ala Lys Met Ala Glu Ala Leu Asn Ala Ile Arg Pro
    370             375                 380

Thr Leu Ser Tyr Gly Asp Phe Ala Asn Val Asp Ile Val Val Glu Ala
385             390                 395                 400

Val Val Glu Asn Pro Lys Val Lys Gln Ala Val Leu Ala Glu Val Glu
                405             410                 415

Gly Gln Val Lys Asp Asp Ala Ile Leu Ala Ser Asn Thr Ser Thr Ile
                420             425                 430

Ser Ile Asn Leu Leu Ala Lys Ala Leu Lys Arg Pro Glu Asn Phe Val
    435             440                 445

Gly Met His Phe Phe Asn Pro Val His Met Met Pro Leu Val Glu Val
    450             455                 460

Ile Arg Gly Glu Lys Ser Ser Asp Val Ala Val Ala Thr Thr Val Ala
465             470                 475                 480

Tyr Ala Lys Lys Met Gly Lys Asn Pro Ile Val Val Asn Asp Cys Pro
                485             490                 495

Gly Phe Leu Val Asn Arg Val Leu Phe Pro Tyr Phe Gly Gly Phe Ala
                500             505                 510

Lys Leu Val Ser Ala Gly Val Asp Phe Val Arg Ile Asp Lys Val Met
                515             520                 525

Glu Lys Phe Gly Trp Pro Met Gly Pro Ala Tyr Leu Met Asp Val Val
    530             535                 540

Gly Ile Asp Thr Gly His His Gly Arg Asp Val Met Ala Glu Gly Phe
545             550                 555                 560

Pro Asp Arg Met Lys Asp Glu Arg Arg Ser Ala Val Asp Ala Leu Tyr
                565             570                 575

Glu Ala Asn Arg Leu Gly Gln Lys Asn Gly Lys Gly Phe Tyr Ala Tyr
                580             585                 590

Glu Thr Asp Lys Arg Gly Lys Pro Lys Lys Val Phe Asp Ala Thr Val
                595             600                 605

Leu Asp Val Leu Lys Pro Ile Val Phe Glu Gln Arg Glu Val Thr Asp
    610             615                 620

Glu Asp Ile Ile Asn Trp Met Met Val Pro Leu Cys Leu Glu Thr Val
```

-continued

```
625              630              635              640

Arg Cys Leu Glu Asp Gly Ile Val Glu Thr Ala Ala Glu Ala Asp Met
            645              650              655

Gly Leu Val Tyr Gly Ile Gly Phe Pro Pro Phe Arg Gly Gly Ala Leu
            660              665              670

Arg Tyr Ile Asp Ser Ile Gly Val Ala Glu Phe Val Ala Leu Ala Asp
        675              680              685

Gln Tyr Ala Asp Leu Gly Pro Leu Tyr His Pro Thr Ala Lys Leu Arg
    690              695              700

Glu Met Ala Lys Asn Gly Gln Arg Phe Phe Asn
705              710              715

<210> SEQ ID NO 17
<211> LENGTH: 2145
<212> TYPE: DNA
<213> ORGANISM: Escherichia coli

<400> SEQUENCE: 17
atggaaatga catcagcgtt taccettaat gttcgtctgg acaacattgc cgttatcacc      60
atcgacgtac cgggtgagaa aatgaatacc ctgaaggcgg agtttgcctc gcaggtgcgc     120
gccattatta agcaactccg tgaaaacaaa gagttgcgag gcgtggtgtt tgtctccgct     180
aaaccggaca acttcattgc tggcgcagac atcaacatga tcggcaactg caaaacggcg     240
caagaagcgg aagctctggc gcggcagggc caacagttga tggcggagat tcatgctttg     300
cccattcagg ttatcgcggc tattcatggc gcttgcctgg tggtggggct ggagttggcg     360
ctggcgtgcc acggtcgcgt ttgtactgac gatcctaaaa cggtgctcgg tttgcctgaa     420
gtacaacttg gattgttacc cggttcaggc ggcacccagc gtttaccgcg tctgataggc     480
gtcagcacag cattagagat gatcctcacc ggaaaacaac ttcgggcgaa acaggcatta     540
aagctggggc tggtggatga cgttgttccg cactccattc tgctggaagc cgctgttgag     600
ctggcaaaga aggagcgccc atcttcccgc cctctacctg tacgcgagcg tattctggcg     660
gggccgttag gtcgtgcgct gctgttcaaa atggtcggca agaaaacaga acacaaaact     720
caaggcaatt atccggcgac agaacgcatc ctggaggttg ttgaaacggg attagcgcag     780
ggcaccagca gcggttatga cgccgaagct cgggcgtttg gcgaactggc gatgacgcca     840
caatcgcagg cgctgcgtag tatctttttt gccagtacgg acgtgaagaa agatcccggc     900
agtgatgcgc cgcctgcgcc attaaacagc gtggggattt aggtggtgg cttgatgggc     960 ggcggtattg cttatgtcac tgcttgtaaa gcggggattc cggtcagaat aaaagatatc    1020
aacccgcagg gcataaatca tgcgctgaag tacagttggg atcagctgga gggcaaagtt    1080
cgccgtcgtc atctcaaagc cagcgaacgt gacaaacagc tggcattaat ctccggaacg    1140
acggactatc gcggctttgc ccatcgcgat ctgattattg aagcggtgtt tgaaaatctc    1200
gaattgaaac aacagatggt ggcggaagtt gagcaaaatt gcgccgctca taccatcttt    1260
gcttcgaata cgtcatcttt accgattggt gatatcgccg ctcacgccac gcgacctgag    1320
caagttatcg gcctgcattt cttcagtccg gtggaaaaaa tgccgctggt ggagattatt    1380
cctcatgcgg ggacatcggc gcaaaccatc gctaccacag taaaactggc gaaaaaacag    1440
ggtaaaacgc caattgtcgt gcgtgacaaa gccggttttt acgtcaatcg catcttagcg    1500
ccttacatta tgaagctat ccgcatgttg acccaaggtg aacgggtaga gcacattgat    1560
gccgcgctag tgaaatttgg ttttccggta ggcccaatcc aacttttgga tgaggtagga    1620
```

-continued

```
atcgacaccg ggactaaaat tattcctgta ctggaagccg cttatggaga acgttttagc    1680
gcgcctgcaa atgttgtttc ttcaattttg aacgacgatc gcaaaggcag aaaaaatggc    1740
cggggtttct atctttatgg tcagaaaggg cgtaaaagca aaaaacaggt cgatcccgcc    1800
atttacccgc tgattggcac acaagggcag gggcgaatct ccgcaccgca ggttgctgaa    1860
cggtgtgtga tgttgatgct gaatgaagca gtacgttgtg ttgatgagca ggttatccgt    1920
agcgtgcgtg acggggatat tggcgcggta tttggcattg gttttccgcc atttctcggt    1980
ggaccgttcc gctatatcga ttctctcggc gcgggcgaag tggttgcaat aatgcaacga    2040
cttgccacgc agtatggttc ccgtttacc ccttgcgagc gtttggtcga gatgggcgcg    2100 cgtgggggaaa gttttttggaa aacaactgca actgacctgc aataa            2145
```

<210> SEQ ID NO 18
<211> LENGTH: 714
<212> TYPE: PRT
<213> ORGANISM: Escherichia coli

<400> SEQUENCE: 18

```
Met Glu Met Thr Ser Ala Phe Thr Leu Asn Val Arg Leu Asp Asn Ile
1               5                   10                  15

Ala Val Ile Thr Ile Asp Val Pro Gly Glu Lys Met Asn Thr Leu Lys
            20                  25                  30

Ala Glu Phe Ala Ser Gln Val Arg Ala Ile Ile Lys Gln Leu Arg Glu
        35                  40                  45

Asn Lys Glu Leu Arg Gly Val Val Phe Val Ser Ala Lys Pro Asp Asn
    50                  55                  60

Phe Ile Ala Gly Ala Asp Ile Asn Met Ile Gly Asn Cys Lys Thr Ala
65                  70                  75                  80

Gln Glu Ala Glu Ala Leu Ala Arg Gln Gly Gln Gln Leu Met Ala Glu
                85                  90                  95

Ile His Ala Leu Pro Ile Gln Val Ile Ala Ala Ile His Gly Ala Cys
            100                 105                 110

Leu Gly Gly Gly Leu Glu Leu Ala Leu Ala Cys His Gly Arg Val Cys
        115                 120                 125

Thr Asp Asp Pro Lys Thr Val Leu Gly Leu Pro Glu Val Gln Leu Gly
        130                 135                 140

Leu Leu Pro Gly Ser Gly Gly Thr Gln Arg Leu Pro Arg Leu Ile Gly
145                 150                 155                 160

Val Ser Thr Ala Leu Glu Met Ile Leu Thr Gly Lys Gln Leu Arg Ala
                165                 170                 175

Lys Gln Ala Leu Lys Leu Gly Leu Val Asp Asp Val Val Pro His Ser
            180                 185                 190

Ile Leu Leu Glu Ala Ala Val Glu Leu Ala Lys Lys Glu Arg Pro Ser
            195                 200                 205

Ser Arg Pro Leu Pro Val Arg Glu Arg Ile Leu Ala Gly Pro Leu Gly
        210                 215                 220

Arg Ala Leu Leu Phe Lys Met Val Gly Lys Lys Thr Glu His Lys Thr
225                 230                 235                 240

Gln Gly Asn Tyr Pro Ala Thr Glu Arg Ile Leu Glu Val Val Glu Thr
                245                 250                 255

Gly Leu Ala Gln Gly Thr Ser Ser Gly Tyr Asp Ala Glu Ala Arg Ala
            260                 265                 270

Phe Gly Glu Leu Ala Met Thr Pro Gln Ser Gln Ala Leu Arg Ser Ile
            275                 280                 285
```

-continued

```
Phe Phe Ala Ser Thr Asp Val Lys Lys Asp Pro Gly Ser Asp Ala Pro
    290                 295             300

Pro Ala Pro Leu Asn Ser Val Gly Ile Leu Gly Gly Gly Leu Met Gly
305             310             315                 320

Gly Gly Ile Ala Tyr Val Thr Ala Cys Lys Ala Gly Ile Pro Val Arg
            325             330             335

Ile Lys Asp Ile Asn Pro Gln Gly Ile Asn His Ala Leu Lys Tyr Ser
            340             345             350

Trp Asp Gln Leu Glu Gly Lys Val Arg Arg Arg His Leu Lys Ala Ser
            355             360             365

Glu Arg Asp Lys Gln Leu Ala Leu Ile Ser Gly Thr Thr Asp Tyr Arg
    370             375             380

Gly Phe Ala His Arg Asp Leu Ile Ile Glu Ala Val Phe Glu Asn Leu
385             390             395                 400

Glu Leu Lys Gln Gln Met Val Ala Glu Val Glu Gln Asn Cys Ala Ala
            405             410             415

His Thr Ile Phe Ala Ser Asn Thr Ser Ser Leu Pro Ile Gly Asp Ile
            420             425             430

Ala Ala His Ala Thr Arg Pro Glu Gln Val Ile Gly Leu His Phe Phe
            435             440             445

Ser Pro Val Glu Lys Met Pro Leu Val Glu Ile Ile Pro His Ala Gly
    450             455             460

Thr Ser Ala Gln Thr Ile Ala Thr Thr Val Lys Leu Ala Lys Lys Gln
465             470             475                 480

Gly Lys Thr Pro Ile Val Val Arg Asp Lys Ala Gly Phe Tyr Val Asn
            485             490             495

Arg Ile Leu Ala Pro Tyr Ile Asn Glu Ala Ile Arg Met Leu Thr Gln
            500             505             510

Gly Glu Arg Val Glu His Ile Asp Ala Ala Leu Val Lys Phe Gly Phe
            515             520             525

Pro Val Gly Pro Ile Gln Leu Leu Asp Glu Val Gly Ile Asp Thr Gly
    530             535             540

Thr Lys Ile Ile Pro Val Leu Glu Ala Ala Tyr Gly Glu Arg Phe Ser
545             550             555                 560

Ala Pro Ala Asn Val Val Ser Ser Ile Leu Asn Asp Asp Arg Lys Gly
            565             570             575

Arg Lys Asn Gly Arg Gly Phe Tyr Leu Tyr Gly Gln Lys Gly Arg Lys
            580             585             590

Ser Lys Lys Gln Val Asp Pro Ala Ile Tyr Pro Leu Ile Gly Thr Gln
    595             600             605

Gly Gln Gly Arg Ile Ser Ala Pro Gln Val Ala Glu Arg Cys Val Met
    610             615             620

Leu Met Leu Asn Glu Ala Val Arg Cys Val Asp Glu Gln Val Ile Arg
625             630             635                 640

Ser Val Arg Asp Gly Asp Ile Gly Ala Val Phe Gly Ile Gly Phe Pro
            645             650             655

Pro Phe Leu Gly Gly Pro Phe Arg Tyr Ile Asp Ser Leu Gly Ala Gly
            660             665             670

Glu Val Val Ala Ile Met Gln Arg Leu Ala Thr Gln Tyr Gly Ser Arg
            675             680             685

Phe Thr Pro Cys Glu Arg Leu Val Glu Met Gly Ala Arg Gly Glu Ser
    690             695             700
```

-continued

```
Phe Trp Lys Thr Thr Ala Thr Asp Leu Gln
705                 710

<210> SEQ ID NO 19
<211> LENGTH: 1164
<212> TYPE: DNA
<213> ORGANISM: Escherichia coli

<400> SEQUENCE: 19
atggaacagg ttgtcattgt cgatgcaatt cgcaccccga tgggccgttc gaagggcggt      60 gctttcgta acgtgcgtgc agaagatctc tccgctcatt taatgcgtag cctgctggcg     120
cgtaacccgg cgctggaagc ggcggccctc gacgatattt actggggttg tgtgcagcag     180
acgctggagc agggttttaa tatcgcccgt aacgcggcgc tgctggcaga agtaccacac     240
tctgtcccgg cggttaccgt taatcgcttg tgtggttcat ccatgcaggc actgcatgac     300
gcagcacgaa tgatcatgac tggcgatgcg caggcatgtc tggttggcgg cgtggagcat     360
atgggccatg tgccgatgag tcacggcgtc gattttcacc ccggcctgag ccgcaatgtc     420
gccaaagcgg cgggcatgat gggcttaacg gcagaaatgc tggcgcgtat gcacggtatc     480
agccgtgaaa tgcaggatgc ctttgccgcg cggtcacacg cccgcgcctg ggccgccacg     540
cagtcggccg catttaaaaa tgaaatcatc ccgaccggtg gtcacgatgc cgacggcgtc     600
ctgaagcagt ttaattacga cgaagtgatt cgcccggaaa ccaccgtgga gccctcgcc     660 acgctgcgtc cggcgtttga tccagtaaac ggtatggtaa cggcgggcac atcttctgca     720
ctttccgatg gcgcagctgc catgctggtg atgagtgaaa gccgcgccca tgaattaggt     780
cttaagccgc gcgctcgtgt gcgttcgatg gcggtcgttg gttgtgaccc atcgattatg     840
ggttacggcc cggttccggc ctcgaaactg gcgctgaaaa agcgggggct ttctgccagc     900
gatatcggcg tgtttgaaat gaacgaagcc tttgccgcgc agatcctgcc atgtattaaa     960
gatctgggac taattgagca gattgacgag aagatcaacc tcaacggtgg cgcgatcgcg    1020
ctgggtcatc cgctgggttg ttccggtgcg cgtatcagca ccacgctgct gaatctgatg    1080
gaacgcaaag acgttcagtt tggtctggcg acgatgtgta tcggtctggg tcagggtatt    1140
gcgacggtgt ttgagcgggt ttaa                                           1164

<210> SEQ ID NO 20
<211> LENGTH: 387
<212> TYPE: PRT
<213> ORGANISM: Escherichia coli

<400> SEQUENCE: 20

Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Glu Ala Ala
        35                  40                  45

Ala Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Val Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Ala
            100                 105                 110
```

-continued

```
Cys Leu Val Gly Gly Val Glu His Met Gly His Val Pro Met Ser His
        115                 120                 125

Gly Val Asp Phe His Pro Gly Leu Ser Arg Asn Val Ala Lys Ala Ala
    130                 135                 140

Gly Met Met Gly Leu Thr Ala Glu Met Leu Ala Arg Met His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Ala Ala Phe Lys Asn Glu Ile Ile Pro Thr
            180                 185                 190

Gly Gly His Asp Ala Asp Gly Val Leu Lys Gln Phe Asn Tyr Asp Glu
        195                 200                 205

Val Ile Arg Pro Glu Thr Thr Val Glu Ala Leu Ala Thr Leu Arg Pro
    210                 215                 220

Ala Phe Asp Pro Val Asn Gly Met Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

His Glu Leu Gly Leu Lys Pro Arg Ala Arg Val Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Lys Ala Gly Leu Ser Ala Ser Asp Ile Gly Val
    290                 295                 300

Phe Glu Met Asn Glu Ala Phe Ala Ala Gln Ile Leu Pro Cys Ile Lys
305                 310                 315                 320

Asp Leu Gly Leu Ile Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
        355                 360                 365

Leu Ala Thr Met Cys Ile Gly Leu Gly Gln Gly Ile Ala Thr Val Phe
    370                 375                 380

Glu Arg Val
385
```

<210> SEQ ID NO 21
<211> LENGTH: 1182
<212> TYPE: DNA
<213> ORGANISM: Ralstonia eutropha

<400> SEQUENCE: 21

```
atgacccgcg aagttgtagt ggtatccggc gtccgtactg ccattgggac attcggtggt      60
tctttgaaag atgtcgcccc ggctgaactt ggagccttag tggtccgcga agctctggct     120
cgcgcacaag tgagtggtga cgacgtaggt catgtggtgt tcggcaacgt catccaaacc     180
gagcctcgtg atatgtattt aggtcgtgtg gccgcggtta atggcggcgt gacgatcaac     240
gctccggctc ttactgttaa ccgtctttgt ggttcaggcc tgcaagcaat tgttagtgcg     300
gcgcagacca tccttctggg agatacggac gtagccattg tggtggggc agagagtatg      360 agccgtgcac cttaccttgc tcctgctgcc cgctggggag cacgcatggg ggatgctgga     420
cttgtagata tgatgcttgg tgctttgcat gatcctttcc accgcattca catgggcgtg     480
```

-continued

```
accgcggaga atgtagcgaa ggagtatgac atctcacgtg ctcagcagga tgaggcagca      540
ttggaatctc accgccgtgc gagcgccgct attaaggctg ggtacttcaa agatcagatc      600
gttccagtcg taagcaaggg tcgtaagggg gatgtaacgt ttgatacaga tgagcacgta      660
cgtcacgatg ccactatcga tgatatgacg aaacttcgtc ccgttttcgt taaggagaat      720
ggaaccgtca ctgcaggtaa tgcatcagga ttaaacgacg cggcagcagc cgttgttatg      780
atggaacgtg cggaggcgga acgccgtggt ttaaagcctc tggcccgtct ggtcagttat      840
ggccacgcag gagtggaccc gaaagcgatg ggaattggtc ctgtgccggc aacgaagatt      900
gctttagagc gtgcgggact tcaagtaagc gaccttgacg tgatcgaagc aaatgaggct      960
tttgcggcgc aggcttgcgc ggtaacaaaa gcgttgggac tggatcccgc caaggtcaac     1020
cccaacggtt cgggcatctc attaggacac ccaatcggag ctacgggggc cttaattaca     1080
gtcaaggcac ttcacgaatt aaatcgtgtg caggggcgct acgcgttggt cacaatgtgc     1140
attggaggtg gccagggtat tgctgctatc ttcgaacgta tc                       1182
```

<210> SEQ ID NO 22
<211> LENGTH: 394
<212> TYPE: PRT
<213> ORGANISM: Ralstonia eutropha

<400> SEQUENCE: 22

```
Met Thr Arg Glu Val Val Val Val Ser Gly Val Arg Thr Ala Ile Gly
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Ala Val Asn Gly Gly Val Thr Ile Asn
65                  70                  75                  80

Ala Pro Ala Leu Thr Val Asn Arg Leu Cys Gly Ser Gly Leu Gln Ala
            85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
        115                 120                 125

Ala Ala Arg Trp Gly Ala Arg Met Gly Asp Ala Gly Leu Val Asp Met
        130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
        195                 200                 205

Lys Gly Asp Val Thr Phe Asp Thr Asp Glu His Val Arg His Asp Ala
    210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255
```

-continued

```
Ala Val Val Met Met Glu Arg Ala Glu Ala Glu Arg Arg Gly Leu Lys
        260                 265                 270

Pro Leu Ala Arg Leu Val Ser Tyr Gly His Ala Gly Val Asp Pro Lys
        275                 280                 285

Ala Met Gly Ile Gly Pro Val Pro Ala Thr Lys Ile Ala Leu Glu Arg
        290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
                325                 330                 335

Ala Lys Val Asn Pro Asn Gly Ser Gly Ile Ser Leu Gly His Pro Ile
        340                 345                 350

Gly Ala Thr Gly Ala Leu Ile Thr Val Lys Ala Leu His Glu Leu Asn
        355                 360                 365

Arg Val Gln Gly Arg Tyr Ala Leu Val Thr Met Cys Ile Gly Gly Gly
        370                 375                 380

Gln Gly Ile Ala Ala Ile Phe Glu Arg Ile
385                 390
```

<210> SEQ ID NO 23
<211> LENGTH: 1164
<212> TYPE: DNA
<213> ORGANISM: Salmonella enterica

<400> SEQUENCE: 23

```
atggaacagg ttgtcattgt cgatgctatt cgcaccccga tgggccgttc gaagggcggc        60
gcgtttcgca acgtgcgagc agaagatctc tccgcccact taatgcgtag cctgctggcg       120
cgtaatccgt cgcttacagc ggcgaccctc gatgatattt actggggctg cgtacaacaa       180
acgctggagc aaggcttcaa cattgcccgt aacgccgcgc tgctggcaga aattccccat       240
tcggtaccgg cggtcaccgt caaccgtctg tgtggttcct cgatgcaggc gttacacgat       300
gcagcgcgaa tgatcatgac cggcgatgcg caggtttgtc tggttggcgg cgtggagcat       360
atggggcacg tgccgatgag ccacggcgtg gattttcacc cgggtctgag tcgcaacgtc       420
gccaaagcgg cagggatgat ggggctaacg gcggaaatgc tctcccgcct gcacggcatt       480
agccgggaaa tgcaggacca gttcgccgcg cgttctcacg ctcgcgcctg ggccgccacc       540
cagtctggcg cattcaaaac ggagattatc ccgactggcg gtcatgatgc agacggcgtg       600
ttgaagcagt ttaactacga tgaagtgatc cgcccggaaa ccacggtcga gcgctatca        660 acgctgcgtc cggcatttga tccggttagt ggcacggtca cggcgggcac ctcatccgcg       720
ctttccgatg gcgcagccgc catgctggta atgagcgaaa gtcgtgcccg tgagctgggt       780
ctgaaacctc gcgcccgtat tcgctcaatg gcagtggtgg gttgtgatcc gtcaattatg       840
ggttacgggc cggttccggc gtcaaaactg gcgttgaaaa aagcgggact gtcagccagc       900
gatatcgatg tgtttgagat gaacgaagcg tttgccgcac agatcctgcc atgcattaag       960
gatctgggat tgatggagca gatagacgag aagatcaacc tcaacggcgg tgcgatcgcg      1020
cttggtcatc cgctcggctg ctccggagca cgtatcagca ccacgcttat caacctgatg      1080
gagcgcaaag acgcgcagtt tggtctggcg acgatgtgta ttggtctggg tcagggcatc      1140
gccacggtgt ttgagcgggt ttaa                                             1164
```

<210> SEQ ID NO 24
<211> LENGTH: 387

<212> TYPE: PRT
<213> ORGANISM: Salmonella enterica

<400> SEQUENCE: 24

```
Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ser Leu Thr Ala Ala
        35                  40                  45

Thr Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Ile Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Val
            100                 105                 110

Cys Leu Val Gly Gly Val Glu His Met Gly His Val Pro Met Ser His
            115                 120                 125

Gly Val Asp Phe His Pro Gly Leu Ser Arg Asn Val Ala Lys Ala Ala
            130                 135                 140

Gly Met Met Gly Leu Thr Ala Glu Met Leu Ser Arg Leu His Gly Ile
145                 150                 155                 160

Ser Arg Glu Met Gln Asp Gln Phe Ala Ala Arg Ser His Ala Arg Ala
                165                 170                 175

Trp Ala Ala Thr Gln Ser Gly Ala Phe Lys Thr Glu Ile Ile Pro Thr
            180                 185                 190

Gly Gly His Asp Ala Asp Gly Val Leu Lys Gln Phe Asn Tyr Asp Glu
            195                 200                 205

Val Ile Arg Pro Glu Thr Thr Val Glu Ala Leu Ser Thr Leu Arg Pro
    210                 215                 220

Ala Phe Asp Pro Val Ser Gly Thr Val Thr Ala Gly Thr Ser Ser Ala
225                 230                 235                 240

Leu Ser Asp Gly Ala Ala Ala Met Leu Val Met Ser Glu Ser Arg Ala
            245                 250                 255

Arg Glu Leu Gly Leu Lys Pro Arg Ala Arg Ile Arg Ser Met Ala Val
            260                 265                 270

Val Gly Cys Asp Pro Ser Ile Met Gly Tyr Gly Pro Val Pro Ala Ser
            275                 280                 285

Lys Leu Ala Leu Lys Lys Ala Gly Leu Ser Ala Ser Asp Ile Asp Val
    290                 295                 300

Phe Glu Met Asn Glu Ala Phe Ala Ala Gln Ile Leu Pro Cys Ile Lys
305                 310                 315                 320

Asp Leu Gly Leu Met Glu Gln Ile Asp Glu Lys Ile Asn Leu Asn Gly
            325                 330                 335

Gly Ala Ile Ala Leu Gly His Pro Leu Gly Cys Ser Gly Ala Arg Ile
            340                 345                 350

Ser Thr Thr Leu Ile Asn Leu Met Glu Arg Lys Asp Ala Gln Phe Gly
            355                 360                 365

Leu Ala Thr Met Cys Ile Gly Leu Gly Gln Gly Ile Ala Thr Val Phe
    370                 375                 380

Glu Arg Val
385
```

```
<210> SEQ ID NO 25
<211> LENGTH: 1311
<212> TYPE: DNA
<213> ORGANISM: Escherichia coli

<400> SEQUENCE: 25
atgggtcagg ttttaccgct ggttacccgc cagggcgatc gtatcgccat tgttagcggt      60
ttacgtacgc cttttgcccg tcaggcgacg gcttttcatg gcattcccgc ggttgattta     120
gggaagatgg tggtaggcga actgctggca cgcagcgaga tccccgccga agtgattgaa     180
caactggtct ttggtcaggt cgtacaaatg cctgaagccc ccaacattgc gcgtgaaatt     240
gttctcggta cgggaatgaa tgtacatacc gatgcttaca gcgtcagccg cgcttgcgct     300
accagtttcc aggcagttgc aaacgtcgca gaaagcctga tggcgggaac tattcgagcg     360
gggattgccg gtggggcaga ttcctcttcg gtattgccaa ttggcgtcag taaaaaactg     420
gcgcgcgtgc tggttgatgt caacaaagct cgtaccatga ccagcgact gaaactcttc     480 tctcgcctgc gtttgcgcga cttaatgccc gtaccacctg cggtagcaga atattctacc     540
ggcttgcgga tgggcgacac cgcagagcaa atggcgaaaa cctacggcat caccgagaa     600 cagcaagatg cattagcgca ccgttcgcat cagcgtgccg ctcaggcatg gtcagacgga     660
aaactcaaag aagaggtgat gactgccttt atccctcctt ataaacaacc gcttgtcgaa     720
gacaacaata ttcgcggtaa ttcctcgctt gccgattacg caaagctgcg cccggcgttt     780
gatcgcaaac acggaacggt aacggcggca aacagtacgc cgctgaccga tggcgcggca     840
gcggtgatcc tgatgactga atcccgggcg aaagaattag gctggtgcc gctggggtat     900 ctgcgcagct acgcatttac tgcgattgat gtctggcagg acatgttgct cggtccagcc     960
tggtcaacac cgctggcgct ggagcgtgcc ggtttgacga tgagcgatct gacattgatc    1020
gatatgcacg aagcctttgc agctcagacg ctggcgaata ttcagttgct gggtagtgaa    1080
cgttttgctc gtgaagcact ggggcgtgca catgccactg gcgaagtgga cgatagcaaa    1140
tttaacgtgc ttggcggttc gattgcttac gggcatccct tcgcggcgac cggcgcgcgg    1200
atgattaccc agacattgca tgaacttcgc cgtcgcggcg tggatttggg tttagttacc    1260
gcctgtgctg ccggtgggct tggcgcggca atggttctgg aggcggaata a            1311

<210> SEQ ID NO 26
<211> LENGTH: 436
<212> TYPE: PRT
<213> ORGANISM: Escherichia coli

<400> SEQUENCE: 26

Met Gly Gln Val Leu Pro Leu Val Thr Arg Gln Gly Asp Arg Ile Ala
1               5                   10                  15

Ile Val Ser Gly Leu Arg Thr Pro Phe Ala Arg Gln Ala Thr Ala Phe
            20                  25                  30

His Gly Ile Pro Ala Val Asp Leu Gly Lys Met Val Val Gly Glu Leu
        35                  40                  45

Leu Ala Arg Ser Glu Ile Pro Ala Glu Val Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Asn Val His Thr Asp Ala Tyr Ser Val Ser
                85                  90                  95
```

```
Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Gly Ala Asp Ser
            115                 120                 125

Ser Ser Val Leu Pro Ile Gly Val Ser Lys Lys Leu Ala Arg Val Leu
            130                 135                 140

Val Asp Val Asn Lys Ala Arg Thr Met Ser Gln Arg Leu Lys Leu Phe
145                 150                 155                 160

Ser Arg Leu Arg Leu Arg Asp Leu Met Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
            195                 200                 205

Ser His Gln Arg Ala Ala Gln Ala Trp Ser Asp Gly Lys Leu Lys Glu
            210                 215                 220

Glu Val Met Thr Ala Phe Ile Pro Pro Tyr Lys Gln Pro Leu Val Glu
225                 230                 235                 240

Asp Asn Asn Ile Arg Gly Asn Ser Ser Leu Ala Asp Tyr Ala Lys Leu
                245                 250                 255

Arg Pro Ala Phe Asp Arg Lys His Gly Thr Val Thr Ala Ala Asn Ser
            260                 265                 270

Thr Pro Leu Thr Asp Gly Ala Ala Ala Val Ile Leu Met Thr Glu Ser
            275                 280                 285

Arg Ala Lys Glu Leu Gly Leu Val Pro Leu Gly Tyr Leu Arg Ser Tyr
            290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Met Ser Asp
                325                 330                 335

Leu Thr Leu Ile Asp Met His Glu Ala Phe Ala Ala Gln Thr Leu Ala
            340                 345                 350

Asn Ile Gln Leu Leu Gly Ser Glu Arg Phe Ala Arg Glu Ala Leu Gly
            355                 360                 365

Arg Ala His Ala Thr Gly Glu Val Asp Asp Ser Lys Phe Asn Val Leu
            370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Arg Arg Arg Gly Gly Gly Phe
                405                 410                 415

Gly Leu Val Thr Ala Cys Ala Ala Gly Gly Leu Gly Ala Ala Met Val
                420                 425                 430

Leu Glu Ala Glu
            435
```

```
<210> SEQ ID NO 27
<211> LENGTH: 2445
<212> TYPE: DNA
<213> ORGANISM: Escherichia coli

<400> SEQUENCE: 27
atgatgattt tgagtattct cgctacggtt gtcctgctcg gcgcgttgtt ctatcaccgc        60
gtgagcttat ttatcagcag tctgattttg ctcgcctgga cagccgccct cggcgttgct       120
ggtctgtggt cggcgtgggt actggtgcct ctggccatta tcctcgtgcc atttaacttt       180
```

-continued

```
gcgcctatgc gtaagtcgat gatttccgcg ccggtatttc gcggtttccg taaggtgatg      240
ccgccgatgt cgcgcactga gaaagaagcg attgatgcgg gcaccacctg gtgggagggc      300
gacttgttcc agggcaagcc ggactggaaa aagctgcata actatccgca gccgcgcctg      360
accgccgaag agcaagcgtt tctcgacggc ccggtagaag aagcctgccg gatggcgaat      420
gatttccaga tcacccatga gctggcggat ctgccgccgg agttgtgggc gtaccttaaa      480
gagcatcgtt tcttcgcgat gatcatcaaa aaagagtacg gcgggctgga gttctcggct      540
tatgcccagt ctcgcgtgct gcaaaaactc tccggcgtga gcgggatcct ggcgattacc      600
gtcggcgtgc caaactcatt aggcccgggc gaactgttgc aacattacgg cactgacgag      660
cagaaagatc actatctgcc gcgtctggcg cgtggtcagg agatcccctg ctttgcactg      720
accagcccgg aagcgggttc cgatgcgggc gcgattccgg acaccgggat tgtctgcatg      780
ggcgaatggc agggccagca ggtgctgggg atgcgtctga cctggaacaa acgctacatt      840
acgctggcac cgattgcgac cgtgcttggg ctggcgttta aactctccga cccggaaaaa      900
ttactcggcg gtgcagaaga tttaggcatt acctgtgcgc tgatcccaac caccacgccg      960
ggcgtggaaa ttggtcgtcg ccacttcccg ctgaacgtac cgttccagaa cggaccgacg     1020
cgcggtaaag atgtcttcgt gccgatcgat tacatcatcg gcgggccgaa aatggccggg     1080
caaggctggc ggatgctggt ggagtgcctc tcggtaggcc gcggcatcac cctgccttcc     1140
aactcaaccg gcggcgtgaa atcggtagcg ctggcaaccg gcgcgtatgc tcacattcgc     1200
cgtcagttca aaatctctat tggtaagatg gaagggattg aagagccgct ggcgcgtatt     1260
gccggtaatg cctacgtgat ggatgctgcg gcatcgctga ttacctacgg cattatgctc     1320
ggcgaaaaac ctgccgtgct gtcggctatc gttaagtatc actgtaccca ccgcgggcag     1380
cagtcgatta ttgatgcgat ggatattacc ggcggtaaag gcattatgct cgggcaaagc     1440
aacttcctgg cgcgtgctta ccagggcgca ccgattgcca tcaccgttga aggggctaac     1500
attctgaccc gcagcatgat gatcttcgga caaggagcga ttcgttgcca tccgtacgtg     1560
ctggaagaga tggaagcggc gaagaacaat gacgtcaacg cgttcgataa actgttgttc     1620
aaacatatcg gtcacgtcgg tagcaacaaa gttcgcagct tctggctggg cctgacgcgc     1680
ggtttaacca gcagcacgcc aaccggcgat gccactaaac gctactatca gcacctgaac     1740
cgcctgagcg ccaacctcgc cctgcttttct gatgtctcga tggcagtgct gggcggcagc     1800
ctgaaacgtc gcgagcgcat ctcggcccgt ctgggggata ttttaagcca gctctacctc     1860
gcctctgccg tgctgaagcg ttatgacgac gaaggccgta tgaagccga cctgccgctg      1920 gtgcactggg gcgtacaaga tgcgctgtat caggctgaac aggcgatgga tgatttactg     1980
caaaacttcc cgaaccgcgt ggttgccggg ctgctgaatg tggtgatctt cccgaccgga     2040
cgtcattatc tggcaccttc tgacaagctg gatcataaag tggcgaagat tttacaagtg     2100
ccgaacgcca cccgttcccg cattggtcgc ggtcagtacc tgacgccgag cgagcataat     2160
ccggttggct tgctggaaga ggcgctggtg gatgtgattg ccgccgaccc aattcatcag     2220
cggatctgta aagagctggg taaaaacctg ccgtttaccc gtctggatga actggcgcac     2280
aacgcgctgg tgaagggggct gattgataaa gatgaagccg ctattctggt gaaagctgaa     2340
gaaagccgtc tgcgcagtat taacgttgat gactttgatc cggaagagct ggcgacgaag     2400
ccggtaaagt gccggagaa agtgcggaaa gttgaagccg cgtaa                      2445
```

<210> SEQ ID NO 28

```
<211> LENGTH: 814
<212> TYPE: PRT
<213> ORGANISM: Escherichia coli

<400> SEQUENCE: 28

Met Met Ile Leu Ser Ile Leu Ala Thr Val Val Leu Leu Gly Ala Leu
1               5                   10                  15

Phe Tyr His Arg Val Ser Leu Phe Ile Ser Ser Leu Ile Leu Leu Ala
                20                  25                  30

Trp Thr Ala Ala Leu Gly Val Ala Gly Leu Trp Ser Ala Trp Val Leu
            35                  40                  45

Val Pro Leu Ala Ile Ile Leu Val Pro Phe Asn Phe Ala Pro Met Arg
        50                  55                  60

Lys Ser Met Ile Ser Ala Pro Val Phe Arg Gly Phe Arg Lys Val Met
65                  70                  75                  80

Pro Pro Met Ser Arg Thr Glu Lys Glu Ala Ile Asp Ala Gly Thr Thr
                85                  90                  95

Trp Trp Glu Gly Asp Leu Phe Gln Gly Lys Pro Asp Trp Lys Lys Leu
                100                 105                 110

His Asn Tyr Pro Gln Pro Arg Leu Thr Ala Glu Glu Gln Ala Phe Leu
            115                 120                 125

Asp Gly Pro Val Glu Glu Ala Cys Arg Met Ala Asn Asp Phe Gln Ile
        130                 135                 140

Thr His Glu Leu Ala Asp Leu Pro Pro Glu Leu Trp Ala Tyr Leu Lys
145                 150                 155                 160

Glu His Arg Phe Phe Ala Met Ile Ile Lys Lys Glu Tyr Gly Gly Leu
                165                 170                 175

Glu Phe Ser Ala Tyr Ala Gln Ser Arg Val Leu Gln Lys Leu Ser Gly
            180                 185                 190

Val Ser Gly Ile Leu Ala Ile Thr Val Gly Val Pro Asn Ser Leu Gly
        195                 200                 205

Pro Gly Glu Leu Leu Gln His Tyr Gly Thr Asp Glu Gln Lys Asp His
        210                 215                 220

Tyr Leu Pro Arg Leu Ala Arg Gly Gln Glu Ile Pro Cys Phe Ala Leu
225                 230                 235                 240

Thr Ser Pro Glu Ala Gly Ser Asp Ala Gly Ala Ile Pro Asp Thr Gly
            245                 250                 255

Ile Val Cys Met Gly Glu Trp Gln Gly Gln Gln Val Leu Gly Met Arg
            260                 265                 270

Leu Thr Trp Asn Lys Arg Tyr Ile Thr Leu Ala Pro Ile Ala Thr Val
            275                 280                 285

Leu Gly Leu Ala Phe Lys Leu Ser Asp Pro Glu Lys Leu Leu Gly Gly
        290                 295                 300

Ala Glu Asp Leu Gly Ile Thr Cys Ala Leu Ile Pro Thr Thr Thr Pro
305                 310                 315                 320

Gly Val Glu Ile Gly Arg Arg His Phe Pro Leu Asn Val Pro Phe Gln
                325                 330                 335

Asn Gly Pro Thr Arg Gly Lys Asp Val Phe Val Pro Ile Asp Tyr Ile
            340                 345                 350

Ile Gly Gly Pro Lys Met Ala Gly Gln Gly Trp Arg Met Leu Val Glu
            355                 360                 365

Cys Leu Ser Val Gly Arg Gly Ile Thr Leu Pro Ser Asn Ser Thr Gly
    370                 375                 380

Gly Val Lys Ser Val Ala Leu Ala Thr Gly Ala Tyr Ala His Ile Arg
```

-continued

```
                385                 390                 395                 400

Arg Gln Phe Lys Ile Ser Ile Gly Lys Met Glu Gly Ile Glu Glu Pro
                405                 410                 415

Leu Ala Arg Ile Ala Gly Asn Ala Tyr Val Met Asp Ala Ala Ala Ser
                420                 425                 430

Leu Ile Thr Tyr Gly Ile Met Leu Gly Glu Lys Pro Ala Val Leu Ser
                435                 440                 445

Ala Ile Val Lys Tyr His Cys Thr His Arg Gly Gln Gln Ser Ile Ile
                450                 455                 460

Asp Ala Met Asp Ile Thr Gly Gly Lys Gly Ile Met Leu Gly Gln Ser
465                 470                 475                 480

Asn Phe Leu Ala Arg Ala Tyr Gln Gly Ala Pro Ile Ala Ile Thr Val
                485                 490                 495

Glu Gly Ala Asn Ile Leu Thr Arg Ser Met Met Ile Phe Gly Gln Gly
                500                 505                 510

Ala Ile Arg Cys His Pro Tyr Val Leu Glu Glu Met Glu Ala Ala Lys
                515                 520                 525

Asn Asn Asp Val Asn Ala Phe Asp Lys Leu Leu Phe Lys His Ile Gly
                530                 535                 540

His Val Gly Ser Asn Lys Val Arg Ser Phe Trp Leu Gly Leu Thr Arg
545                 550                 555                 560

Gly Leu Thr Ser Ser Thr Pro Thr Gly Asp Ala Thr Lys Arg Tyr Tyr
                565                 570                 575

Gln His Leu Asn Arg Leu Ser Ala Asn Leu Ala Leu Leu Ser Asp Val
                580                 585                 590

Ser Met Ala Val Leu Gly Gly Ser Leu Lys Arg Arg Glu Arg Ile Ser
                595                 600                 605

Ala Arg Leu Gly Asp Ile Leu Ser Gln Leu Tyr Leu Ala Ser Ala Val
                610                 615                 620

Leu Lys Arg Tyr Asp Asp Glu Gly Arg Asn Glu Ala Asp Leu Pro Leu
625                 630                 635                 640

Val His Trp Gly Val Gln Asp Ala Leu Tyr Gln Ala Glu Gln Ala Met
                645                 650                 655

Asp Asp Leu Leu Gln Asn Phe Pro Asn Arg Val Val Ala Gly Leu Leu
                660                 665                 670

Asn Val Val Ile Phe Pro Thr Gly Arg His Tyr Leu Ala Pro Ser Asp
                675                 680                 685

Lys Leu Asp His Lys Val Ala Lys Ile Leu Gln Val Pro Asn Ala Thr
                690                 695                 700

Arg Ser Arg Ile Gly Arg Gly Gln Tyr Leu Thr Pro Ser Glu His Asn
705                 710                 715                 720

Pro Val Gly Leu Leu Glu Glu Ala Leu Val Asp Val Ile Ala Ala Asp
                725                 730                 735

Pro Ile His Gln Arg Ile Cys Lys Glu Leu Gly Lys Asn Leu Pro Phe
                740                 745                 750

Thr Arg Leu Asp Glu Leu Ala His Asn Ala Leu Val Lys Gly Leu Ile
                755                 760                 765

Asp Lys Asp Glu Ala Ala Ile Leu Val Lys Ala Glu Glu Ser Arg Leu
                770                 775                 780

Arg Ser Ile Asn Val Asp Asp Phe Asp Pro Glu Glu Leu Ala Thr Lys
785                 790                 795                 800

Pro Val Lys Leu Pro Glu Lys Val Arg Lys Val Glu Ala Ala
                805                 810
```

-continued

<210> SEQ ID NO 29
<211> LENGTH: 1665
<212> TYPE: DNA
<213> ORGANISM: Micrococcus luteus

<400> SEQUENCE: 29

```
atggtgaaga agctcgccct cgccgctctc gcgctggtgt tcctggcgcc gtcgctggtg      60
ctggtcgggg tcggggtggt gatgaaccct gccgcctcag cctcctgcac cgtggccggc     120
acaagcgtca cggtcggcga cgtccccgac gaactcaccg tcacgaccgc caacggcgag     180
accttcaccc tgaaccggca gcagctcacg catgcggcga cgatcatcga gaccgacacg     240
agcatcgacg gggtgacccg ggacgggctg gtgattgcgc tgatggcggc gctgaccgaa     300
tccaccctgc ggatgctgtc caacacgagc gtctatccgg agtcggcgga ctttcccaac     360
gatggcgacg gctccgacca cgattccctg gggttgtttc agatgcggcc gcagtccggg     420
tggggcaccg tcgccgagct gatggacccg acgtatcagg cgcaggcgtt cttcggcgga     480
cccaccggcc ccaaccaccc ctcaccgcgg ggcctgttgg acgtccccgg ctgggagcag     540
atggacaagg gcgaagctgc ccaagccgtc gaggtgtccg cctaccccga ccggtaccgc     600
aactacgagc ccgtcgccga gaccatcctg accaccctca ccggcaccac cgcaacagcc     660
gacgcagtca ctgcggggat gtcgaccgac gacaccgtgg ctccagcggt tcaggcggtg     720
gcggagtctt cacgggtggt gttcccggtg cccgagggca cctgggtgct gaccagcgag     780 tacgaccgc gggtccatcc gatctccggg gagagttcgt tccacaccgg caccgacttc     840
gccgccccgg acggcacccc gatcctcgcg gcggccgatg gcaccgtcac cgtcgccgag     900
ttctccggcg gctacggcgg gctcatcgtc atcgaacaca ccctcgacgg gcagaccttt     960
gcgaccgcgt acgggcacat gtgggagacc ggcatccacg tccaacccgg cgacactgtc    1020
accgctggcc agcacatcgg cgacattggc tcctccggca acagcaccgg gccgcatctg    1080
catttcgagg tccgtaccgg cggcaccgac ggtgagcaca tcgaccccgc cgcctggctc    1140
aacgcccatg atgctgctga cctccccgaa cccgagaccg gcgccccggc cggctgcgac    1200
cccgacacca gcactccggg cgggcagccc gaccccctcg acggtgatcc ggaccgcctc    1260
gtggatgacc ccaccagcga cggacagatc accgctcgga tgctgcacct ataccagcag    1320
ggcactgccg ccttccctga cacctcctgg gcctgctact cgccccgtcc cggcacccgc    1380
tccgaacacc cgctcggccg ggcctgcgat ctgaccttcg gcaacgccat cggccagcac    1440
cccacaccag cgcagctcga agccggctgg gacatcacca attggatgaa agaccacgcc    1500
gaaaccctcg gggtcgaata cctcatctgg cagggcaaga tctggtccct ctcccgcgac    1560
gccgaaggat ggcgcgacta caacggcggc ggcatgacg acccccggcga cgtcaccggc    1620 ggccactacg accacctcca cgtcaccgcc cggtccggga gctga                    1665
```

<210> SEQ ID NO 30
<211> LENGTH: 554
<212> TYPE: PRT
<213> ORGANISM: Micrococcus luteus

<400> SEQUENCE: 30

```
Met Val Lys Lys Leu Ala Leu Ala Ala Leu Ala Leu Val Phe Leu Ala
1               5                   10                  15

Pro Ser Leu Val Leu Val Gly Val Gly Val Val Met Asn Pro Ala Ala
            20                  25                  30
```

```
Ser Ala Ser Cys Thr Val Ala Gly Thr Ser Val Thr Val Gly Asp Val
        35              40              45

Pro Asp Glu Leu Thr Val Thr Thr Ala Asn Gly Glu Thr Phe Thr Leu
    50              55              60

Asn Arg Gln Gln Leu Thr His Ala Ala Thr Ile Ile Glu Thr Asp Thr
65              70              75              80

Ser Ile Asp Gly Val Thr Arg Asp Gly Leu Val Ile Ala Leu Met Ala
            85              90              95

Ala Leu Thr Glu Ser Thr Leu Arg Met Leu Ser Asn Thr Ser Val Tyr
            100             105             110

Pro Glu Ser Ala Asp Phe Pro Asn Asp Gly Asp Gly Ser Asp His Asp
        115             120             125

Ser Leu Gly Leu Phe Gln Met Arg Pro Gln Ser Gly Trp Gly Thr Val
    130             135             140

Ala Glu Leu Met Asp Pro Thr Tyr Gln Ala Gln Ala Phe Phe Gly Gly
145             150             155             160

Pro Thr Gly Pro Asn His Pro Ser Pro Arg Gly Leu Leu Asp Val Pro
                165             170             175

Gly Trp Glu Gln Met Asp Lys Gly Glu Ala Ala Gln Ala Val Glu Val
            180             185             190

Ser Ala Tyr Pro Asp Arg Tyr Arg Asn Tyr Glu Pro Val Ala Glu Thr
            195             200             205

Ile Leu Thr Thr Leu Thr Gly Thr Thr Ala Thr Ala Asp Ala Val Thr
    210             215             220

Ala Gly Met Ser Thr Asp Asp Thr Val Ala Pro Ala Val Gln Ala Val
225             230             235             240

Ala Glu Ser Ser Arg Val Val Phe Pro Val Pro Glu Gly Thr Trp Val
            245             250             255

Leu Thr Ser Glu Tyr Gly Pro Arg Val His Pro Ile Ser Gly Glu Ser
            260             265             270

Ser Phe His Thr Gly Thr Asp Phe Ala Ala Pro Asp Gly Thr Pro Ile
    275             280             285

Leu Ala Ala Ala Asp Gly Thr Val Thr Val Ala Glu Phe Ser Gly Gly
    290             295             300

Tyr Gly Gly Leu Ile Val Ile Glu His Thr Leu Asp Gly Gln Thr Phe
305             310             315             320

Ala Thr Ala Tyr Gly His Met Trp Glu Thr Gly Ile His Val Gln Pro
            325             330             335

Gly Asp Thr Val Thr Ala Gly Gln His Ile Gly Asp Ile Gly Ser Ser
            340             345             350

Gly Asn Ser Thr Gly Pro His Leu His Phe Glu Val Arg Thr Gly Gly
            355             360             365

Thr Asp Gly Glu His Ile Asp Pro Ala Ala Trp Leu Asn Ala His Asp
    370             375             380

Ala Ala Asp Leu Pro Glu Pro Glu Thr Gly Ala Pro Ala Gly Cys Asp
385             390             395             400

Pro Asp Thr Ser Thr Pro Gly Gly Gln Pro Asp Pro Leu Asp Gly Asp
            405             410             415

Pro Asp Arg Leu Val Asp Asp Pro Thr Ser Asp Gly Gln Ile Thr Ala
        420             425             430

Arg Met Leu His Leu Tyr Gln Gln Gly Thr Ala Ala Phe Pro Asp Thr
    435             440             445

Ser Trp Ala Cys Tyr Ser Pro Arg Pro Gly Thr Arg Ser Glu His Pro
```

-continued

```
        450              455              460

Leu Gly Arg Ala Cys Asp Leu Thr Phe Gly Asn Ala Ile Gly Gln His
465                 470              475                 480

Pro Thr Pro Ala Gln Leu Glu Ala Gly Trp Asp Ile Thr Asn Trp Met
                485              490              495

Lys Asp His Ala Glu Thr Leu Gly Val Glu Tyr Leu Ile Trp Gln Gly
            500              505              510

Lys Ile Trp Ser Leu Ser Arg Asp Ala Glu Gly Trp Arg Asp Tyr Asn
            515              520              525

Gly Gly Gly Met His Asp Pro Gly Asp Val Thr Gly Gly His Tyr Asp
            530              535              540

His Leu His Val Thr Ala Arg Ser Gly Ser
545                 550
```

```
<210> SEQ ID NO 31
<211> LENGTH: 720
<212> TYPE: DNA
<213> ORGANISM: Escherichia coli

<400> SEQUENCE: 31
atggtcatta aggcgcaaag cccggcgggt ttcgcggaag agtacattat tgaaagtatc       60
tggaataacc gcttccctcc cgggactatt ttgcccgcag aacgtgaact ttcagaatta      120
attggcgtaa cgcgtactac gttacgtgaa gtgttacagc gtctggcacg agatggctgg      180
ttgaccattc aacatggcaa gccgacgaag gtgaataatt tctgggaaac ttccggttta      240
aatatccttg aaacactggc gcgactggat cacgaaagtg tgccgcagct tattgataat      300
ttgctgtcgg tgcgtaccaa tatttccact atttttattc gcaccgcgtt tcgtcagcat      360
cccgataaag cgcaggaagt gctggctacc gctaatgaag tggccgatca cgccgatgcc      420
tttgccgagc tggattacaa catattccgc ggcctggcgt ttgcttccgg caacccgatt      480
tacggtctga ttcttaacgg gatgaaaggg ctgtatacgc gtattggtcg tcactatttc      540
gccaatccgg aagcgcgcag tctggcgctg ggcttctacc acaaactgtc ggcgttgtgc      600
agtgaaggcg cgcacgatca ggtgtacgaa acagtgcgtc gctatgggca tgagagtggc      660
gagatttggc accggatgca gaaaaatctg ccgggtgatt tagccattca ggggcgataa      720
```

```
<210> SEQ ID NO 32
<211> LENGTH: 239
<212> TYPE: PRT
<213> ORGANISM: Escherichia coli

<400> SEQUENCE: 32

Met Val Ile Lys Ala Gln Ser Pro Ala Gly Phe Ala Glu Glu Tyr Ile
1               5               10              15

Ile Glu Ser Ile Trp Asn Asn Arg Phe Pro Pro Gly Thr Ile Leu Pro
                20              25              30

Ala Glu Arg Glu Leu Ser Glu Leu Ile Gly Val Thr Arg Thr Thr Leu
            35              40              45

Arg Glu Val Leu Gln Arg Leu Ala Arg Asp Gly Trp Leu Thr Ile Gln
        50              55              60

His Gly Lys Pro Thr Lys Val Asn Asn Phe Trp Glu Thr Ser Gly Leu
65              70              75              80

Asn Ile Leu Glu Thr Leu Ala Arg Leu Asp His Glu Ser Val Pro Gln
                85              90              95

Leu Ile Asp Asn Leu Leu Ser Val Arg Thr Asn Ile Ser Thr Ile Phe
```

-continued

```
                  100                 105                 110
Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
    130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
                180                 185                 190

Tyr His Lys Leu Ser Ala Leu Cys Ser Glu Gly Ala His Asp Gln Val
                195                 200                 205

Tyr Glu Thr Val Arg Arg Tyr Gly His Glu Ser Gly Glu Ile Trp His
    210                 215                 220

Arg Met Gln Lys Asn Leu Pro Gly Asp Leu Ala Ile Gln Gly Arg
225                 230                 235
```

```
<210> SEQ ID NO 33
<211> LENGTH: 324
<212> TYPE: DNA
<213> ORGANISM: Salmonella enterica

<400> SEQUENCE: 33
atgcagacac agattaaagt acgtggctac catcttgacg tttaccaaca cgtaaacaat      60
gctcgttatc ttgaattttt agaagaggct cgttgggatg ggttagaaaa cagcgatagt     120
tttcagtgga tgacggcacg caatatcgcc tttgtggtcg tgaacattaa catcaattac     180
cgccgtccag ccgtactgtc agatctttta actgtcacat cccaagtaca acagttgaat     240
ggcaagtcag gagttttgtc acagactatt accctggaac ctgagggaca gttgtagcc      300 gatgcgctta ttacattcgt ttaa                                            324
```

```
<210> SEQ ID NO 34
<211> LENGTH: 107
<212> TYPE: PRT
<213> ORGANISM: Salmonella enterica

<400> SEQUENCE: 34

Met Gln Thr Gln Ile Lys Val Arg Gly Tyr His Leu Asp Val Tyr Gln
1               5                   10                  15

His Val Asn Asn Ala Arg Tyr Leu Glu Phe Leu Glu Glu Ala Arg Trp
                20                  25                  30

Asp Gly Leu Glu Asn Ser Asp Ser Phe Gln Trp Met Thr Ala Arg Asn
            35                  40                  45

Ile Ala Phe Val Val Val Asn Ile Asn Ile Asn Tyr Arg Arg Pro Ala
    50                  55                  60

Val Leu Ser Asp Leu Leu Thr Val Thr Ser Gln Val Gln Gln Leu Asn
65                  70                  75                  80

Gly Lys Ser Gly Val Leu Ser Gln Thr Ile Thr Leu Glu Pro Glu Gly
                85                  90                  95

Gln Val Val Ala Asp Ala Leu Ile Thr Phe Val
            100                 105
```

```
<210> SEQ ID NO 35
<211> LENGTH: 399
<212> TYPE: DNA
```

<213> ORGANISM: Cucumis sativus

<400> SEQUENCE: 35
atgcaaacgc agatcaaagt acgcggctat caccttgacg tataccaaca tgttaataat      60
gctcgctacc ttgaattcct ggaggaggcc cgttgggatg gtcttgagaa cagcgagagt     120
tttcaatggc ttacggctca taatattgcc tttgtggtag tcaacatcaa tatcaactat     180
cgccgccctg ctgttttggg tgacgtgttg accgttacga gcgaagttca gcaattaaac     240
ggcaaaagcg gtgtattgtc acaagtagtt acccttgagc cagaaggcca ggttgtcgct     300
gacgctctta tcaccttcgt ctgtatcgat ttaaaaaccc agaaagcttt accccttgag     360
ggcgagttgc gtgaaaaact tgagttgatg attgcttaa                           399

<210> SEQ ID NO 36
<211> LENGTH: 132
<212> TYPE: PRT
<213> ORGANISM: Cucumis sativus

<400> SEQUENCE: 36

Met Gln Thr Gln Ile Lys Val Arg Gly Tyr His Leu Asp Val Tyr Gln
1               5                   10                  15

His Val Asn Asn Ala Arg Tyr Leu Glu Phe Leu Glu Glu Ala Arg Trp
            20                  25                  30

Asp Gly Leu Glu Asn Ser Glu Ser Phe Gln Trp Leu Thr Ala His Asn
        35                  40                  45

Ile Ala Phe Val Val Val Asn Ile Asn Ile Asn Tyr Arg Arg Pro Ala
        50                  55                  60

Val Leu Gly Asp Val Leu Thr Val Thr Ser Glu Val Gln Gln Leu Asn
65                  70                  75                  80

Gly Lys Ser Gly Val Leu Ser Gln Val Val Thr Leu Glu Pro Glu Gly
                85                  90                  95

Gln Val Val Ala Asp Ala Leu Ile Thr Phe Val Cys Ile Asp Leu Lys
            100                 105                 110

Thr Gln Lys Ala Leu Pro Leu Glu Gly Glu Leu Arg Glu Lys Leu Glu
        115                 120                 125

Leu Met Ile Ala
    130

<210> SEQ ID NO 37
<211> LENGTH: 399
<212> TYPE: DNA
<213> ORGANISM: Cronobacter turicensis

<400> SEQUENCE: 37
atgcaaactc agattaaggt acgcggttac cacattgacg tgtaccaaca tgtcaacaat      60
gcgcgctatt tggagttcct tgaggaagcg cgctgggatg gtctggagaa cgatgaatct     120
tttaaatgga tgatggcaaa taatatcgct ttcatcgtcg tgaacatcaa tattaattac     180
cgccgtcctg ccgtgctggg cgatcttttg actgttacga gtcaagtgaa gcaattgaat     240
gggaaaagcg gcatcctttc tcaaatcatc acgctggaac ctgagggaga ggttgttgct     300
gacgccttga ttacctttgt ttgcatcgat cttaaaactc aaaaagctct tccgatcgaa     360
ggtgaattac gcgaaaagct ggagaagctt actggttaa                           399

<210> SEQ ID NO 38
<211> LENGTH: 132
<212> TYPE: PRT

<213> ORGANISM: Cronobacter turicensis

<400> SEQUENCE: 38

```
Met Gln Thr Gln Ile Lys Val Arg Gly Tyr His Ile Asp Val Tyr Gln
1               5                   10                  15

His Val Asn Asn Ala Arg Tyr Leu Glu Phe Leu Glu Glu Ala Arg Trp
            20                  25                  30

Asp Gly Leu Glu Asn Asp Glu Ser Phe Lys Trp Met Met Ala Asn Asn
        35                  40                  45

Ile Ala Phe Ile Val Val Asn Ile Asn Ile Asn Tyr Arg Arg Pro Ala
    50                  55                  60

Val Leu Gly Asp Leu Leu Thr Val Thr Ser Gln Val Lys Gln Leu Asn
65                  70                  75                  80

Gly Lys Ser Gly Ile Leu Ser Gln Ile Ile Thr Leu Glu Pro Glu Gly
                85                  90                  95

Glu Val Val Ala Asp Ala Leu Ile Thr Phe Val Cys Ile Asp Leu Lys
            100                 105                 110

Thr Gln Lys Ala Leu Pro Ile Glu Gly Glu Leu Arg Glu Lys Leu Glu
        115                 120                 125

Lys Leu Thr Gly
    130
```

<210> SEQ ID NO 39
<211> LENGTH: 402
<212> TYPE: DNA
<213> ORGANISM: Beauveria bassiana

<400> SEQUENCE: 39

```
atgcagaccc acatcaaagt ccgtggttat catatggatg tttaccagca cgtgaataat      60
gcacgctacc tggaattttt ggaggaagct cgctgggaag gacttgagaa gacgaccgga     120
ttccagtgga tgacagagca taacatcgca ttcatcgtcg taaatattaa tattagctac     180
cgtcgtccgg ccgtcttggg agacttactg cgtattgaaa gcagcttgca gcaattaaat     240
gggaaaagcg gggtgttgag ccaggtagta accttggaac cggagggaga ggccgttgcc     300
gatgcacttt tgacatttgt ctgcatcgat cttaagacac agaaggcagt accgttagag     360
ggtgagttgc gcgacaaact ggagcagatg atgaatgcat aa                        402
```

<210> SEQ ID NO 40
<211> LENGTH: 133
<212> TYPE: PRT
<213> ORGANISM: Beauveria bassiana

<400> SEQUENCE: 40

```
Met Gln Thr His Ile Lys Val Arg Gly Tyr His Met Asp Val Tyr Gln
1               5                   10                  15

His Val Asn Asn Ala Arg Tyr Leu Glu Phe Leu Glu Glu Ala Arg Trp
            20                  25                  30

Glu Gly Leu Glu Lys Thr Thr Gly Phe Gln Trp Met Thr Glu His Asn
        35                  40                  45

Ile Ala Phe Ile Val Val Asn Ile Asn Ile Ser Tyr Arg Arg Pro Ala
    50                  55                  60

Val Leu Gly Asp Leu Leu Arg Ile Glu Ser Ser Leu Gln Gln Leu Asn
65                  70                  75                  80

Gly Lys Ser Gly Val Leu Ser Gln Val Val Thr Leu Glu Pro Glu Gly
                85                  90                  95
```

```
Glu Ala Val Ala Asp Ala Leu Leu Thr Phe Val Cys Ile Asp Leu Lys
            100                 105                 110

Thr Gln Lys Ala Val Pro Leu Glu Gly Glu Leu Arg Asp Lys Leu Glu
        115                 120                 125

Gln Met Met Asn Ala
        130
```

```
<210> SEQ ID NO 41
<211> LENGTH: 399
<212> TYPE: DNA
<213> ORGANISM: Buttiauxella agrestis

<400> SEQUENCE: 41
atgcaaacgc acattaaagt ccgtggctat catatggatg tctatcaaca tgtgaacaat       60
gcacgttacc ttgaattttt agaagaagct cgctgggagg gtttggaaaa taccgcaggg      120
tttcaatgga tgactgaaca taacatcgcg tttattgttg taaatatcaa tatcaactat      180
cgtcgccctg cggtacttgg tgaccttctt cgcattgagt catctcttca acagctgaat      240
gggaagagtg gcgtcctgtc gcaagtcgtg aagctggagc ctgagggcga aatcgttgct      300
gatgccttgc ttacctttgt ctgtattgac ctgaaaactc aaaaatctgt acctttagag      360
ggagaattac gtgaaaaatt agtgcagatg atggagtaa                              399
```

```
<210> SEQ ID NO 42
<211> LENGTH: 132
<212> TYPE: PRT
<213> ORGANISM: Buttiauxella agrestis

<400> SEQUENCE: 42

Met Gln Thr His Ile Lys Val Arg Gly Tyr His Met Asp Val Tyr Gln
1               5                   10                  15

His Val Asn Asn Ala Arg Tyr Leu Glu Phe Leu Glu Glu Ala Arg Trp
            20                  25                  30

Glu Gly Leu Glu Asn Thr Ala Gly Phe Gln Trp Met Thr Glu His Asn
        35                  40                  45

Ile Ala Phe Ile Val Val Asn Ile Asn Ile Asn Tyr Arg Arg Pro Ala
    50                  55                  60

Val Leu Gly Asp Leu Leu Arg Ile Glu Ser Ser Leu Gln Gln Leu Asn
65                  70                  75                  80

Gly Lys Ser Gly Val Leu Ser Gln Val Val Lys Leu Glu Pro Glu Gly
                85                  90                  95

Glu Ile Val Ala Asp Ala Leu Leu Thr Phe Val Cys Ile Asp Leu Lys
            100                 105                 110

Thr Gln Lys Ser Val Pro Leu Glu Gly Glu Leu Arg Glu Lys Leu Val
        115                 120                 125

Gln Met Met Glu
        130
```

```
<210> SEQ ID NO 43
<211> LENGTH: 432
<212> TYPE: DNA
<213> ORGANISM: Serratia odorifera

<400> SEQUENCE: 43
atgcagactc tgattaaagt acgtggttac cacttggacg tatatcaaca tgttaacaac       60
gcacgctacc tggagttcct tgaggaagca cgttgggaat ggcttgataa tttggatgct      120
tttcgctgga tgacagaaaa caacattgct tttatcgtcg ttaatatcaa catcaactac      180
```

-continued

```
cgcaaaccag ctgtgttagg tgaccgtctg cgtatcgatt cgcgcatgga acaactgaat      240
ggtaagtcgg gtgtcctttc tcaaaaagtg accttagaac cgcaagggag tgcggtagca      300
gacgccctgt taacctttgt ttgcgtggac ttgaaaacgc agcgcgccct tcctattgaa      360
ggagaacttc gtgaacactt aatgtctctg caacagcccg tcatcaacgc taccggtgat      420
ggacgcttgt aa                                                          432
```

```
<210> SEQ ID NO 44
<211> LENGTH: 143
<212> TYPE: PRT
<213> ORGANISM: Serratia odorifera

<400> SEQUENCE: 44

Met Gln Thr Leu Ile Lys Val Arg Gly Tyr His Leu Asp Val Tyr Gln
1               5                   10                  15

His Val Asn Asn Ala Arg Tyr Leu Glu Phe Leu Glu Glu Ala Arg Trp
                20                  25                  30

Glu Trp Leu Asp Asn Leu Asp Ala Phe Arg Trp Met Thr Glu Asn Asn
            35                  40                  45

Ile Ala Phe Ile Val Val Asn Ile Asn Ile Asn Tyr Arg Lys Pro Ala
        50                  55                  60

Val Leu Gly Asp Arg Leu Arg Ile Asp Ser Arg Met Glu Gln Leu Asn
65                  70                  75                  80

Gly Lys Ser Gly Val Leu Ser Gln Lys Val Thr Leu Glu Pro Gln Gly
                85                  90                  95

Ser Ala Val Ala Asp Ala Leu Leu Thr Phe Val Cys Val Asp Leu Lys
                100                 105                 110

Thr Gln Arg Ala Leu Pro Ile Glu Gly Glu Leu Arg Glu His Leu Met
            115                 120                 125

Ser Leu Gln Gln Pro Val Ile Asn Ala Thr Gly Asp Gly Arg Leu
        130                 135                 140
```

```
<210> SEQ ID NO 45
<211> LENGTH: 411
<212> TYPE: DNA
<213> ORGANISM: Mycobacterium tuberculosis

<400> SEQUENCE: 45
atgtccacga caattaaggt aattggctac catattgacg catttggaca cgttaacaac       60
gcccgctatc ttgagttcct ggaagccgct cgctgggatt ggttagaatc atacgatgcg      120
tatcgctggt ttaagcagat ggatatcgct gtcgtcgtag tcaacatcaa tatcaactac      180
cgccttcccg tgtatgtcgg cgaacgcctt gttattgata gctatttaca gcatgctgga      240
cagaagtcag gagtttttgaa gcagattatc acacgtcaag aagacaaaca ggttgtcgcc      300
gatgctgagg taactttttgt cttcattaac atgaaaactg gtaaggcaat tcctatcgag      360
ggggagattc gtgacaagtt tgagttactg acagcgccaa aggagggtta a              411
```

```
<210> SEQ ID NO 46
<211> LENGTH: 136
<212> TYPE: PRT
<213> ORGANISM: Mycobacterium tuberculosis

<400> SEQUENCE: 46

Met Ser Thr Thr Ile Lys Val Ile Gly Tyr His Ile Asp Ala Phe Gly
1               5                   10                  15
```

His Val Asn Asn Ala Arg Tyr Leu Glu Phe Leu Glu Ala Ala Arg Trp
            20                  25                  30

Asp Trp Leu Glu Ser Tyr Asp Ala Tyr Arg Trp Phe Lys Gln Met Asp
        35                  40                  45

Ile Ala Val Val Val Val Asn Ile Asn Ile Asn Tyr Arg Leu Pro Val
    50                  55                  60

Tyr Val Gly Glu Arg Leu Val Ile Asp Ser Tyr Leu Gln His Ala Gly
65                  70                  75                  80

Gln Lys Ser Gly Val Leu Lys Gln Ile Ile Thr Arg Gln Glu Asp Lys
                85                  90                  95

Gln Val Val Ala Asp Ala Glu Val Thr Phe Val Phe Ile Asn Met Lys
            100                 105                 110

Thr Gly Lys Ala Ile Pro Ile Glu Gly Glu Ile Arg Asp Lys Phe Glu
        115                 120                 125

Leu Leu Thr Ala Pro Lys Glu Gly
    130                 135

<210> SEQ ID NO 47
<211> LENGTH: 414
<212> TYPE: DNA
<213> ORGANISM: Mycobacterium tuberculosis

<400> SEQUENCE: 47
atgtccgctg gcttcgtggc acctgttccc gtgcgttgga gtgatattga catgtaccaa      60
cacattaacc acgccaccat ggtcacttta cttgaggaag cccgcgtgcc gtttctgaaa     120
gaaccgtttg ctgccgacat cacaacaatt ggcttactta ttgctgatgt acgtgtaact     180
tacaaggacc aactgcgttt agccgattcg cctttgcaag tcactatctg gacgaagcgt     240
ttacgtgctg tggatttcac tcttggatat gaagtgcgct cagtggcggc ggaccccgag     300
tcaaaacctg cagtggttgc agaaagtcag ctggcagccg ttcatattga gagcaacgc     360 cttgttcgtc tgtccccgca gcatcgtgaa tatttacaac gttggatgcg ctaa          414

<210> SEQ ID NO 48
<211> LENGTH: 137
<212> TYPE: PRT
<213> ORGANISM: Mycobacterium tuberculosis

<400> SEQUENCE: 48

Met Ser Ala Gly Phe Val Ala Pro Val Pro Val Arg Trp Ser Asp Ile
1               5                   10                  15

Asp Met Tyr Gln His Ile Asn His Ala Thr Met Val Thr Leu Leu Glu
            20                  25                  30

Glu Ala Arg Val Pro Phe Leu Lys Glu Pro Phe Ala Ala Asp Ile Thr
        35                  40                  45

Thr Ile Gly Leu Leu Ile Ala Asp Val Arg Val Thr Tyr Lys Asp Gln
    50                  55                  60

Leu Arg Leu Ala Asp Ser Pro Leu Gln Val Thr Ile Trp Thr Lys Arg
65                  70                  75                  80

Leu Arg Ala Val Asp Phe Thr Leu Gly Tyr Glu Val Arg Ser Val Ala
                85                  90                  95

Ala Asp Pro Glu Ser Lys Pro Ala Val Val Ala Glu Ser Gln Leu Ala
            100                 105                 110

Ala Val His Ile Glu Glu Gln Arg Leu Val Arg Leu Ser Pro Gln His
        115                 120                 125

Arg Glu Tyr Leu Gln Arg Trp Met Arg

```
          130              135
```

```
<210> SEQ ID NO 49
<211> LENGTH: 414
<212> TYPE: DNA
<213> ORGANISM: Mycobacterium tuberculosis

<400> SEQUENCE: 49
atgacggtcg gcttcgtggc acaggtaccc gtacgttggt cagatattga catgtaccag      60
catgtcaatc atgctactat ggtgacctta cttgaagagg ctcgcgtgcc attttttaaag   120 ccggcatttg aggtggatat tttagaaatt ggtttactga tcgctgatgt ccgcgtgacc    180
tacaaggccc agctgaaact ggtggactcg cccttacaag tgaccgtttg gaccaaacag    240
ttacgcactg tagatttcac gctgggctac gaagttcgct cggtcggtgc cgaccctcaa    300
tcaaaacctg cggttattgc cgaaagtcag cttgccgctg tccacatcca agaacagcgt    360
cttgtacgtc ttgggcctca gcaccgcgag taccttcaac gctggctgcg ttaa          414
```

```
<210> SEQ ID NO 50
<211> LENGTH: 137
<212> TYPE: PRT
<213> ORGANISM: Mycobacterium tuberculosis

<400> SEQUENCE: 50

Met Thr Val Gly Phe Val Ala Gln Val Pro Val Arg Trp Ser Asp Ile
1               5                   10                  15

Asp Met Tyr Gln His Val Asn His Ala Thr Met Val Thr Leu Leu Glu
            20                  25                  30

Glu Ala Arg Val Pro Phe Leu Lys Pro Ala Phe Glu Val Asp Ile Leu
        35                  40                  45

Glu Ile Gly Leu Leu Ile Ala Asp Val Arg Val Thr Tyr Lys Ala Gln
        50                  55                  60

Leu Lys Leu Val Asp Ser Pro Leu Gln Val Thr Val Trp Thr Lys Gln
65                  70                  75                  80

Leu Arg Thr Val Asp Phe Thr Leu Gly Tyr Glu Val Arg Ser Val Gly
                85                  90                  95

Ala Asp Pro Gln Ser Lys Pro Ala Val Ile Ala Glu Ser Gln Leu Ala
            100                 105                 110

Ala Val His Ile Gln Glu Gln Arg Leu Val Arg Leu Gly Pro Gln His
            115                 120                 125

Arg Glu Tyr Leu Gln Arg Trp Leu Arg
        130                 135
```

```
<210> SEQ ID NO 51
<211> LENGTH: 384
<212> TYPE: DNA
<213> ORGANISM: Neisseria gonorrhoeae

<400> SEQUENCE: 51
atgaagctta ccgttcgtaa ctatcacttg acgggtatg gacatgtgaa caacgcgcgt     60
taccttgagt ttcttgaaga ggcgcgttgg gcctttttcg aaaaacgtgg attgatgcat   120
gagttagcgg gtttaatttt gattgtcgct cgcatcgata ttcgttattc gcgtccggct   180
gtagagggag atgtgctgca gttttcatgt cgtttaaaga ccccgggaat gcgccgtatc   240
gtcttgacgc aaacgatcac gttacctaac ggtaagacgg ccgcggaggc agacattacc   300
cttatgcccg tgcatgctgc tacccagcgc accgtgagtt tacctgccac gcttgctcgc   360
```

```
gctcttgagg ccttatctga gtaa                                            384
```

<210> SEQ ID NO 52
<211> LENGTH: 127
<212> TYPE: PRT
<213> ORGANISM: Neisseria gonorrhoeae

<400> SEQUENCE: 52

```
Met Lys Leu Thr Val Arg Asn Tyr His Leu Asp Gly Tyr Gly His Val
1               5                   10                  15

Asn Asn Ala Arg Tyr Leu Glu Phe Leu Glu Glu Ala Arg Trp Ala Phe
            20                  25                  30

Phe Glu Lys Arg Gly Leu Met His Glu Leu Ala Gly Leu Ile Leu Ile
        35                  40                  45

Val Ala Arg Ile Asp Ile Arg Tyr Ser Arg Pro Ala Val Glu Gly Asp
    50                  55                  60

Val Leu Gln Phe Ser Cys Arg Leu Lys Thr Pro Gly Met Arg Arg Ile
65                  70                  75                  80

Val Leu Thr Gln Thr Ile Thr Leu Pro Asn Gly Lys Thr Ala Ala Glu
                85                  90                  95

Ala Asp Ile Thr Leu Met Pro Val His Ala Ala Thr Gln Arg Thr Val
            100                 105                 110

Ser Leu Pro Ala Thr Leu Ala Arg Ala Leu Glu Ala Leu Ser Glu
        115                 120                 125
```

<210> SEQ ID NO 53
<211> LENGTH: 414
<212> TYPE: DNA
<213> ORGANISM: Marinomonas ushuaiensis

<400> SEQUENCE: 53

```
atgattaata ttatccagat taaggtgcgc ggataccacc tggacatttt ccaacacgtg    60
aacaatgcgc gttacttgga attttttggaa gaaggccgct gggctttctt cgatgaattc   120
ggcgcaggta ccgagcttat ggagcagggt ctggcgtggg cagtggttaa cattaacatt   180
gactttcgtg ctgagggtaa ttttgccgac gtgttggagg tgcatactca gttttccaaa   240
ttggggaatc gcagcgttac aatgaagcag cgcatcatga atgcgaagac agatacgctg   300
gtggcagaag ccgatgtcac ttatgtctgt ttttcaaaag aaaagaaggc cgcagtacct   360
ttgccggacg actacaagat gaagattcag aaggctttgg aggaaagcga ctaa          414
```

<210> SEQ ID NO 54
<211> LENGTH: 137
<212> TYPE: PRT
<213> ORGANISM: Marinomonas ushuaiensis

<400> SEQUENCE: 54

```
Met Ile Asn Ile Ile Gln Ile Lys Val Arg Gly Tyr His Leu Asp Ile
1               5                   10                  15

Phe Gln His Val Asn Asn Ala Arg Tyr Leu Glu Phe Leu Glu Glu Gly
            20                  25                  30

Arg Trp Ala Phe Phe Asp Glu Phe Gly Ala Gly Thr Glu Leu Met Glu
        35                  40                  45

Gln Gly Leu Ala Trp Ala Val Val Asn Ile Asn Ile Asp Phe Arg Ala
    50                  55                  60

Glu Gly Asn Phe Ala Asp Val Leu Glu Val His Thr Gln Phe Ser Lys
65                  70                  75                  80
```

Leu Gly Asn Arg Ser Val Thr Met Lys Gln Arg Ile Met Asn Ala Lys
                85                  90                  95

Thr Asp Thr Leu Val Ala Glu Ala Asp Val Thr Tyr Val Cys Phe Ser
            100                 105                 110

Lys Glu Lys Lys Ala Ala Val Pro Leu Pro Asp Asp Tyr Lys Met Lys
        115                 120                 125

Ile Gln Lys Ala Leu Glu Glu Ser Asp
    130                 135

<210> SEQ ID NO 55
<211> LENGTH: 417
<212> TYPE: DNA
<213> ORGANISM: Mycobacterium tuberculosis

<400> SEQUENCE: 55
atgaccttct cagtcccagt tactgtccgc gggtacgagt tagatgtgaa tggacacctg      60
aaccaagccg tgtaccatca atacgctgaa cacgcacgtt gggaggtact gcgtgcggcc     120
ggtttggtac ccgacaagat gcgcttgtcg ggtttgggtc ctgtcgtatt ggagtcaact     180
gtaaagtacc gtcgtgaatt gcacttgggt gacgagatta ctgtcacttg tgagtgccgc     240
tggggtgagg gaaaggcttt ttggatggac agcaaatcc gtaaattgga cggtaccgtt      300
tctgctgagt tttcagtagt tcttgggctt atggacttag atgcccgcaa gctggtatct     360
aaccctggga agcgctttct ggagctggcg gagtcacctg acgtcctggg gttgtaa        417

<210> SEQ ID NO 56
<211> LENGTH: 138
<212> TYPE: PRT
<213> ORGANISM: Mycobacterium tuberculosis

<400> SEQUENCE: 56

Met Thr Phe Ser Val Pro Val Thr Val Arg Gly Tyr Glu Leu Asp Val
1               5                   10                  15

Asn Gly His Leu Asn Gln Ala Val Tyr His Gln Tyr Ala Glu His Ala
            20                  25                  30

Arg Trp Glu Val Leu Arg Ala Ala Gly Leu Val Pro Asp Lys Met Arg
        35                  40                  45

Leu Ser Gly Leu Gly Pro Val Val Leu Glu Ser Thr Val Lys Tyr Arg
    50                  55                  60

Arg Glu Leu His Leu Gly Asp Glu Ile Thr Val Thr Cys Glu Cys Arg
65                  70                  75                  80

Trp Gly Glu Gly Lys Ala Phe Trp Met Asp Gln Gln Ile Arg Lys Leu
                85                  90                  95

Asp Gly Thr Val Ser Ala Glu Phe Ser Val Val Leu Gly Leu Met Asp
            100                 105                 110

Leu Asp Ala Arg Lys Leu Val Ser Asn Pro Gly Lys Arg Phe Leu Glu
        115                 120                 125

Leu Ala Glu Ser Pro Asp Val Leu Gly Leu
    130                 135

<210> SEQ ID NO 57
<211> LENGTH: 408
<212> TYPE: DNA
<213> ORGANISM: Pseudomonas aeruginosa

<400> SEQUENCE: 57
atgagttcgg agcacaaaat tctggcccgc atccctatct cagtacgttg gcgtgatatg      60

-continued

```
gatagcatgg gccacgtaaa taacgcaaaa tatatcagtt acctggaaga ggcccgtgtg      120
cgctggatgc tgggggttga cggtgtctca atgaccgatc gtatcgctcc tgtggtggcg      180
gccacgaacg tgaattatcg tttaccgatt gtgtggccta acgatatcgt ggtggaactg      240
tttgtcgagc gcctgggcaa ctcctctgtt acaattggtc atcgtattgt tgaccagcaa      300
gatgccagca aactgtattc tgacggtaac gtagttgtgg tatggatgga cacccagaca      360
gggaaatcag ctccacttcc cgaggccatt cgcaacgcaa gtacataa                   408
```

```
<210> SEQ ID NO 58
<211> LENGTH: 135
<212> TYPE: PRT
<213> ORGANISM: Pseudomonas aeruginosa

<400> SEQUENCE: 58

Met Ser Ser Glu His Lys Ile Leu Ala Arg Ile Pro Ile Ser Val Arg
1               5                   10                  15

Trp Arg Asp Met Asp Ser Met Gly His Val Asn Asn Ala Lys Tyr Ile
            20                  25                  30

Ser Tyr Leu Glu Glu Ala Arg Val Arg Trp Met Leu Gly Val Asp Gly
        35                  40                  45

Val Ser Met Thr Asp Arg Ile Ala Pro Val Val Ala Ala Thr Asn Val
    50                  55                  60

Asn Tyr Arg Leu Pro Ile Val Trp Pro Asn Asp Ile Val Val Glu Leu
65                  70                  75                  80

Phe Val Glu Arg Leu Gly Asn Ser Ser Val Thr Ile Gly His Arg Ile
                85                  90                  95

Val Asp Gln Gln Asp Ala Ser Lys Leu Tyr Ser Asp Gly Asn Val Val
            100                 105                 110

Val Val Trp Met Asp Thr Gln Thr Gly Lys Ser Ala Pro Leu Pro Glu
        115                 120                 125

Ala Ile Arg Asn Ala Ser Thr
    130                 135
```

```
<210> SEQ ID NO 59
<211> LENGTH: 417
<212> TYPE: DNA
<213> ORGANISM: Mycobacterium tuberculosis

<400> SEQUENCE: 59
atgtctggaa ctggctttgt cactcccgtg gcggtgcgct ggagcgacat cgatatgtat       60
cagcatatca accatgcgac tatggtgaca ttactggagg aagcacgtat cccgttttta      120
agcccagtat tcggtgcaga aatcattaca accggcttgc tgatcgcaga ggtccgcatt      180
agttacaagg gcaactgcg ccttcttgat agcccactgc aggtgacaat tacagtcgac       240
cgtcttcgtg cggtcgattt tactctgggc tacgaagtgc gctctgttaa tgctgcgcct      300
gattcgcgtc cggcagtcat cgcagaaacc cagcttgctg cctttgacat tgatgaacaa      360
aagttggtcc gtttaagcgc cgaacatcgt gaataccttg gtcgcttcgt gcgctaa         417
```

```
<210> SEQ ID NO 60
<211> LENGTH: 138
<212> TYPE: PRT
<213> ORGANISM: Mycobacterium tuberculosis

<400> SEQUENCE: 60

Met Ser Gly Thr Gly Phe Val Thr Pro Val Ala Val Arg Trp Ser Asp
1               5                   10                  15
```

-continued

```
Ile Asp Met Tyr Gln His Ile Asn His Ala Thr Met Val Thr Leu Leu
        20              25              30

Glu Glu Ala Arg Ile Pro Phe Leu Ser Pro Val Phe Gly Ala Glu Ile
        35              40              45

Ile Thr Thr Gly Leu Leu Ile Ala Glu Val Arg Ile Ser Tyr Lys Gly
        50              55              60

Gln Leu Arg Leu Leu Asp Ser Pro Leu Gln Val Thr Ile Thr Val Asp
65              70              75              80

Arg Leu Arg Ala Val Asp Phe Thr Leu Gly Tyr Glu Val Arg Ser Val
            85              90              95

Asn Ala Ala Pro Asp Ser Arg Pro Ala Val Ile Ala Glu Thr Gln Leu
            100             105             110

Ala Ala Phe Asp Ile Asp Glu Gln Lys Leu Val Arg Leu Ser Ala Glu
        115             120             125

His Arg Glu Tyr Leu Gly Arg Phe Val Arg
    130             135
```

CELLS AND METHODS FOR PRODUCING METHYL KETONES

CROSS-REFERENCE TO RELATED APPLICATIONS

The present application is a national filing under 35 U.S.C. § 371 of PCT/US2021/033382, filed May 20, 2021, which claims priority to provisional application Ser. No. 63/027,872, filed May 20, 2020, which is incorporated herein by reference.

STATEMENT REGARDING FEDERALLY SPONSORED RESEARCH

This invention was made with government support under CBET1703504 awarded by the National Science Foundation and under DE-SC0018420 awarded by the US Department of Energy. The government has certain rights in the invention.

SEQUENCE LISTING

The instant application contains a Sequence Listing which has been submitted in ASCII format via EFS-Web and is hereby incorporated by reference in its entirety. The ASCII copy, created on May 18, 2021 is named PCT-210520-Application-P200352W001-SEQ_LIST_ST25.txt and is 120,925 bytes in size.

FIELD OF THE INVENTION

The invention is directed to recombinant cells and methods for producing methyl ketones, such as medium-chain length methyl ketones.

BACKGROUND

Methyl ketones, particularly medium-chain length methyl ketones, are valuable chemical compounds that serve several biological and industrial purposes such as pheromones, flavoring, fragrant agents and diesel fuels. Tools and methods for producing methyl ketones are needed.

SUMMARY OF THE INVENTION

One aspect of the invention is directed to recombinant cells, such as recombinant cells for producing methyl ketones. A recombinant cell of the invention preferably comprises any one, any two, or each of a recombinant β-ketoacyl-CoA thioesterase gene, a recombinant acyl-ACP thioesterase gene, an a recombinant acyl-CoA synthetase gene.

In some versions, the recombinant β-ketoacyl-CoA thioesterase gene encodes a FadM protein or a homolog thereof. In some versions, the recombinant β-ketoacyl-CoA thioesterase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:6, SEQ ID NO:8, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, or SEQ ID NO:60.

In some versions, the acyl-ACP thioesterase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:2 or SEQ ID NO:4.

In some versions, the recombinant acyl-CoA synthetase gene encodes a FadD protein or a homolog thereof. In some versions, the recombinant acyl-CoA synthetase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:10 or SEQ ID NO:12.

In some versions, the recombinant cell further comprises a functional deletion of a native fadR gene or a homolog thereof.

In some versions, the recombinant cell further comprises a functional deletion of a native acyl-CoA dehydrogenase gene. In some versions, the acyl-CoA dehydrogenase gene is a fadE gene or a homolog thereof.

In some versions, the recombinant cell exhibits enhanced production of methyl ketone with respect to a corresponding native cell. In some versions, the methyl ketone comprises medium-chain methyl ketone. In some versions, the medium-chain methyl ketone comprises at least one of 2-heptanone, 2-nonanone, and 2-undecanone.

In some versions, the recombinant cell further comprises a functional deletion of at least one of a native enoyl-CoA hydratase gene and a native 3-hydroxyacyl-CoA dehydrogenase gene. In some versions, the at least one of the enoyl-CoA hydratase gene and the 3-hydroxyacyl-CoA dehydrogenase gene comprises at least one of a fadB gene or a homolog thereof and a fadJ gene or a homolog thereof.

In some versions, the recombinant cell comprises at least one of: a functional deletion of a native fadR gene or a homolog thereof; and a recombinant 3-ketoacyl-CoA thiolase gene.

In some versions, the recombinant cell comprises a recombinant 3-ketoacyl-CoA thiolase gene. In some versions, the recombinant 3-ketoacyl-CoA thiolase gene encodes at least one of a FadA protein or a homolog thereof and a FadI protein or a homolog thereof. In some versions, the recombinant 3-ketoacyl-CoA thiolase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:20, SEQ ID NO:22, SEQ ID NO:24, or SEQ ID NO:26.

In some versions, the recombinant β-ketoacyl-CoA thioesterase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:8, the acyl-ACP thioesterase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:2. the recombinant acyl-CoA synthetase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:12, the recombinant cell comprises a functional deletion of a native acyl-CoA dehydrogenase gene, the recombinant cell comprises a functional deletion of at least one of a native enoyl-CoA hydratase gene and a native 3-hydroxyacyl-CoA dehydrogenase gene, the recombinant cell comprises at least one of: a functional deletion of a native fadR gene or a homolog thereof; and a recombinant 3-ketoacyl-CoA thiolase gene that encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:22 or SEQ ID NO:24, and the recombinant cell exhibits enhanced production of 2-nonanone with respect to a corresponding native cell.

In some versions, the recombinant cell further comprises a functional deletion of a native 3-ketoacyl-CoA thiolase gene. In some versions, the 3-ketoacyl-CoA thiolase gene comprises at least one of a fadA gene or a homolog thereof and a fadI gene or a homolog thereof.

In some versions, the recombinant cell comprises at least one of: a functional deletion of a native fadR gene or a homolog thereof; a recombinant enoyl-CoA hydratase gene; and a recombinant 3-hydroxyacyl-CoA dehydrogenase gene.

In some versions, the recombinant cell comprises at least one of a recombinant enoyl-CoA hydratase gene and a recombinant 3-hydroxyacyl-CoA dehydrogenase gene. In some versions, the at least one of the recombinant enoyl-CoA hydratase gene and the recombinant 3-hydroxyacyl-CoA dehydrogenase gene encodes at least one of a FadB protein or homolog thereof and a FadJ protein or a homolog thereof. In some versions, the at least one of the recombinant enoyl-CoA hydratase gene and the recombinant 3-hydroxyacyl-CoA dehydrogenase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:14, SEQ ID NO:16, and SEQ ID NO:18.

In some versions, the recombinant cell comprises a recombinant acyl-CoA dehydrogenase gene. In some versions, the recombinant acyl-CoA dehydrogenase gene is a fadE gene or a homolog thereof. In some versions, the recombinant acyl-CoA dehydrogenase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:28 or SEQ ID NO:30.

In some versions, the recombinant β-ketoacyl-CoA thioesterase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:8, the acyl-ACP thioesterase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:2, the recombinant acyl-CoA synthetase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:12, the recombinant cell comprises a functional deletion of a native acyl-CoA dehydrogenase gene, the recombinant cell comprises a recombinant acyl-CoA dehydrogenase gene that encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:30, the recombinant cell comprises a functional deletion of a native 3-ketoacyl-CoA thiolase gene, the recombinant cell comprises at least one of: a functional deletion of a native fadR gene or a homolog thereof; a recombinant enoyl-CoA hydratase gene; and a recombinant 3-hydroxyacyl-CoA dehydrogenase gene, and the recombinant cell exhibits enhanced production of 2-heptanone with respect to a corresponding native cell.

In some versions, the recombinant β-ketoacyl-CoA thioesterase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:8, the acyl-ACP thioesterase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:4, the recombinant cell of any prior claim, wherein the recombinant acyl-CoA synthetase gene encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:10, the recombinant cell comprises a functional deletion of a native acyl-CoA dehydrogenase gene, the recombinant cell comprises a recombinant acyl-CoA dehydrogenase gene that encodes a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:30, the recombinant cell comprises a functional deletion of a native 3-ketoacyl-CoA thiolase gene, the recombinant cell comprises at least one of: a functional deletion of a native fadR gene or a homolog thereof; a recombinant enoyl-CoA hydratase gene encoding a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:16; and a recombinant 3-hydroxyacyl-CoA dehydrogenase gene encoding a protein comprising an amino acid sequence with at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:16, and the recombinant cell exhibits enhanced production of 2-undecanone with respect to a corresponding native cell.

In some versions, the recombinant cell is a bacterium. In some versions, the recombinant cell is an *E coli*.

Another aspect of the invention is directed to methods of producing methyl ketone. In some versions, the methods comprise culturing a recombinant cell as described herein for a time sufficient to produce the methyl ketone. In some versions, the methyl ketone comprises medium-chain methyl ketone. In some versions, the medium-chain methyl ketone comprises at least one of 2-heptanone, 2-nonanone, and 2-undecanone. In some versions, the methods comprise isolating the methyl ketones.

The objects and advantages of the invention will appear more fully from the following detailed description of the preferred embodiment of the invention made in conjunction with the accompanying drawings.

BRIEF DESCRIPTION OF THE DRAWINGS

FIGS. 2A-2B: Sequence similarity of FadM homologs (A). Cluster representation of sequence identity generated using the Enzyme Similarity Tool. A node representing a protein sequence, an edge, which refers to a line connecting between two nodes, representing two connected nodes share similar sequences, clusters representing nodes fall into the different protein families. (B) Pairwise amino acid identity (%) between FadM homologs.

FIG. 3: (A) Scheme describing bioconversion of free fatty acids to methyl ketones. FadM variants were expressed from pTRC99a-"FadM"-FadD6 in strain *E. coli* ΔRAI. (B) FadM activity was tested by feeding even chain-length saturated fatty acids to the culture and measuring the concentration of methyl ketones and free fatty acids over 24 hours. The MK titer is listed in the left column of each pair. A fatty acid consumption rate was calculated from the timecourses presented in FIGS. 4A-4E. Cells were fed 1 g/L octanoic acid, 1 g/L decanoic acid 200 mg/L dodecanoic acid, 100 mg/L tetradecanoic acid, or 100 mg/L hexadecanoic acid. The listed error is the standard deviation of measurements taken from triplicate flasks.

> Fatty acid consumption rate (mg/L/h)=(Initial FFA concentration (mg/L)−FFA concentration (mg/L) at *T* time point)/Time *T* (h), where *T* equals to 6 hrs for octanoic acid and decanoic acid, and *T* equals to 3 hrs for dodecanoic acid, tetradecanoic acid, and hexadecanoic acid.

Figure 5B:
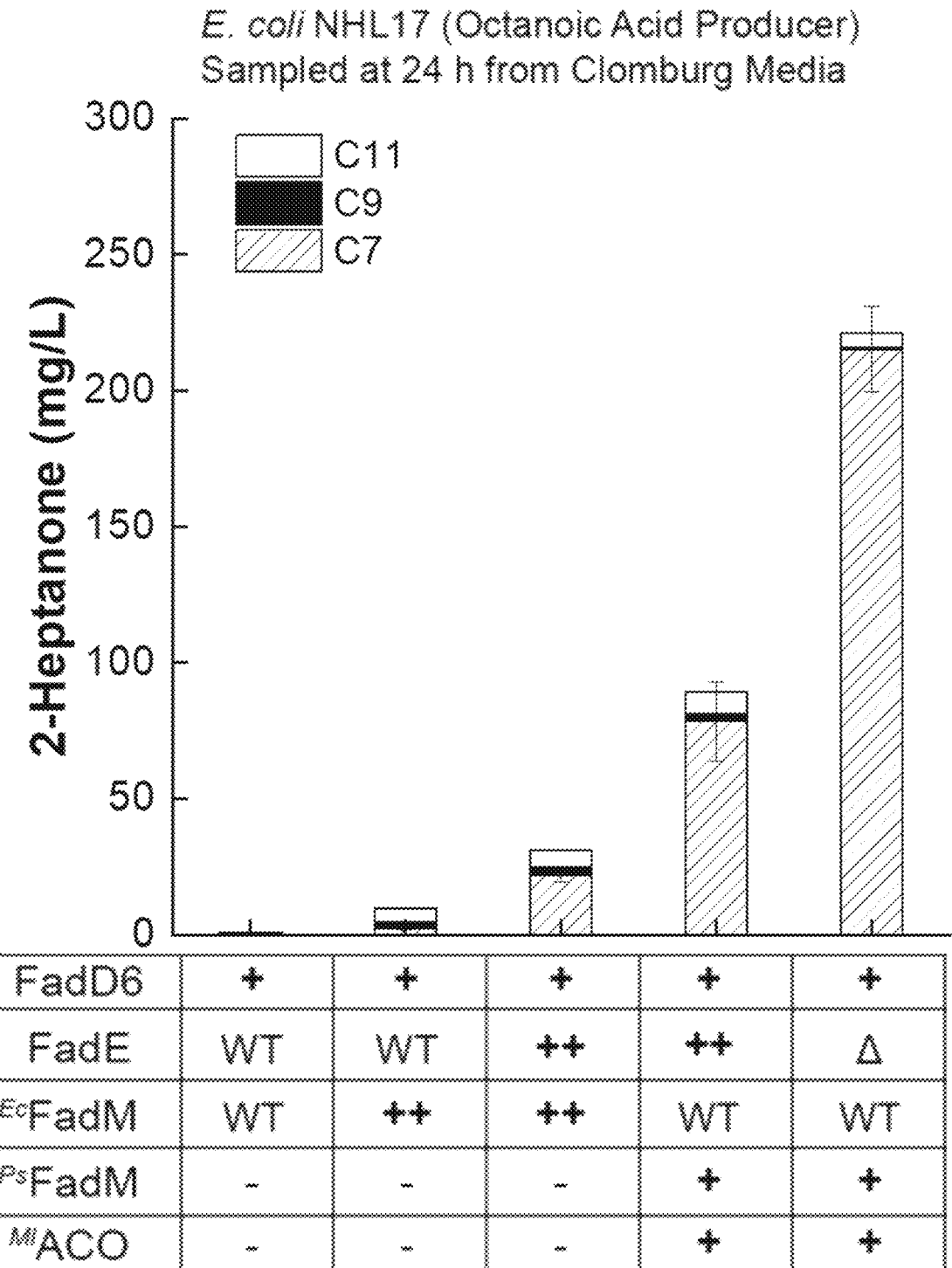

FIGS. 5A-5B: Scheme of genetic design to improve 2-heptanone titer (A), genetic modifications based on strain NHL17 resulted in strain TRS12 (NHL17, ΔfadAEIR) expressing pTRC99a-fadD6-fadM and pACYC-Mlut_11700. Stepwise improvement of 2-heptanone production from engineered *E. coli* NHL17 strains from 20 g/L glycerol in Clomburg medium (B). "WT" refers to native expression of the gene, "+" represents an exogenous gene is overexpressed in a plasmid, "++" represents an endogenous gene has a chromosomal copy and was overexpressed in a plasmid, "-" represents a heterologous gene that was not added, Δ represents a native gene that was removed from the chromosome.

Figure 6A:
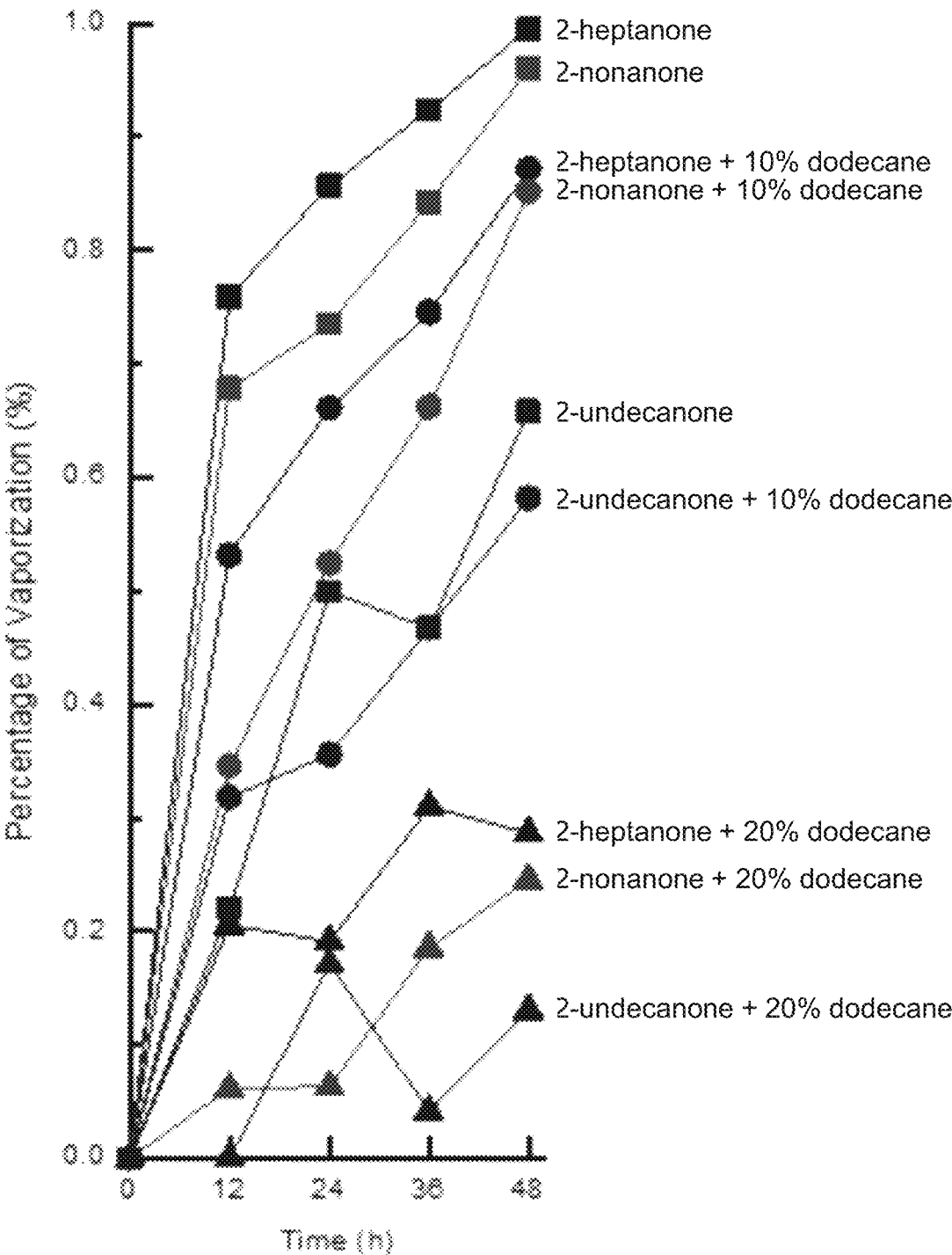
Figures 6B, 6C:
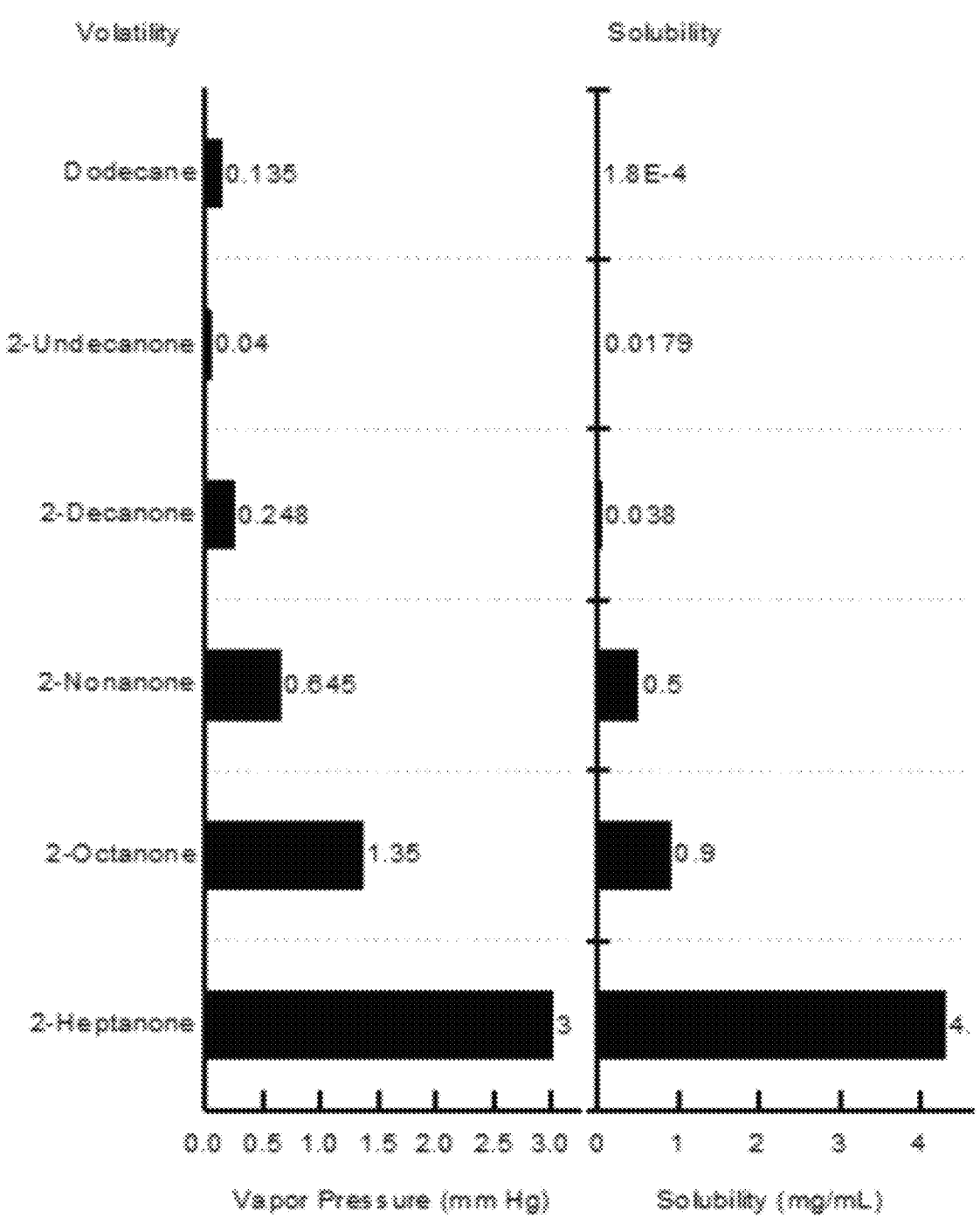

FIGS. 6A-6C: Evaluation of methyl ketone evaporation. (A) 2-heptanone, 2-nonanone and 2-undecanone evaporation was tracked over time to understand evaporation behavior in aerobic conditions. (B) Reported values of vapor pressure of MK and dodecane from PubChem (/pubchem.ncbi.nlm.nih.gov/). Vapor pressure represents the tendency of molecules and atoms to escape from a liquid phase. With exception of reported 2-heptanone vapor pressure measured at 20° C., all reported molecules vapor pressures were measured at 25° C. (C) Reported values of solubility of MK and dodecane in water from PubChem. all reported solubility values were measured at 25 or 30° C.

FIG. 7: (left) Schematic view of the vapor capture system. During fermentation, the bioreactor off-gas flows at 1.5 L/min through a ~7 ft stainless steel coiled condenser and the condensed product is then collected in a stainless-steel holding vessel. Both the condenser and collector are submerged in a water-ice bath and cooled by a 5° C. water line from a separate water cooler. Final condensed products can be released from the collector by opening a ball valve. (right) Vapor condenser setup attached to the bioreactor system.

Figure 8A:
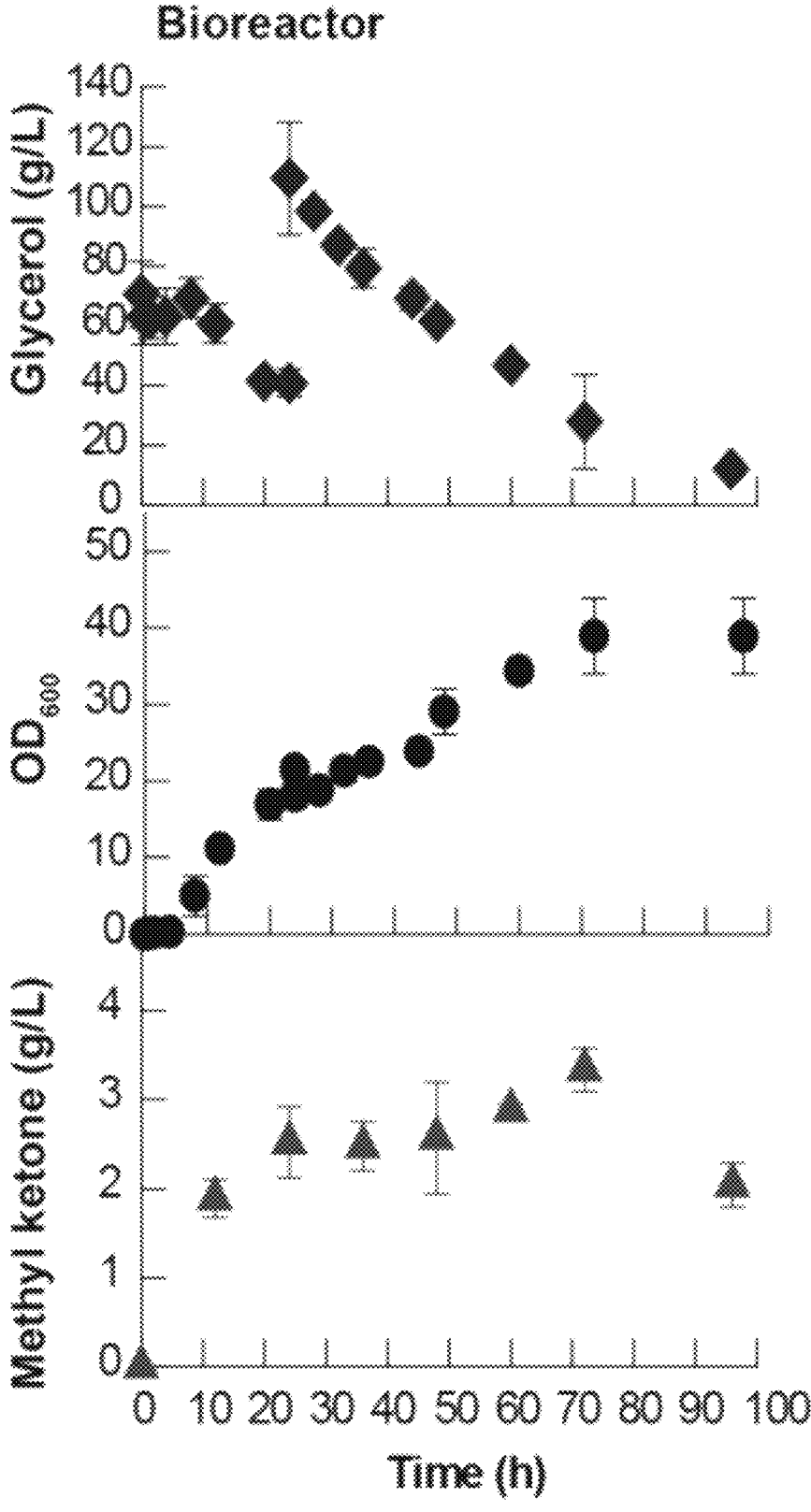
Figure 8B:
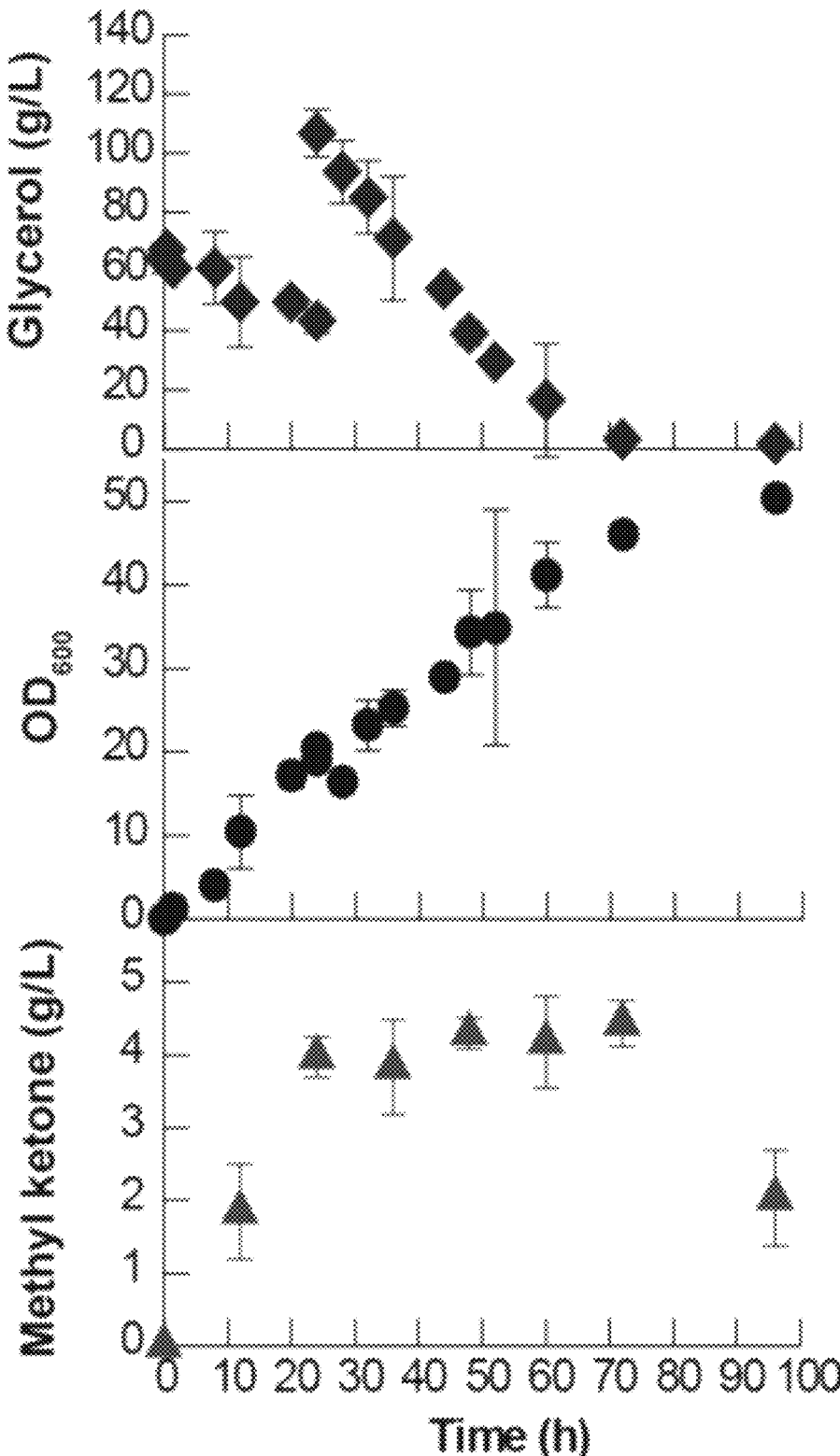
Figure 8C:
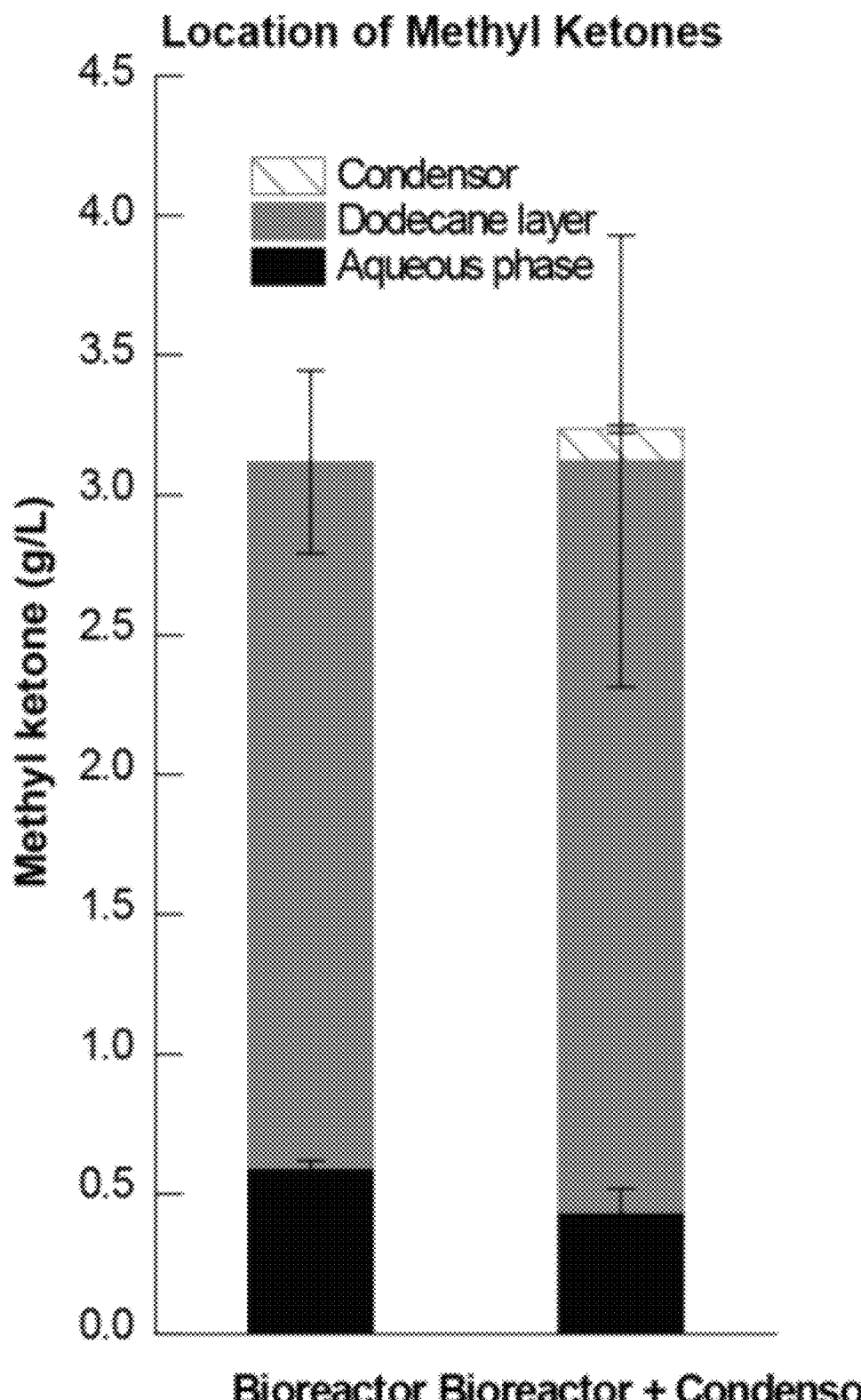

FIGS. 8A-8C: Time course of concentration of glycerol, $OD_{600}$ and total methyl ketone in fed-batch fermentation from bioreactor (A) and bioreactor coupling a condenser (B) using *E. coli* TRS12 strain harbors pTRC99a-FadD6-PsFadM and pACYC-Mlut_11700 plasmids. (C) Evaluation of methyl ketone concentration from samples in dodecane layer, aqueous phase and condenser after 96 h fermentation.

FIGS. 9A-9E: (A) Metabolic pathway for synthesis of 2-nonanone. Strain *E. coli* ΔfadRABIJ expressing pACYC-"fadA"+pTRC99a-FadD6-PsFadM+pBTRCK-CpFatB1*was used for demonstrating 2-nonanone synthesis. Impact of acyl-CoA thiolase homologs on rates of octanoic consumption (B) and 2-nonanone production (C) were evaluated by in vivo feeding 500 mg/L octanoic acid to the culture. The negative control is the strain harbored pACYC empty plasmid. Shake flask batch fermentation for 2-nonanone production was conducted by grown *E. coli* ΔfadABIJR strain that harbors pACYC-ReBktB+pTRC99a-FadD6-PsFadM+pBTRCK-CpFatB1* plasmids in Clomburg medium containing 45 g/L glycerol. Time course of methyl ketone titer (C), glycerol titer and OD600 (D) were monitored every 4-12 hrs. (E) Time course of glycerol titer, $OD_{600}$ and methyl ketone titer in fed-batch fermentation in a bioreactor using the optimized strain. All error bars represent standard deviations calculated from at least three biological replicates. "CupTE*" refers to the CpFatB1* enzyme.

Figure 9B:
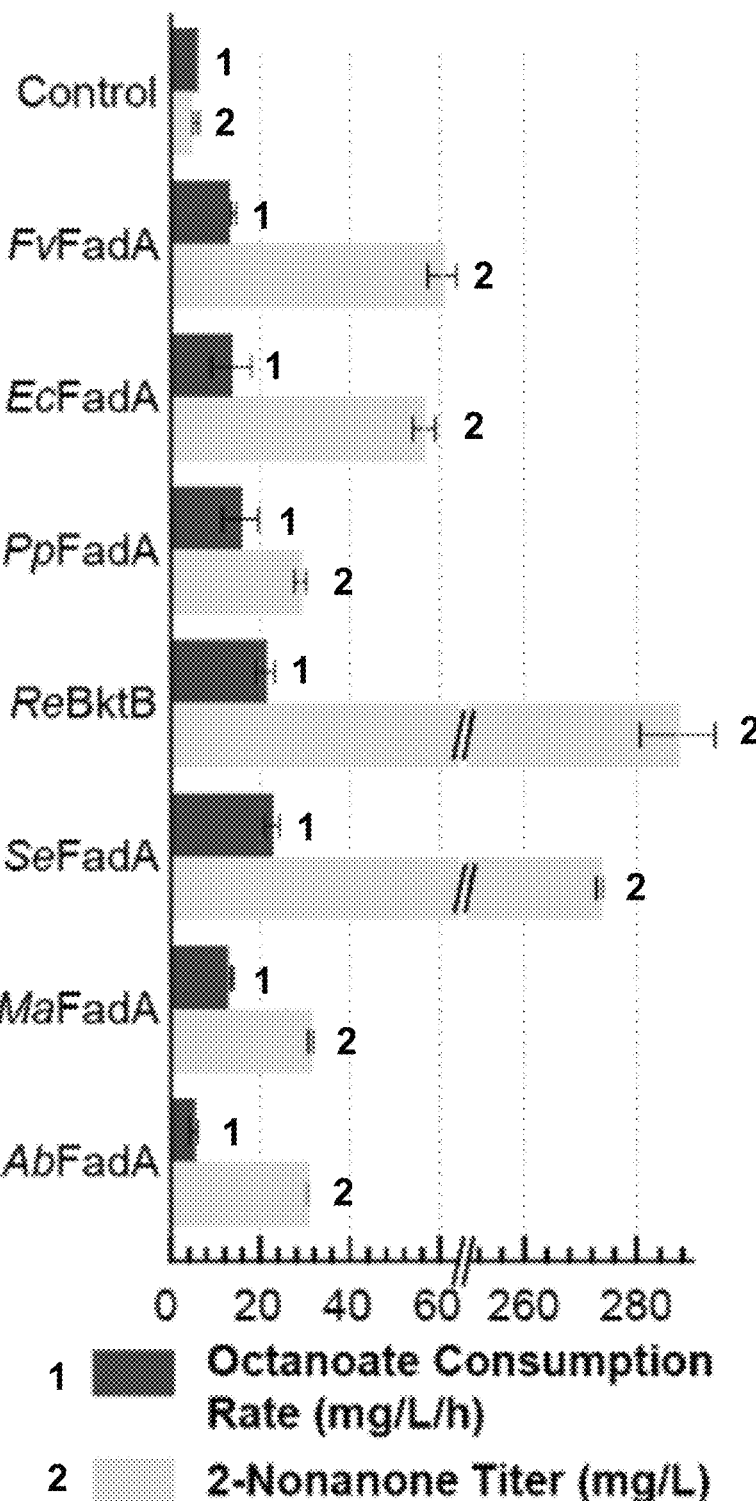
Figure 9C:
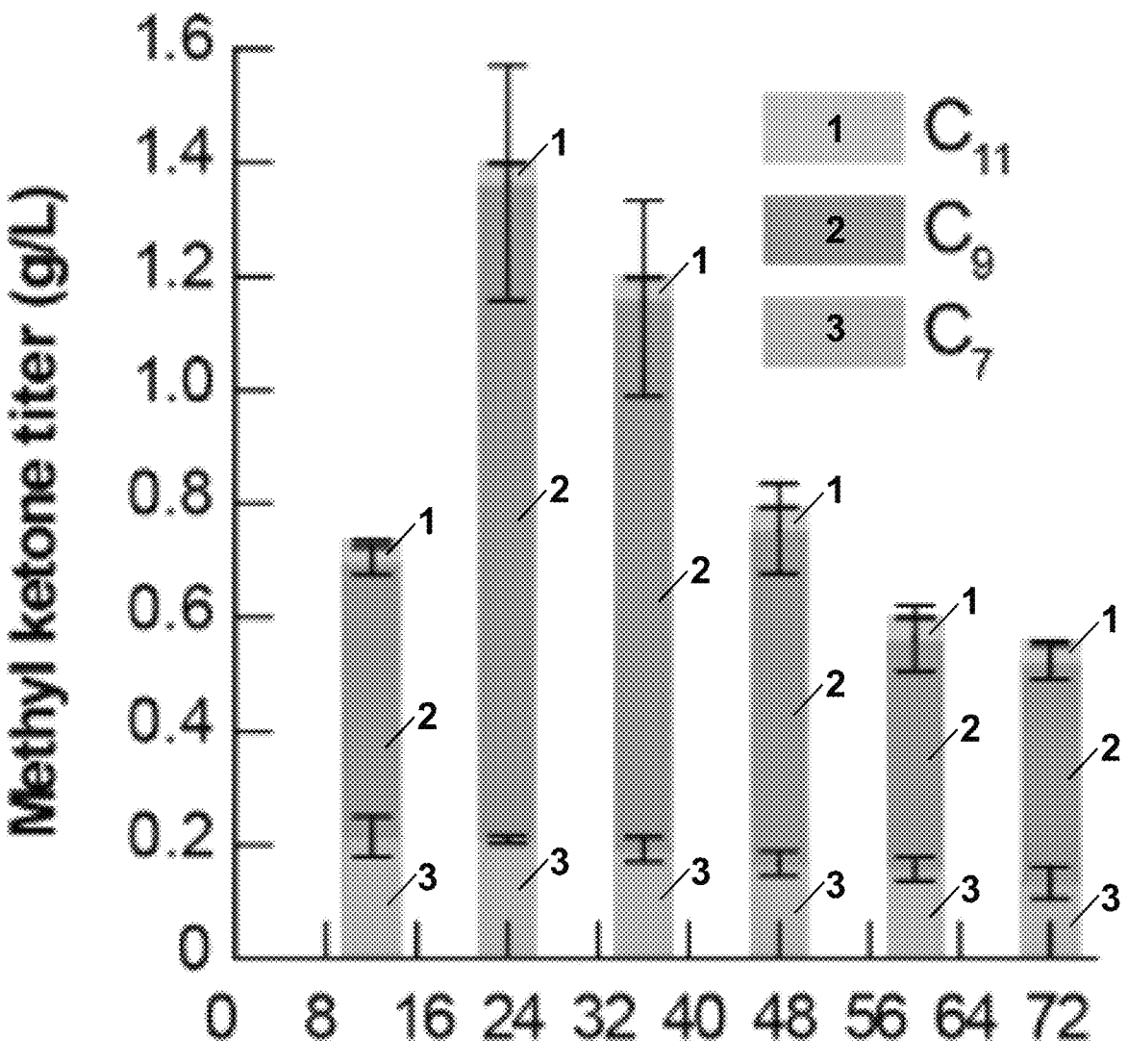
Figure 9D:
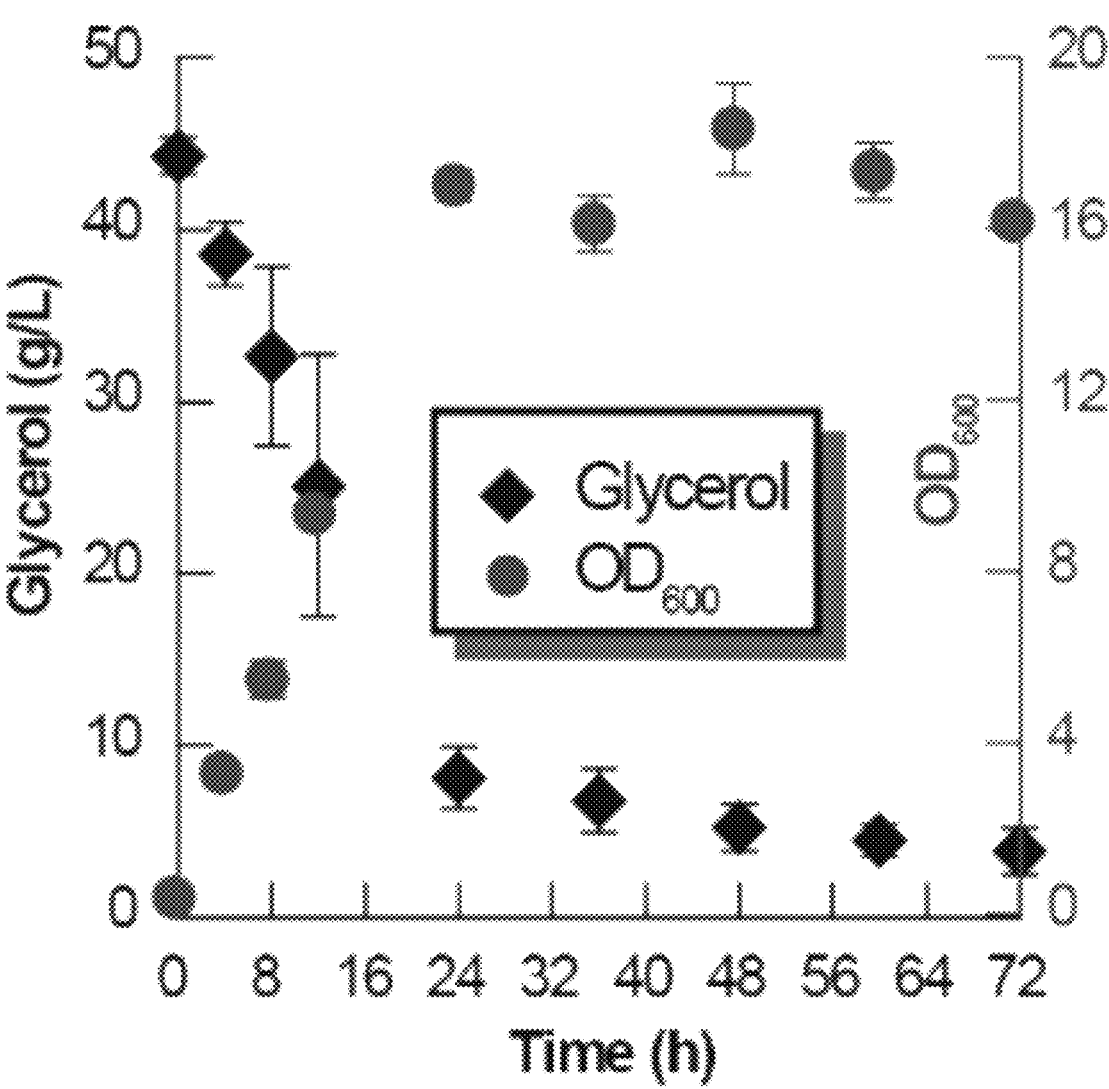
Figure 9E:
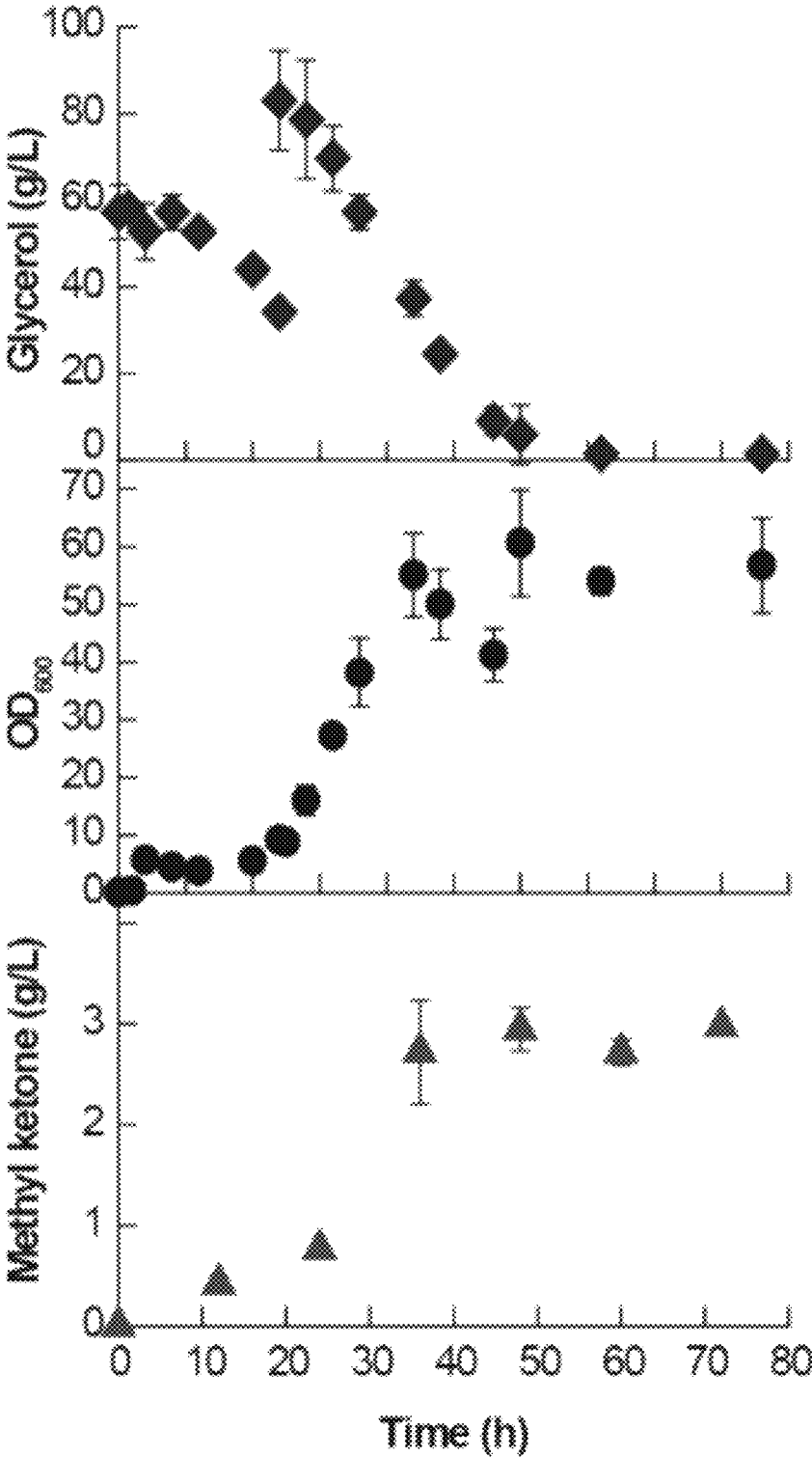
Figure 10A:
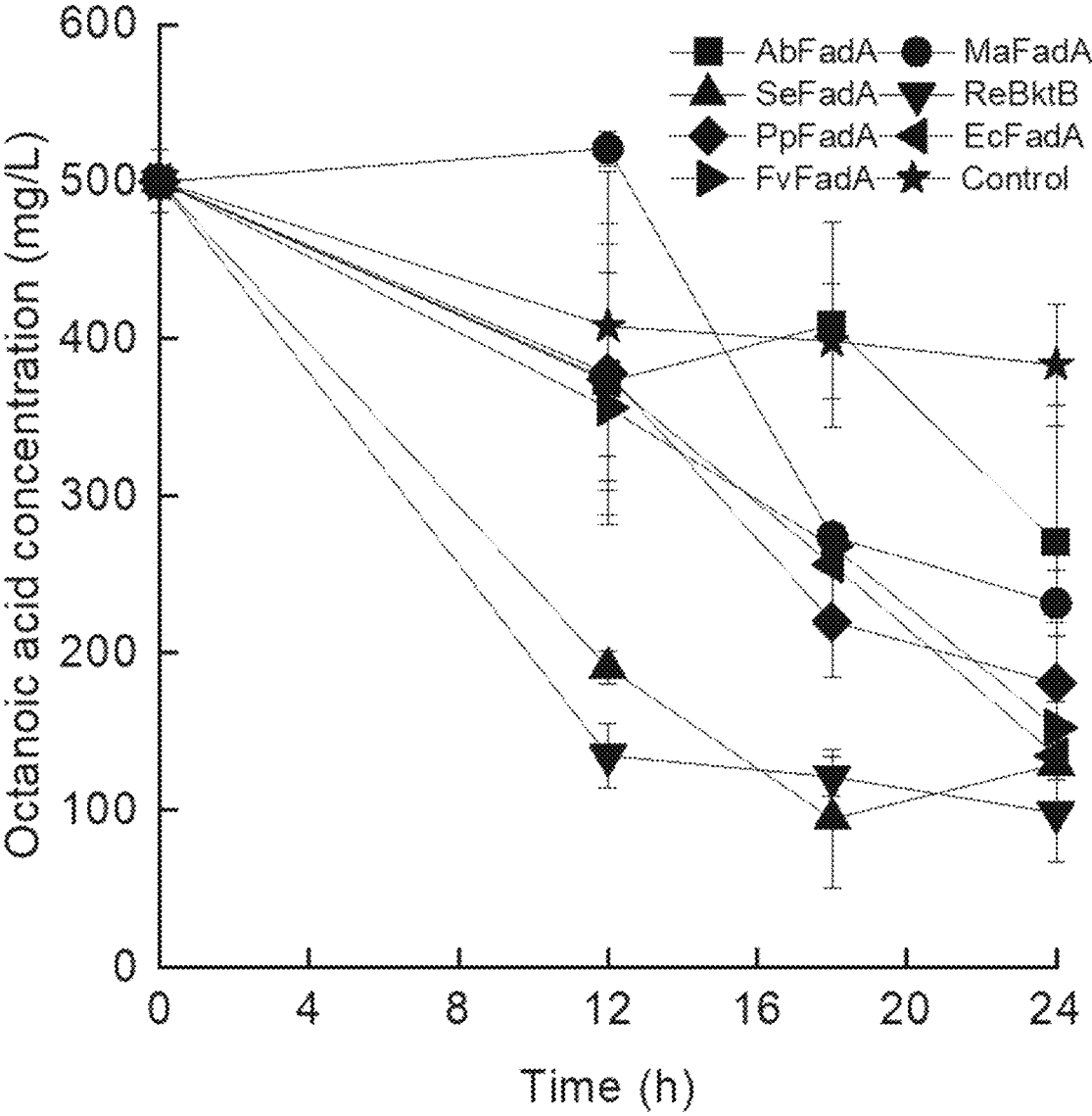
Figure 10B:
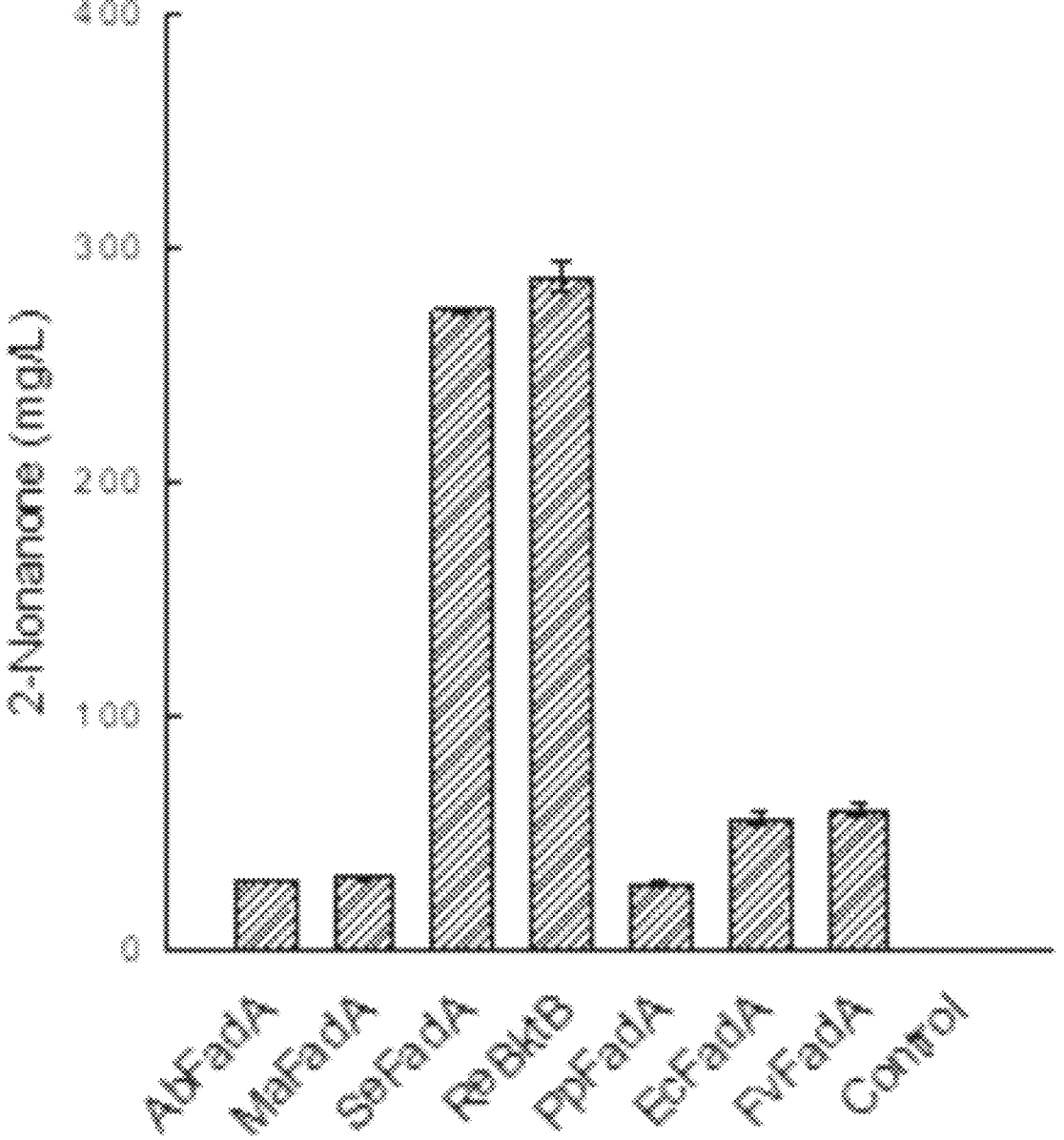
Figure 10C:
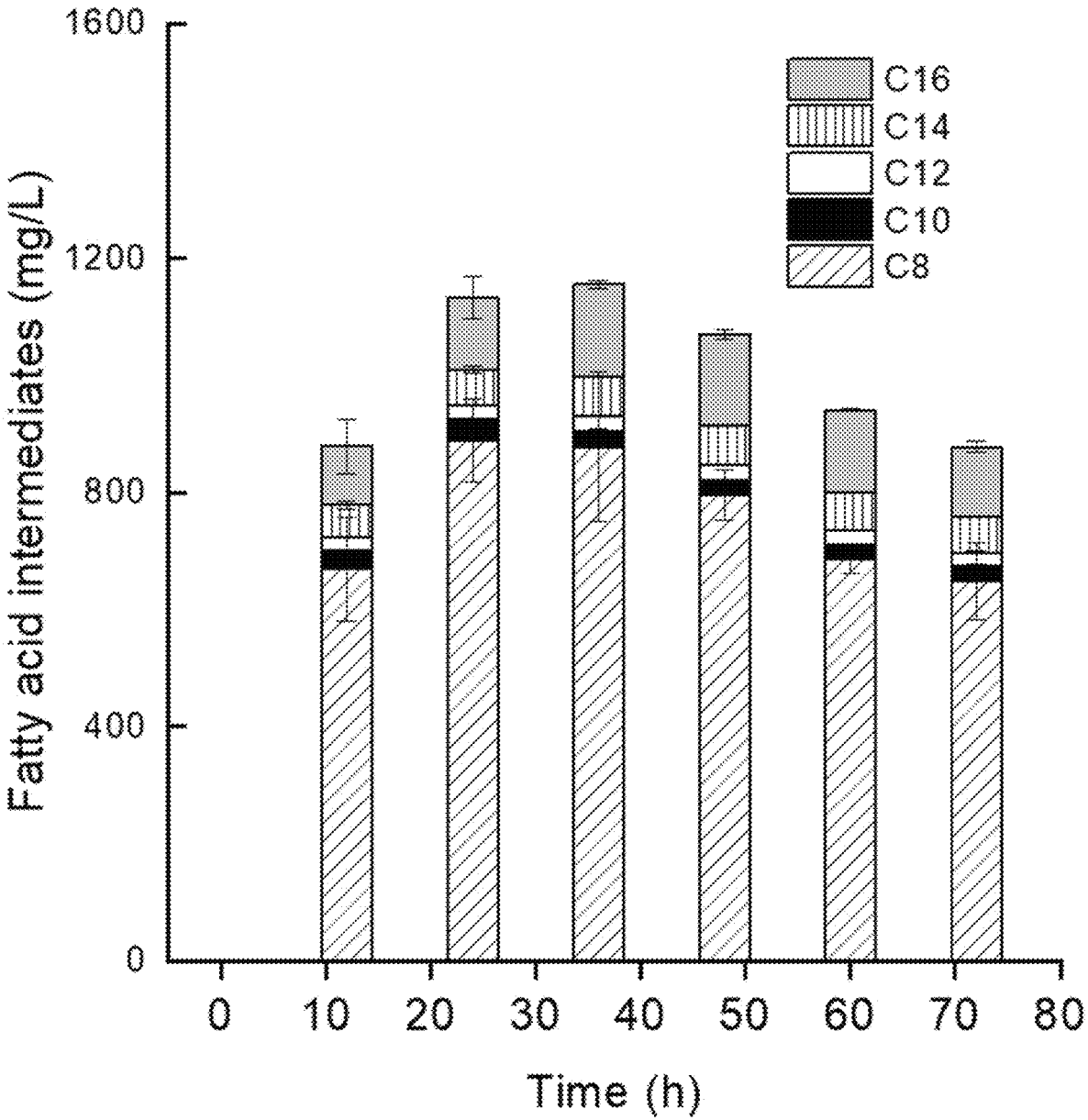

FIGS. 10A-10C: Bioprospecting thiolase variants for use in producing β-ketoacyl-CoAs (A) Time course of octanoic acid consumption and (B) 2-nonanone production when feeding 500 mg/L octanoic acids to cultures of straintrain *E. coli* 4fadRABIJ expressing pACYC-"fadA"+pTRC99a-FadD6-PsFadM+pBTRCK-CpFatB1* (C) Residual free fatty acid titers over time during growth of *E. coli* ΔfadABIJR ptrc99a-PsfadM-fadD6+pACYC-ReBktB+pBTRCK-CpFatB1* in 250 mL shake flasks containing 50 mL Clomburg medium with 45 g/L glycerol (from experiment in FIGS. 9A-9E).

FIGS. 11A-11D: (A) Designed a metabolic pathway for production of 2-undecanone. (B) Comparison of bi-functional 3-hydroxyacyl-CoA dehydratase. *E. coli* TY34 strain harbors pACYC-FadB+pTRC99a-PsfadM+pBTRCK-Mlut_11700 plasmids were grown in Clomburg medium containing 20 g/L glycerol for 24 h. (C) Time course of glycerol consumption and biomass formation, and (D)

methyl ketone production by *E. coli* TY34 strain harbors pACYC-PpFadB+pTRC99a-PsfadM plasmids were grown in Clomburg medium containing 25 g/L glycerol for 72 h.

Figure 11B:
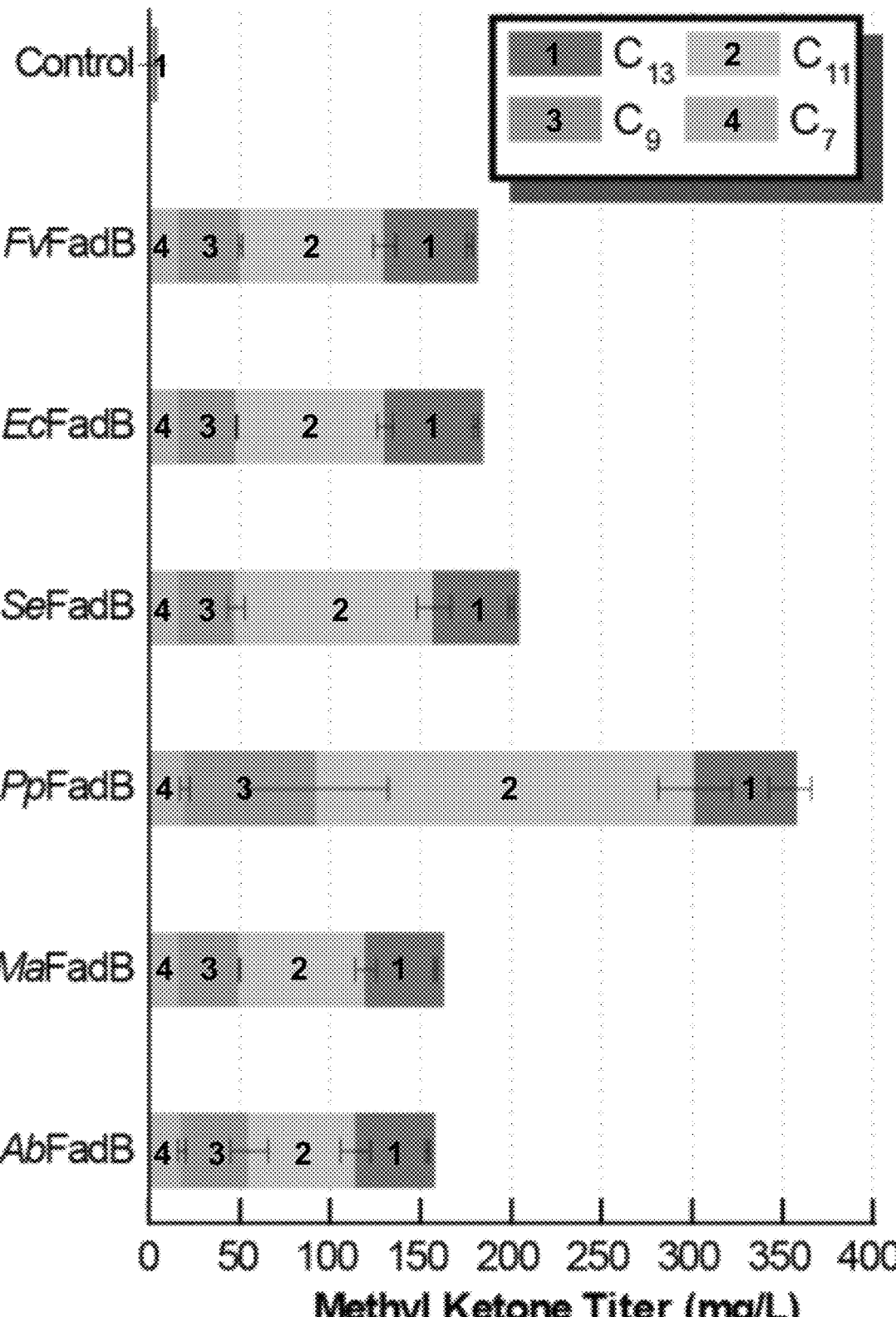
Figure 11C:
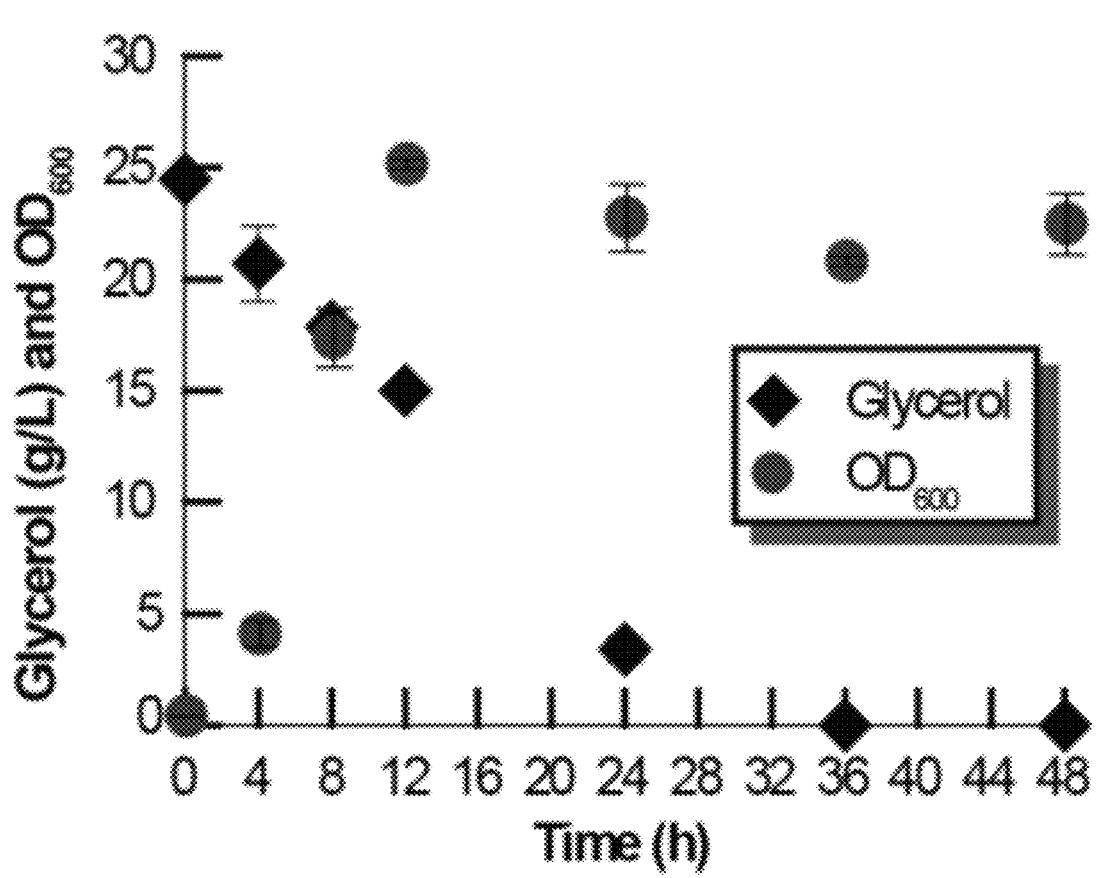
Figure 11D:
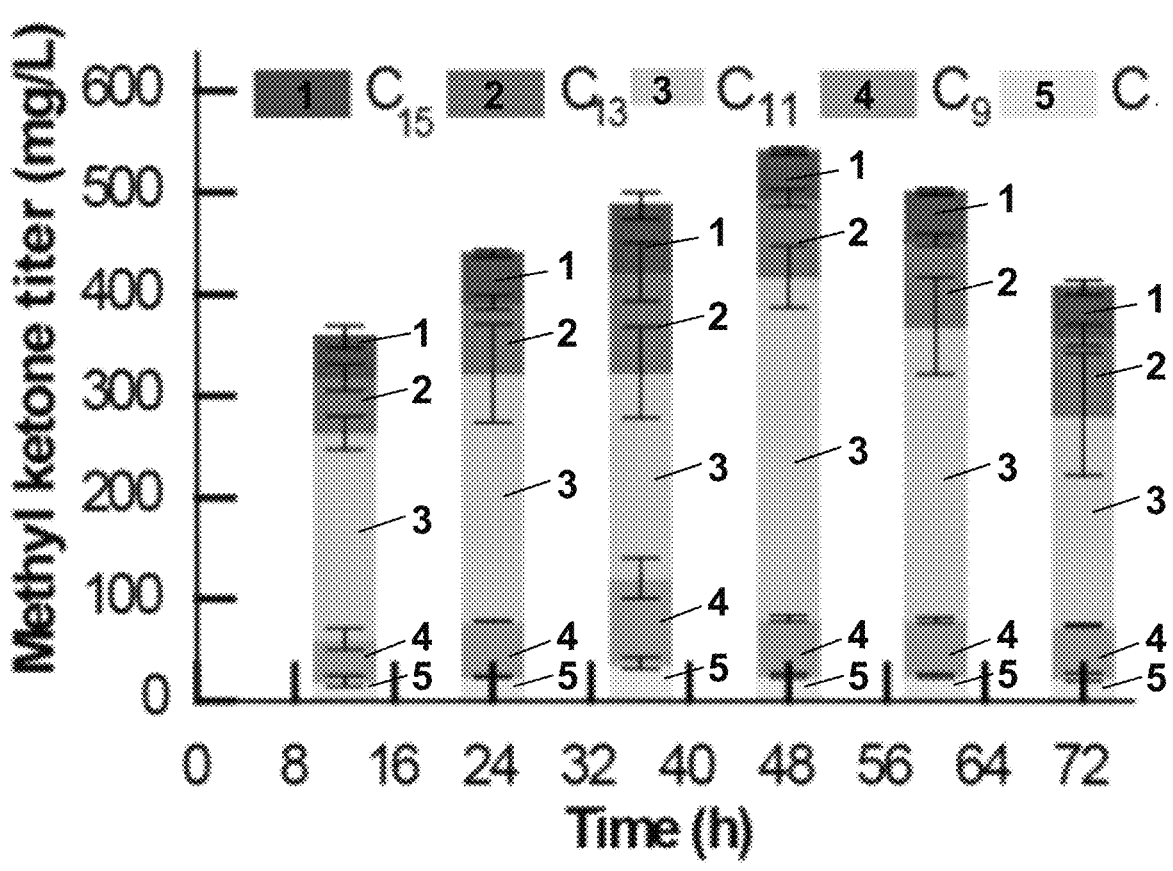
Figure 12:
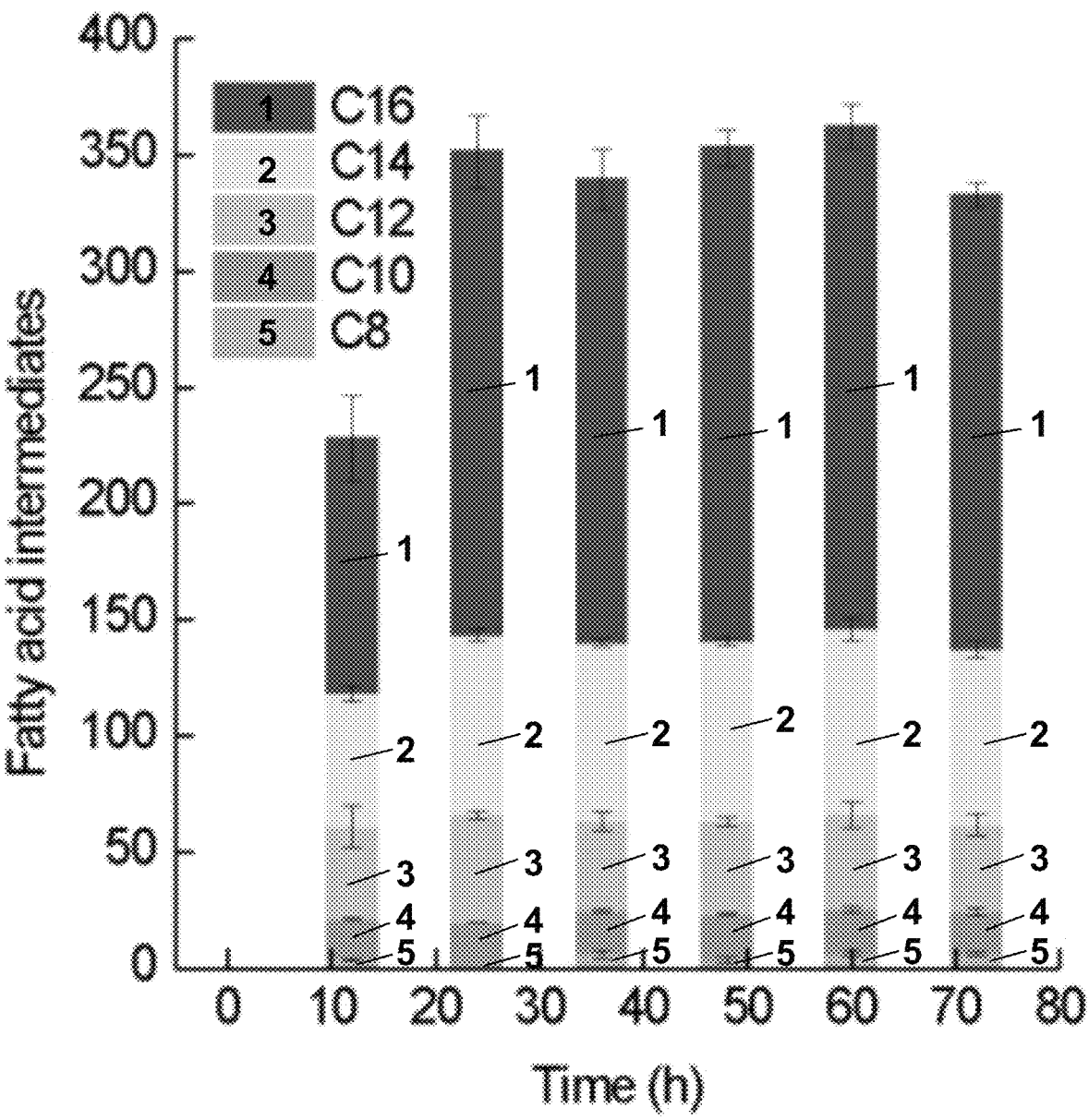

FIG. 12: Residual free fatty acid titers over time during growth of *E. coli* TY34 strain+pACYC-PpFadB+pTRC99a-PsFadM from experiment described in FIGS. 11A-11D.

FIG. 13 shows exemplary routes for increasing production of exemplary methyl ketones. HE refers indicates heterologous expression. The CpFatB* acyl-ACP thioesterase in the −1 pathway can be substituted with the BTE thioesterase or other thioesterases for the production of 2-undecanone.

DETAILED DESCRIPTION OF THE INVENTION

One aspect of the invention is directed to recombinant (non-natural) cells. The recombinant cells are preferably capable of producing methyl ketones. The cells of the present invention may comprise any type of cell that is capable of producing methyl ketones, either naturally or by virtue of genetic engineering. Examples of suitable cells include but are not limited to bacterial cells, yeast cells, fungal cells, insect cells, mammalian cells, and plant cells. Examples of suitable bacterial cells include Gram-positive bacteria such as strains of *Bacillus*, (e.g., *B. brevis* or *B. subtilis*), *Lactobacillus*, *Lactococcus*, or *Streptomyces*, or Gram-negative bacteria, such as strains of *E. coli*, *Salmonella*, *Vibrio*, *Corynebacterium*, *Pseudomonas*, *Ralstonia*, *Aeromonas* or cyanobacteria, or oleaginous bacteria, such as *Rhodococcus opacus*, or *Acinetobacter baylyi*. Examples of suitable yeast cells include strains of *Saccharomyces*, such as *S. cerevisiae* or *Lipomyces starkeyi*; *Schizosaccharomyces*; *Kluyveromyces*; *Pichia*, such as *P. pastoris* or *P. methanolica*, or *P. stipitis*; *Hansenula*, such as *H. Polymorpha*; *Yarrowia*; *Candida*; *Cryptococcus*; Basidiomycete, such as Rhodosporidium. Examples of suitable microalgal species *Chlorophyta*, such as *Chlorella*; Bacillariophyceae, such as *Chaetoceros*. Examples of suitable filamentous fungal cells include strains of *Aspergillus*, e.g., *A. oryzae*, *A. niger*, or *A. nidulans*; *Fusarium* or *Trichoderma*. Examples of suitable insect cells include a *lepidoptera* cell line, such as *Spodoptera frugiperda* (Sf9 or Sf21) or *Trichoplusia ni* cells ("HIGH FIVE"-brand insect cells, Invitrogen, Carlsbad, CA) (U.S. Pat. No. 5,077,214). Examples of suitable mammalian cells include Chinese hamster ovary (CHO) cell lines, e.g., CHO-K1 (ATCC CCL-61); green monkey cell lines, e.g., COS-1 (ATCC CRL-1650) and COS-7 (ATCC CRL-1651); mouse cells, e.g., NS/O; baby hamster kidney (BHK) cell lines, e.g., ATCC CRL-1632 or ATCC CCL-10; and human cells, e.g., HEK 293 (ATCC CRL-1573). Examples of suitable plant cells include those of oilseed crops, including rapeseed, canola, sunflower, soybean, cottonseed, and safflower plants, and cells from other plants such as *Arabidopsis thaliana*. Some of the foregoing cell types are capable of naturally producing methyl ketones, such as certain microorganisms.

In various versions of the invention, the cell is genetically modified to comprise a recombinant gene. "Genetically modified" in this context refers to genetic manipulations of a cell's native genome as well as introduction of genes for heterologous expression. In most cases, the recombinant gene is configured to be expressed or overexpressed in the cell. If a cell endogenously comprises a particular gene, the gene may be modified to exchange or optimize promoters, exchange or optimize enhancers, or exchange or optimize any other genetic element to result in increased expression of the gene. Alternatively, one or more additional copies of the gene or coding sequence thereof may be introduced to the cell for enhanced expression of the gene product. If a cell does not endogenously comprise a particular gene, the gene or coding sequence thereof may be introduced to the cell for heterologous expression of the gene product. The gene or coding sequence may be incorporated into the genome of the cell or may be contained on an extra-chromosomal plasmid. The gene or coding sequence may be introduced to the cell individually or may be included on an operon. Techniques for genetic manipulation are described in further detail below.

In some versions of the invention, the cells are genetically modified to express or overexpress a recombinant thioesterase gene. Thioesterases include enzymes classified into EC 3.1.2.1 through EC 3.1.2.27 based on their activities on different substrates, with many remaining unclassified (EC 3.1.2.-). Thioesterases hydrolyze thioester bonds between acyl chains and CoA or on acyl chains and ACP. These enzymes terminate fatty acid synthesis by removing the CoA or ACP from the acyl chain.

Expression or overexpression of a recombinant thioesterase gene can be used to engineer to produce a homogeneous population of fatty acid products to feed into the methyl ketone synthesis pathways, and thereby produce methyl ketones having a defined side chain length. To engineer a cell for the production of a homogeneous population of fatty acid products, one or more thioesterases with a specificity for a particular carbon chain length or chain lengths can be expressed. Exemplary thioesterases that can be employed for purposes such as this include acyl-acyl carrier protein (acyl-ACP) thioesterases. Suitable acyl-ACP thioesterases include enzymes classified under the EC 3.1.2.21. Exemplary acyl-ACP thioesterases include CpFatB1* as described herein (SEQ ID NO:1 (coding sequence) and SEQ ID NO:2 (protein)), a codon-optimized thioesterase derived from California Bay Laurel (*Umbellularia californica*) thioesterase (BTE), (SEQ ID NO:3 (coding sequence) and SEQ ID NO:4 (protein)), and any of the acyl-ACP thioesterases described in U.S. Pat. No. 10,844, 410, US 2019/0284588, U.S. Pat. No. 10,421,951, and US 2014/0073022, which are incorporated herein by reference in their entireties. Additional exemplary acyl-ACP thioesterases include any of the thioesterases shown in the following table can be expressed individually or in combination to increase production of fatty acid products having specific chain lengths.

Thioesterases.

| Gen Bank Accession Number | Source Organism | Gene | Preferential product produced |
|---|---|---|---|
| AAC73596 | *E. coli* | tesA without leader sequence | $C_8$-$C_{18}$ |
| Q41635; V17097; M94159 | *Umbellularia californica* | fatB | $C_{12:0}$ |
| Q39513 | *Cuphea hookeriana* | fatB2 | $C_{8:0}$-$C_{10:0}$ |
| AAC49269 | *Cuphea hookeriana* | fatB3 | $C_{14:0}$-$C_{16:0}$ |
| Q39473 | *Cinnamonum camphorum* | fatB | $C_{14:0}$ |
| CAA85388 | *Arabidopsis thaliana* | fatB[M141T]* | $C_{16:1}$ |
| NP 189147; NP 193041 | *Arabidopsis thaliana* | fatA | $C_{18:1}$ |
| CAC39106 | *Bradyrhiizobium japonicum* | fatA | $C_{18:1}$ |
| AAC72883 | *Cuphea hookeriana* | fatA | $C_{18:1}$ |

*Mayer et al., *BMC Plant Biology* 7: 1-11, 2007.

Other acyl-ACP thioesterases that can be expressed or overexpressed in the cell include any of the many acyl-ACP thioesterases from *Streptococcus pyogenes*, including any having GenBank Accession Numbers AAZ51384.1, AAX71858.1, AAT86926.1, YP_280213.1, YP_060109.1, YP_006932842.1, YP_005411534.1, AFC68003.1, AFC66139.1, YP_006071945.1, YP_600436.1, AEQ24391.1 and ABF37868.1; a palmitoyl-acyl carrier protein thioesterase from *Ricinus communis*, such as those having GenBank Accession Numbers EEF47013.1, XP_002515564.1, EEF51750.1, XP_002511148.1, and EEF36100.1; a myristoyl-acyl carrier protein thioesterase from *Ricinus communis*, such as those having GenBank Accession Numbers EEF44689.1 and XP_002517525.1; an oleoyl-acyl carrier protein thioesterase from *Ricinus communis*, such as those having GenBank Accession Numbers EEF29646.1 and XP_002532744.1; an acyl-acyl carrier protein thioesterase from *Ricinus communis*, such as that having GenBank Accession Number ABV54795.1; and an acyl-acyl carrier protein thioesterase from *Jatropha curcus*, such as that described in Zhang, X. et al. (2011) *Metab. Eng.* 13, 713-722. These and additional suitable thioesterases that can be expressed or overexpressed in the cell are described in US 2011/0165637 to Pfleger et al.; Lu, X. et al. (2008) *Metab. Eng.* 10, 333-339; Liu, T. et al. (2010) *Metab. Eng.* 12, 378-386; Steen, E. J. et al. (2010) *Nature* 463, 559-562; Lennen, R. M. et al. (2010) *Biotechnol. Bioeng.* 106, 193-202; Lennen, R. M. et al. (2011) *Appl. Environ. Microbiol.* 77, 8114-8128; Youngquist, J. T. et al. (2012) *Biotechnol. Bioeng.* 109, 1518-1527; Jeon, E. et al. (2011) *Enzyme Microb. Technol.* 49, 44-51; Li, M. et al. (2012) *Metab. Eng.* 14, 380-387; Zhang, X. et al. (2012) *Biotechnol. Prog.* 28, 60-65; Zhang, X. et al. (2011) *Metab. Eng.* 13, 713-722; Liu, H. et al. (2012) *Microb. Cell Fact.* 11, 41; Yu, X. et al. (2011) *Proc. Natl. Acad. Sci. U.S.A.* 108, 18643-18648; Dellomonaco, C. et al. (2011) *Nature* 476, 355-359; Zhang, F. et al. (2012) *Nat. Biotechnol.* 30, 354-359; and Lennen et al. (2012) *Trends in Biotechnology* 30(12), 659-667. Yet other suitable thioesterases can be found in the ThYme: Thioester-active Enzymes database at www.enzyme.cbirc.iastate.edu. Homologs of the thioesterases described herein suitable for the use in the present invention can be determined by many known methods, one of which is described below.

In some versions, one or more endogenous thioesterases having a specificity for carbon chain lengths other than the desired product's carbon chain length can be functionally deleted. For example, C10 fatty acid products can be produced by attenuating a thioesterase specific for C18 (for example, accession numbers AAC73596 and POADA1), and expressing a thioesterase specific for C10 (for example, accession number Q39513). This results in a relatively homogeneous population of fatty acid products that have a carbon chain length of 10. In another example, C14 fatty acid products can be produced by attenuating endogenous thioesterases that produce non-C14 fatty acids and expressing the thioesterase with accession number Q39473, which uses C14-acyl carrier protein (ACP) as a substrate. In yet another example, C12 fatty acid products can be produced by expressing thioesterases that use C12-ACP as a substrate (for example, accession number Q41635) and attenuating thioesterases that produce non-C12 fatty acids.

In some versions of the invention, the cells are genetically modified to express or overexpress a recombinant β-ketoacyl-CoA thioesterase gene. β-ketoacyl-CoA thioesterases cleave β-ketoacyl-CoA and/or β-ketoacyl-ACP substrates. Suitable β-ketoacyl-CoA thioesterases include enzymes classified under EC 3.1.2.1 through EC 3.1.2.27, with many remaining unclassified (EC 3.1.2.-). The fadM gene of *E. coli*, for example, is classified under EC 3.1.2.20. β-ketoacyl-CoA thioesterases hydrolyze β-ketoacyl-ACPs. In some versions, the recombinant β-ketoacyl-CoA thioesterase gene is a fadM gene or a homolog thereof. In some versions, the recombinant β-ketoacyl-CoA thioesterase gene encodes a FadM protein or a homolog thereof. Exemplary β-ketoacyl-CoA thioesterase genes include fadM of *E. coli* (SEQ ID NO:5 (coding sequence) and SEQ ID NO:6 (protein), fadM of *Providencia sneebia* (SEQ ID NO:7 (coding sequence) and SEQ ID NO:8 (protein)), fadM of *Salmonella enterica* (SEQ ID NO:33 (coding sequence) and SEQ ID NO:34 (protein)), fadM of *Cucumis sativus* (SEQ ID NO:35 (coding sequence) and SEQ ID NO:36 (protein)), fadM of *Cronobacter turicensis* (SEQ ID NO:37 (coding sequence) and SEQ ID NO:38 (protein)), fadM of *Beauveria bassiana* (SEQ ID NO:39 (coding sequence) and SEQ ID NO:40 (protein)), fadM of *Buttiauxella agrestis* (SEQ ID NO:41 (coding sequence) and SEQ ID NO:42 (protein)), fadM of *Serratia odorifera* (SEQ ID NO:43 (coding sequence) and SEQ ID NO:44 (protein)), fadM1 of *Mycobacterium tuberculosis* (SEQ ID NO:45 (coding sequence) and SEQ ID NO:46 (protein)), fadM4 of *Mycobacterium tuberculosis* (SEQ ID NO:47 (coding sequence) and SEQ ID NO:48 (protein)), fadM5 of *Mycobacterium tuberculosis* (SEQ ID NO:49 (coding sequence) and SEQ ID NO:50 (protein)), fadM of *Neisseria gonorrhoeae* (SEQ ID NO:51 (coding sequence) and SEQ ID NO:52 (protein)), fadM of *Marinomonas ushuaiensis* (SEQ ID NO:53 (coding sequence) and SEQ ID NO:54 (protein)), fadM2 of *Mycobacterium tuberculosis* (SEQ ID NO:55 (coding sequence) and SEQ ID NO:56 (protein)), fadM of *Pseudomonas aeruginosa* (SEQ ID NO:57 (coding sequence) and SEQ ID NO:58 (protein)), and fadM3 of *Mycobacterium tuberculosis* (SEQ ID NO:59 (coding sequence) and SEQ ID NO:60 (protein)). Homologs of the above-mentioned β-ketoacyl-CoA thioesterase genes suitable for use in the present invention can be determined by many known methods, one of which is described below.

In some versions of the invention, the cells are genetically modified to express or overexpress a recombinant acyl-CoA synthetase gene. This is thought to constitute a mechanism of modifying cells to enhance entry of carbon substrates into the β-oxidation pathway. In some versions, the recombinant acyl-CoA synthetase gene is a fadD gene or a homolog thereof. In some versions, the recombinant acyl-CoA synthetase gene encodes a FadD protein or a homolog thereof. Suitable acyl-CoA synthetases include enzymes classified under the EC 6.2.1.-, such as EC 6.2.1.3. Acyl-CoA synthetases catalyze the conversion of free fatty acids, coenzyme A, and ATP to fatty acyl CoAs plus AMP (Black et al. 1992, *J. Biol. Chem.* 267:25513-25520). Examples of suitable genes for acyl CoA synthetases include fadD from *E. coli* (SEQ ID NO:9 (coding sequence) and SEQ ID NO:10 (protein); GenBank NC 000913.2 at 1886085-1887770 (complement)) (Black et al. 1992, *J. Biol. Chem.* 267:25513-25520), fadD6 from *Mycobacterium tuberculosis* (SEQ ID NO:11 (coding sequence) and SEQ ID NO:12 (protein), alkK from *Pseudomonas oleovorans* (GenBank AJ245436.1 at 13182-14822) (van Beilen et al. 1992, *Molecular Microbiology* 6:3121-3136), Pfacs1 from *Plasmodium falciparum* (GenBank AF007828.2) (Matesanz et al. 1999, *J Mol. Biol.* 291:59-70), and PP_0763 (KEGG) from *P. putida* (SEQ ID NO:13 (coding sequence) and SEQ ID NO:14 (protein)), described herein. Methods and materials for identification of other suitable acyl-CoA synthetases are described in U.S. Pat. No. 7,786,355.

In some versions of the invention, the cells are genetically modified to express or overexpress a recombinant enoyl-CoA hydratase gene. Enoyl-CoA hydratases include enzymes classified under Enzyme Commission (EC) number 4.2.1.17. Enoyl-CoA hydratases catalyze the conversion of trans-2(or 3)-enoyl-CoA to (3S)-3-hydroxyacyl-CoA in the β-oxidation pathway. The term "enoyl-CoA hydratase" used herein without an indication of stereospecificity refers to the enzymes under EC 4.2.1.17 that produce (3S)-3-hydroxyacyl-CoA. These enzymes are distinct from the enzymes that produce (3R)-3-hydroxyacyl-CoA and are designated under EC 4.2.1.119, which are referred to herein as "R-specific enoyl-CoA hydratases." In some versions, the recombinant enoyl-CoA hydratase gene is a fadB gene, a fadJ gene, a homolog of any one or more of the foregoing, or any combination thereof. In some versions, the recombinant enoyl-CoA hydratase gene encodes a FadB protein, a FadJ protein, a homolog of any one or more of the foregoing, or any combination thereof. Examples of enoyl-CoA hydratase genes in bacteria include fadB of *E. coli* (SEQ ID NO:13 (coding sequence) and SEQ ID NO:14 (protein); GenBank NC_000913.2 at 4026805-4028994 (complement)), fadB of *Pseudomonas putida* (SEQ ID NO:15 (coding sequence) and SEQ ID NO:16 (protein)), and fadJ of *E. coli* (SEQ ID NO:17 (coding sequence) and SEQ ID NO:18 (protein); GenBank NC_000913.2 at 2455037-2457181 (complement)). Examples of enoyl-CoA hydratase genes in yeast include FOX2 (GenBank NC_001143 at 454352-457054 (complement)) or the enzyme encoded by Kyoto Encyclopedia of Genes and Genomes (KEGG) (www.genome.jp/kegg/) entry number NCU06488. An example of enoyl-CoA hydratase genes in filamentous fungal cells includes the enzyme encoded by KEGG entry number AN5916.2. An example of an enoyl-CoA hydratase gene in insect cells is Mfe2 (GenBank NM_132881.2). Examples of enoyl-CoA hydratase genes in mammalian cells include ECHS1 (GenBank NM_004092.3), EHHADH (GenBank NM_001966.3), and HADHA (GenBank NM_000182.4). Examples of enoyl-CoA hydratase genes in plants include MFP2 (GenBank NM_111566.3) and AIM1 (GenBank NM_119045.4). Homologs of the above-mentioned enoyl-CoA hydratase genes suitable for use in the present invention can be determined by many known methods, one of which is described below.

In some versions of the invention, the cells are genetically modified to express or overexpress a recombinant 3-hydroxyacyl-CoA dehydrogenase gene. 3-Hydroxyacyl-CoA dehydrogenases include enzymes classified under EC number 1.1.1.35. 3-Hydroxyacyl-CoA dehydrogenases catalyze the conversion of (3S)-3-hydroxyacyl-CoA to 3-ketoacyl CoA in the β-oxidation pathway. In some versions, the recombinant 3-hydroxyacyl-CoA dehydrogenase gene is a fadB gene, a fadJ gene, a homolog of any one or more of the foregoing, or any combination thereof. In some versions, the recombinant 3-hydroxyacyl-CoA dehydrogenase gene encodes a FadB protein, a FadJ protein, a homolog of any one or more of the foregoing, or any combination thereof. Examples of 3-hydroxyacyl-CoA dehydrogenase genes in bacteria include fadB of *E. coli* (SEQ ID NO:13 (coding sequence) and SEQ ID NO:14 (protein); GenBank NC_000913.2 at 4026805-4028994 (complement)), fadB of *Pseudomonas putida* (SEQ ID NO:15 (coding sequence) and SEQ ID NO:16 (protein)), and fadJ of *E. coli* (SEQ ID NO:17 (coding sequence) and SEQ ID NO:18 (protein); GenBank NC_000913.2 at 2455037-2457181 (complement)). An example of a 3-hydroxyacyl-CoA dehydrogenase gene in yeast includes FOX2 (GenBank NC_001143 at 454352-457054 (complement)). An example of a 3-hydroxyacyl-CoA dehydrogenase gene in filamentous fungal cells includes the enzyme encoded by KEGG entry number AN7238.2. An example of a 3-hydroxyacyl-CoA dehydrogenase gene in insect cells is Mfe2 (GenBank NM_132881.2). Examples of 3-hydroxyacyl-CoA dehydrogenase genes in mammalian cells include EHHADH (GenBank NM_001966.3), HSD17B10 (GenBank NG 008153.1), HADH (GenBank NM_001184705.2), and HSD17B4 (GenBank NG 008182.1). Examples of 3-hydroxyacyl-CoA dehydrogenase genes in plants include MFP2 (GenBank NM_111566.3) and AIM1 (GenBank NM_119045.4). Homologs of the above-mentioned 3-hydroxyacyl-CoA dehydrogenase genes suitable for use in the present invention can be determined by many known methods, one of which is described below.

In some versions of the invention, the cells are genetically modified to express or overexpress a recombinant 3-ketoacyl-CoA thiolase gene. 3-Ketoacyl-CoA thiolases include enzymes classified under EC number 2.3.1.16. 3-Ketoacyl-CoA thiolases catalyze the conversion of 3-ketoacyl CoA to acetyl-CoA and a shortened acyl-CoA species in the (3-oxidation pathway. In some versions, the recombinant 3-ketoacyl-CoA thiolase gene is a fadA gene, a fadI gene, a bktB gene, a homolog of any one or more of the foregoing, or any combination thereof. In some versions, the recombinant 3-ketoacyl-CoA thiolase gene encodes a FadA protein, a FadI protein, a BktB protein, a homolog of any one or more of the foregoing, or any combination thereof. Examples of 3-ketoacyl-CoA thiolase genes in bacteria include fadA of *E. coli* (SEQ ID NO:19 (coding sequence) and SEQ ID NO:20 (protein); GenBank NC_000913.2 at 4025632-4026795 (complement)), bktB of *Ralstonia eutropha* (SEQ ID NO:21 (coding sequence) and SEQ ID NO:22 (protein)), fadA of *Salmonella enterica* (SEQ ID NO:23 (coding sequence) and SEQ ID NO:24 (protein)), and fadI of *E. coli* (SEQ ID NO:25 (coding sequence) and SEQ ID NO:26 (protein); GenBank NC_000913.2 at 2457181-2458491 (complement)). An example of a 3-ketoacyl-CoA thiolase gene in yeast includes FOX3 (GenBank NM_001179508.1). Examples of 3-ketoacyl-CoA thiolase genes in filamentous fungal cells include the enzymes encoded by KEGG entry numbers AN5646.2 and AN5698.2. An example of a 3-ketoacyl-CoA thiolase gene in insect cells is gene yip2 (GenBank NM_078804.3). Examples of 3-ketoacyl-CoA thiolase genes in mammalian cells include ACAA1 (GenBank NR 024024.1), ACAA2 (GenBank NM_006111.2), and HADHB (GenBank NG 007294.1). Examples of 3-ketoacyl-CoA thiolase genes in plants include PKT4 (GenBank NM_100351.4), PKT3 (GenBank NM_128874.3), and PKT2 (GenBank NM_180826.3). Homologs of the above-mentioned 3-ketoacyl-CoA thiolase genes suitable for use in the present invention can be determined by many known methods, one of which is described below.

In some versions of the invention, the cells are genetically modified to express or overexpress a recombinant acyl-CoA dehydrogenase gene. Acyl-CoA dehydrogenases include enzymes classified under EC number 1.3.8.-. Acyl-CoA dehydrogenases dehydrogenate acyl-CoA to dehydroacyl-CoA. Acyl-CoA dehydrogenases are also referred to as acyl-CoA oxidases. In some versions, the recombinant acyl-CoA dehydrogenase gene is a fadE gene or a homolog thereof. In some versions, the recombinant acyl-CoA dehydrogenase gene encodes a FadE protein or a homolog thereof. Examples of acyl-CoA dehydrogenase genes include fadE of *E. coli* (SEQ ID NO:27 (coding sequence) and SEQ ID NO:28 (protein) and the acyl-CoA oxidase from

*Micrococcus luteus* (SEQ ID NO:29 (coding sequence) and SEQ ID NO:30 (protein). Homologs of the above-mentioned acyl-CoA dehydrogenase genes suitable for use in the present invention can be determined by many known methods, one of which is described below.

The recombinant cells of the invention preferably have one or more genes functionally deleted to inhibit consumption of substrates for methyl ketone production. "Functional deletion" or its grammatical equivalents refers to any modification to a microorganism that ablates, reduces, inhibits, or otherwise disrupts production of a gene product, renders the gene product non-functional, or otherwise reduces or ablates the gene product's activity. "Gene product" refers to a protein or polypeptide encoded and produced by a particular gene. In some versions of the invention, functionally deleting a gene product or homolog thereof means that the gene is mutated to an extent that corresponding gene product is not produced at all.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations, partial or complete deletions, insertions, and/or other variations to a coding sequence or a sequence controlling the transcription or translation of a coding sequence; placing a coding sequence under the control of a less active promoter; and expressing ribozymes or antisense sequences that target the mRNA of the gene of interest, etc. In some versions, a gene or coding sequence can be replaced with a selection marker or screenable marker. The genetic modifications that functionally delete a product of a particular gene can be cis-acting modifications (direct modifications of the particular gene itself) or trans-actin modifications (modifications other than to the particular gene itself that indirectly affect the gene). Various methods for introducing the genetic modifications described above are well known in the art and include homologous recombination, among other mechanisms. See, e.g., Green et al., *Molecular Cloning: A laboratory manual*, 4ᵗʰ ed., Cold Spring Harbor Laboratory Press (2012) and Sambrook et al., *Molecular Cloning: A Laboratory Manual*, 3ʳᵈ ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small-molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding cell. In certain versions, the genetic modifications giving rise to a functionally deleted gene product are determined with respect to the gene in its unaltered state as found in nature. In certain versions, the genetic modifications giving rise to a functionally deleted gene product are determined with respect to the gene in its form in a corresponding cell. As used herein, "corresponding cell" refers to a cell of the same species having the same or substantially same genetic and proteomic composition as a cell of the invention, with the exception of any genetic and proteomic differences resulting from the modifications described herein in any particular embodiments of the invention. In some versions, the corresponding cell is the native version of a given recombinant cell.

In some versions of the invention, an enoyl-CoA hydratase gene is functionally deleted. The functionally deleted enoyl-CoA hydratase can include any enoyl-CoA hydratase described herein or any homolog thereof. In some versions, the functionally deleted enoyl-CoA hydratase is encoded by a fadB gene, a fadJ gene, a homolog of any one or more of the foregoing, or any combination thereof. In some versions, the functionally deleted enoyl-CoA hydratase is a FadB protein, a FadJ protein, a homolog of any one or more of the foregoing, or any combination thereof. In some versions, the functionally deleted enoyl-CoA hydratase has a sequence comprising SEQ ID NO:14, a sequence comprising SEQ ID NO:16, a sequence comprising SEQ ID NO:18, a sequence homologous to any one or more of the foregoing, or any combination thereof.

In some versions of the invention, a 3-hydroxyacyl-CoA dehydrogenase gene is functionally deleted. The functionally deleted 3-hydroxyacyl-CoA dehydrogenase can include any 3-hydroxyacyl-CoA dehydrogenase described herein or any homolog thereof. In some versions, the functionally deleted 3-hydroxyacyl-CoA dehydrogenase is encoded by a fadB gene, a fadJ gene, a homolog of any one or more of the foregoing, or any combination thereof. In some versions, the functionally deleted 3-hydroxyacyl-CoA dehydrogenase is a FadB protein, a FadJ protein, a homolog of any one or more of the foregoing, or any combination thereof. In some versions, the functionally deleted 3-hydroxyacyl-CoA dehydrogenase has a sequence comprising SEQ ID NO:14, a sequence comprising SEQ ID NO:16, a sequence comprising SEQ ID NO:18, a sequence homologous to any one or more of the foregoing, or any combination thereof.

In some versions of the invention, a 3-ketoacyl-CoA thiolase is functionally deleted. The functionally deleted 3-ketoacyl-CoA thiolase can include any 3-ketoacyl-CoA thiolase described herein or any homolog thereof. In some versions, the functionally deleted 3-ketoacyl-CoA thiolase is encoded by a fadA gene, a fadI gene, a bktB gene, a homolog of any one or more of the foregoing, or any combination thereof. In some versions, the functionally deleted 3-ketoacyl-CoA thiolase is a FadA protein, a FadI protein, a BktB protein, a homolog of any one or more of the foregoing, or any combination thereof. In some versions, the functionally deleted 3-ketoacyl-CoA thiolase has a sequence comprising SEQ ID NO:20, a sequence comprising SEQ ID NO:22, a sequence comprising SEQ ID NO:24, a sequence comprising SEQ ID NO:26, a sequence homologous to any one or more of the foregoing, or any combination thereof.

Production of methyl ketones can be enhanced when the β-oxidation pathway is maximally shut down at a particular step. When a cell has more than one enzyme catalyzing a step in the β-oxidation pathway, i.e., enoyl-CoA hydration, (3S)-hydroxyacyl-CoA dehydrogenation, or ketoacyl-CoA thiolation, it is preferred that more than one enzyme catalyzing that step is functionally deleted. It is more preferred that all enzymes catalyzing that step are functionally deleted. In the case of *E. coli*, for example, it is preferred that products of both fadA and fadI or both fadB and fadJ are functionally deleted.

In some versions of the invention, one or more factors that regulate expression of β-oxidation genes in the cells are functionally deleted. In preferred bacterial cells such as *Escherichia coli*, this is accomplished by functionally deleting the product of fadR (SEQ ID NO:31 (coding sequence) and SEQ ID NO:32 (protein); GenBank NC_000913.2 at 1234161-1234880). FadR encodes a transcription factor (FadR) that coordinately regulates the machinery required for β-oxidation and the expression of a key enzyme in fatty acid biosynthesis. FadR works as a repressor that controls transcription of the whole fad regulon, including fadA, fadB, fadD, fadE, fadI, and fadJ Binding of fadR is inhibited by fatty acyl-CoA compounds, which de-represses expression of the genes in the fad regulon. Regulatory proteins that control expression of β-oxidation genes in cells of other organisms are known in the art. The genes encoding these proteins can be similarly functionally deleted to enhance entry of carbon substrates through the initial steps of the β-oxidation pathway for synthesis of methyl ketones. In some versions of the invention, the regulatory protein that is functionally deleted is FadR or a homolog thereof. In some versions of the invention, the regulatory protein that is functionally deleted has a sequence comprising SEQ ID NO:32 or a sequence homologous thereto.

In some versions of the invention, an acyl-CoA dehydrogenase is functionally deleted. The functionally deleted acyl-CoA dehydrogenase can include any acyl-CoA dehydrogenase described herein or any homolog thereof. In some versions, the functionally deleted acyl-CoA dehydrogenase is encoded by a fadE gene or a homolog thereof. In some versions, the functionally deleted acyl-CoA dehydrogenase is a FadE protein or a homolog thereof. In some versions, the functionally deleted acyl-CoA dehydrogenase has a sequence comprising SEQ ID NO:28, a sequence comprising SEQ ID NO:30, a sequence homologous to any one or more of the foregoing, or any combination thereof.

Various combinations of recombinant genes and functional deletions for producing methyl ketones are described elsewhere herein.

Methyl ketones can be produced with the cells described herein by culturing the cells in the presence of a carbon source. The carbon source can include a carbohydrate or non-lipid based carbon source, such as a fermentable sugar, a short-chain organic acid, an amino acid, or other organic molecules. Examples of suitable fermentable sugars include adonitol, arabinose, arabitol, ascorbic acid, chitin, cellobiose, dulcitol, erythrulose, fructose, fucose, galactose, glucose, gluconate, inositol, lactose, lactulose, lyxose, maltitol, maltose, maltotriose, mannitol, mannose, melezitose, melibiose, palatinose, pentaerythritol, raffinose, rhamnose, ribose, sorbitol, sorbose, starch, sucrose, trehalose, xylitol, xylose, and hydrates thereof. Examples of short-chain organic acids include acetate, propionate, lactate, pyruvate, levulinate, and succinate. Examples of amino acids include histidine, alanine, isoleucine, arginine, leucine, asparagine, lysine, aspartic acid, methionine, cysteine, phenylalanine, glutamic acid, threonine, glutamine, tryptophan, glycine, valine, ornithine, proline, serine, and tyrosine. The carbon source can also include a lipid carbon source. Lipid carbon sources include fatty acids among other lipids.

After or during the culturing, the produced methyl ketones may be isolated from the recombinant cell. As used herein, "isolated from the recombinant cell" refers to isolating the methyl ketones from any portion or component of the recombinant cell, whether the cell is intact (whole) or non-intact (e.g., lysed). In various versions, the isolated methyl ketones may be present in a composition comprising the methyl ketones in an amount of at least about 1% w/w, at least about 5% w/w, at least about 10% w/w, at least about 15% w/w, at least about 20% w/w, at least about 25% w/w, at least about 30% w/w, at least about 35% w/w, at least about 40% w/w, at least about 45% w/w, at least about 50% w/w, at least about 55% w/w, at least about 60% w/w, at least about 65% w/w, at least about 70% w/w, at least about 75% w/w, at least about 80% w/w, at least about 85% w/w, at least about 90% w/w, at least about 95% w/w, or at least about 99% w/w. Various method of isolating methyl ketones are known in the art.

The cells of the invention may be genetically altered to functionally delete, express, or overexpress homologs of any of the specific genes or gene products explicitly described herein. Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Nucleic acid or gene product (amino acid) sequences of any known gene, including the genes or gene products described herein, can be determined by searching any sequence databases known the art using the gene name or accession number as a search term. Common sequence databases include GenBank (www.ncbi.nlm.nih.gov/genbank/), ExPASy (expasy.org), KEGG (www.genome.jp/kegg/), among others. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or gene products described herein include genes or gene products having at least about 30%, 35%, 40%, 45%, 50%, 55%, 60%, 65%, 70%, 75%, 80%, 85%, 90%, 95%, or 99% identity to the genes or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes in different species that evolved from a common ancestral gene by speciation. Normally, orthologs retain the same or similar function in the course of evolution. As used herein "orthologs" are included in the term "homologs".

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to acsA or other genes or products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical" in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Terms used herein pertaining to genetic manipulation are defined as follows.

Accession numbers: The accession numbers throughout this description are derived from the NCBI database (National Center for Biotechnology Information, i.e., "GenBank"), maintained by the National Institute of Health, USA, or the KEGG (Kyoto Encyclopedia of Genes and Genomics) database, maintained by the Kyoto Encyclopedia of Genes and Genomics and sponsored in part by the University of Tokyo.

Deletion: The removal of one or more nucleotides from a nucleic acid molecule or one or more amino acids from a protein, the regions on either side being joined together.

Derived: When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

Endogenous: An endogenous nucleic acid, gene, gene element (e.g., promoter, enhancer, coding sequence), polypeptide, sequence or any other element in a given cell is one that is naturally occurring in the given cell.

Exogenous: An exogenous nucleic acid, gene, gene element (e.g., promoter, enhancer, coding sequence), polypeptide, sequence or any other element in a given cell is one that is not naturally occurring in the given cell. The term "heterologous" is used herein interchangeably with "exogenous."

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Gene: "Gene" refers minimally to a coding sequence and a promoter operationally linked to the coding sequence. A gene may additionally include other elements, such as enhancers and silencers.

Introduce: When used with reference to genetic material, such as a nucleic acid, and a cell, "introduce" refers to the delivery of the genetic material to the cell in a manner such that the genetic material is capable of being expressed within the cell. Introduction of genetic material includes both transformation and transfection. Transformation encompasses techniques by which a nucleic acid molecule can be introduced into cells such as prokaryotic cells or non-animal eukaryotic cells. Transfection encompasses techniques by which a nucleic acid molecule can be introduced into cells such as animal cells. These techniques include but are not limited to introduction of a nucleic acid via conjugation, electroporation, lipofection, infection, and particle gun acceleration.

Isolated: An "isolated" biological component (such as a nucleic acid molecule, polypeptide, or cell) has been substantially separated or purified away from other biological components in its original form, such as its native form or the form in which it was originally produced.

Medium chain: When used with reference to medium chain fatty acids or medium chain methyl ketones refers to a carbon chain length of from 6 to 12 carbons. "Medium-chain methyl ketone" and "medium-chain length methyl ketone" are used interchangeably herein.

Nucleic acid: Encompasses both RNA and DNA molecules including, without limitation, cDNA, genomic DNA, and mRNA. Nucleic acids also include synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. An origin of replication is operably linked to a coding sequence if the origin of replication controls the replication or copy number of the nucleic acid in the cell. Operably linked nucleic acids may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated using the methods described herein.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using rtPCR and protein levels can be assessed using SDS page gel analysis.

Recombinant: A recombinant nucleic acid, gene, gene element (e.g., promoter, enhancer, coding sequence), or polypeptide is one that has a sequence that is not naturally occurring. A recombinant cell or microorganism is one that contains a recombinant nucleic acid, gene, gene element (e.g., promoter, enhancer, coding sequence), or polypeptide.

Vector or expression vector: An entity comprising a nucleic acid molecule that is capable of introducing the nucleic acid, or being introduced with the nucleic acid, into a cell for expression of the nucleic acid. A vector can include nucleic acid sequences that permit it to replicate in the cell, such as an origin of replication. A vector can also include one or more selectable marker genes and other genetic elements known in the art. Examples of suitable vectors are found below.

Unless explained otherwise, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below.

Exogenous nucleic acids encoding enzymes involved in a metabolic pathway for producing methyl ketones can be introduced stably or transiently into a cell using techniques well known in the art, including electroporation, calcium phosphate precipitation, DEAE-dextran mediated transfection, liposome-mediated transfection, conjugation, transduction, and the like. For stable transformation, a nucleic acid can further include a selectable marker. Suitable selectable markers include antibiotic resistance genes that confer, for example, resistance to neomycin, tetracycline, chloramphenicol, or kanamycin, genes that complement auxotrophic deficiencies, and the like. (See below for more detail.)

Various embodiments of the invention use an expression vector that includes a heterologous nucleic acid encoding a protein involved in a metabolic or biosynthetic pathway. Suitable expression vectors include, but are not limited to viral vectors, such as baculovirus vectors or those based on vaccinia virus, polio virus, adenovirus, adeno-associated virus, SV40, herpes simplex virus, and the like; phage vectors, such as bacteriophage vectors; plasmids; phagemids; cosmids; fosmids; bacterial artificial chromosomes; Pl-based artificial chromosomes; yeast plasmids; yeast artificial chromosomes; and any other vectors specific for cells of interest.

Useful vectors can include one or more selectable marker genes to provide a phenotypic trait for selection of transformed cells. The selectable marker gene encodes a protein necessary for the survival or growth of transformed cells grown in a selective culture medium. Cells not transformed with the vector containing the selectable marker gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In alternative embodiments, the selectable marker gene is one that encodes dihydrofolate reductase or confers neomycin resistance (for use in eukaryotic cell culture), or one that confers tetracycline or ampicillin resistance (for use in a prokaryotic cell, such as *E. coli*).

The coding sequence in the expression vector is operably linked to an appropriate expression control sequence (promoters, enhancers, and the like) to direct synthesis of the encoded gene product. Such promoters can be derived from microbial or viral sources, including CMV and SV40. Depending on the cell/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology*, 153:516-544).

Suitable promoters for use in prokaryotic cells include but are not limited to: promoters capable of recognizing the T4, T3, Sp6, and T7 polymerases; the $P_R$ and $P_L$ promoters of bacteriophage lambda; the trp, recA, heat shock, and lacZ promoters of *E. coli*; the alpha-amylase and the sigma-specific promoters of *B. subtilis*; the promoters of the bacteriophages of *Bacillus*; *Streptomyces* promoters; the int promoter of bacteriophage lambda; the bla promoter of the beta-lactamase gene of pBR322; and the CAT promoter of the chloramphenicol acetyl transferase gene. Prokaryotic promoters are reviewed by Glick, *J. Ind. Microbiol.* 1:277 (1987); Watson et al, Molecular Biology of the Gene, 4th Ed., Benjamin Cummins (1987); and Sambrook et al., In: *Molecular Cloning: A Laboratory Manual*, 3$^{rd}$ ed., Cold Spring Harbor Laboratory Press (2001).

Non-limiting examples of suitable promoters for use within a eukaryotic cell are typically viral in origin and include the promoter of the mouse metallothionein I gene (Hamer et al. (1982) *J. Mol. Appl. Gen.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); the yeast gal4 gene promoter (Johnston et al. (1982) *PNAS* (USA) 79:6971; Silver et al. (1984) *PNAS* (USA) 81:5951); and the IgG promoter (Orlandi et al. (1989) *PNAS* (USA) 86:3833).

Coding sequences can be operably linked to an inducible promoter. Inducible promoters are those wherein addition of an effector induces expression. Suitable effectors include proteins, metabolites, chemicals, or culture conditions capable of inducing expression. Suitable inducible promoters include but are not limited to the lac promoter (regulated by IPTG or analogs thereof), the lacUV5 promoter (regulated by IPTG or analogs thereof), the tac promoter (regulated by IPTG or analogs thereof), the trc promoter (regulated by IPTG or analogs thereof), the araBAD promoter (regulated by L-arabinose), the phoA promoter (regulated by phosphate starvation), the recA promoter (regulated by nalidixic acid), the proU promoter (regulated by osmolarity changes), the cst-1 promoter (regulated by glucose starvation), the tetA promoter (regulated by tetracycline), the cadA promoter (regulated by pH), the nar promoter (regulated by anaerobic conditions), the $p_L$ promoter (regulated by thermal shift), the cspA promoter (regulated by thermal shift), the T7 promoter (regulated by thermal shift), the T7-lac promoter (regulated by IPTG), the T3-lac promoter (regulated by IPTG), the T5-lac promoter (regulated by IPTG), the T4 gene 32 promoter (regulated by T4 infection), the nprM-lac promoter (regulated by IPTG), the VHb promoter (regulated by oxygen), the metallothionein promoter (regulated by heavy metals), the MMTV promoter (regulated by steroids such as dexamethasone) and variants thereof.

Alternatively, a coding sequence can be operably linked to a repressible promoter. Repressible promoters are those wherein addition of an effector represses expression. Examples of repressible promoters include but are not limited to the trp promoter (regulated by tryptophan); tetracycline-repressible promoters, such as those employed in the "TET-OFF"-brand system (Clontech, Mountain View, CA); and variants thereof.

In some versions, the cell is genetically modified with a heterologous nucleic acid encoding a gene product that is operably linked to a constitutive promoter. Suitable constitutive promoters are known in the art and include constitutive adenovirus major late promoter, a constitutive MPSV promoter, and a constitutive CMV promoter.

The relative strengths of the promoters described herein are well-known in the art.

In some versions, the cell is genetically modified with an exogenous nucleic acid encoding a single protein. In other embodiments, a modified cell is one that is genetically modified with exogenous nucleic acids encoding two or more proteins. Where the cell is genetically modified to express two or more proteins, those nucleic acids can each be contained in a single or in separate expression vectors. When the nucleic acids are contained in a single expression vector, the nucleotide sequences may be operably linked to a common control element (e.g., a promoter), that is, the common control element controls expression of all of the coding sequences in the single expression vector.

When the cell is genetically modified with heterologous nucleic acids encoding two or more proteins, one of the nucleic acids can be operably linked to an inducible promoter, and one or more of the nucleic acids can be operably linked to a constitutive promoter. Alternatively, all can be operably linked to inducible promoters or all can be operably linked to constitutive promoters.

Nucleic acids encoding enzymes desired to be expressed in a cell may be codon-optimized for that particular type of cell. Codon optimization can be performed for any nucleic acid by "OPTIMUMGENE"-brand gene design system by GenScript (Piscataway, NJ).

The introduction of a vector into a bacterial cell may be performed by protoplast transformation (Chang and Cohen (1979) *Molecular General Genetics*, 168:111-115), using competent cells (Young and Spizizen (1961) *Journal of Bacteriology*, 81:823-829; Dubnau and Davidoff-Abelson (1971) *Journal of Molecular Biology*, 56: 209-221), electroporation (Shigekawa and Dower (1988) *Biotechniques*, 6:742-751), or conjugation (Koehler and Thorne (1987) *Journal of Bacteriology*, 169:5771-5278). Commercially available vectors for expressing heterologous proteins in bacterial cells include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx, in addition to those described in the following Examples.

Methods for transforming yeast cells with heterologous DNA and producing heterologous polypeptides therefrom are disclosed by Clontech Laboratories, Inc., Palo Alto, Calif., USA (in the product protocol for the "YEAST-MAKER"-brand yeast transformation system kit); Reeves et al. (1992) *FEMS Microbiology Letters* 99:193-198; Manivasakam and Schiestl (1993) *Nucleic Acids Research* 21(18): 4414-5; and Ganeva et al. (1994) *FEMS Microbiology Letters* 121:159-64. Expression and transformation vectors for transformation into many yeast strains are available. For example, expression vectors have been developed for the following yeasts: *Candida albicans* (Kurtz, et al. (1986)

*Mol. Cell. Biol.* 6:142); *Candida maltosa* (Kunze et al. (1985) *J. Basic Microbiol.* 25:141); *Hansenula polymorpha* (Gleeson et al. (1986) *J. Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) *Bio/Technology* 8:135); *Pichia guilliermondii* (Kunze et al. (1985) *J. Basic Microbiol.* 25:141); *Pichia pastoris* (Cregg et al. (1985) *Mol. Cell. Biol.* 5:3376; U.S. Pat. Nos. 4,837, 148; and 4,929,555); *Saccharomyces cerevisiae* (Hinnen et al. (1978) Proc. Natl. Acad. Sci. USA 75:1929 and Ito et al. (1983) *J. Bacteriol.* 153:163); *Schizosaccharomyces pombe* (Beach et al. (1981) Nature 300:706); and *Yarrowia lipolytica* (Davidow et al. (1985) *Curr. Genet.* 10:380-471 and Gaillardin et al. (1985) *Curr. Genet.* 10:49).

Suitable procedures for transformation of *Aspergillus* cells are described in EP 238 023 and U.S. Pat. No. 5,679, 543. Suitable methods for transforming *Fusarium* species are described by Malardier et al., *Gene*, 1989, 78:147-56 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al. (1983) *Journal of Bacteriology*, 153: 163; and Hinnen et al. (1978) *PNAS* USA, 75:1920.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Background

Methyl ketones (MK) are naturally occurring compounds that have been shown to serve biological and industrial functions such as insecticides, pheromones, flavors, and fragrances, e.g. blue cheese flavor and fragrance comes from 2-heptanone and 2-nonanone produced by fungus in the maturation process (Collins et al., 2003). Similarly, 2-heptanone, 2-nonanone, 2-undecanone are found in plants, such as cinnamon, clove and coconut, where they contribute to the insecticide, flavor and fragrance profile (Forney and Markovetz, 1971; Kennedy, 2003; Zhu et al., 2018). Methyl ketones also have the potential to serve as renewable liquid transportation fuels. Medium-chain methyl-ketones, such as 2-nonanone and 2-undecanone, have high cetane numbers and low freezing points, making them compatible with diesel fuels (Table 1). In addition, these ketones and 2-heptanone can be condensed to yield long-chain, high cetane fuels (Frias et al., 2011; Harrison and Harvey, 2018).

TABLE 1

Properties of methyl ketone and its derivatives as potential diesel fuel applications.

| | Cetane Number[a] | Melting Temperature[b] (° C.) | Citations |
|---|---|---|---|
| 2-heptanone | 30.0 | −35.5 | (Yanowitz et al., 2017) |
| 2-nonanone | 46.1 | −15 | (Yanowitz et al., 2017) |
| 2-undecanone | 56.5 | 15 | (Goh et al., 2012) |
| 2-tridecanone | 60 | 30.5 | (Harrison and Harvey, 2018) |
| dioxolanes[c] | 81-91 | −11 | (Harrison and Harvey, 2018) |
| Palm oil derived biodiesel[d] | 61.9 | 13 | (Hoekman et al., 2012) |
| No. 2 petroleum diesel[e] | 45 | −18 | (Hoekman et al., 2012) |

[a]Literature reported cetane values that are either characterized experimentally or predicted by models; the minimum cetane number of diesel fuels in the U.S. is 40 according to ASTM standard D975.
[b]Melting temperatures are obtained from a chemical information collection, PubChem (pubchem.ncbi.nlm.nih.gov). In general, the freezing point trend is proportional to the melting temperature trend since both are measuring the required temperature of solid-liquid transition.
[c]The dioxolanes properties reported from the literature exemplified methyl ketones can be condensed to higher energy molecules.
[d]palm oil derived biodiesel is an example of commonly used biodiesel.
[e]No. 2 petroleum diesel is an example of commercial diesel fuels.

Methyl ketones are biologically produced from β-keto acids, unstable compounds that can spontaneously undergo decarboxylation under mild conditions (Kornberg et al., 1948). The medium chain β-keto acids, e.g. 3-oxooctanoate, are relatively less stable than shorter chain compounds, e.g. acetoacetate, possibly because the pentanyl moiety of 3-oxooctanoate is more favorable for attracting a proton to form a cyclic six-atom transition state of the decarboxylation process than methyl moiety of acetoacetate. This could explain why acetoacetate decarboxylase is an essential and rate-limiting step in acetone (Lan et al., 2013) or 2-butanone (Mehrer et al., 2019; Srirangan et al., 2016) biosynthesis while methyl ketone decarboxylase was shown to be unnecessary for 2-tridecanone biosynthesis (Goh et al., 2012).

β-keto acids are made via transthioesterification or hydrolysis reactions on β-ketoacyl thioester (-CoA, -ACP) substrates. For example, methyl ketone synthases act either as distinct enzymes ([Sh]Mks1/2) or as an embedded domain in modular type I polyketide synthases (PKS) by hydrolyzing β-ketoacyl-acyl carrier protein (ACP) substrates (Yu et al., 2010; Yuzawa et al., 2017). Similarly, β-ketoacyl-CoA thioesterases produce β-keto acids via hydrolysis. The long-chain β-keto acids spontaneously decarboxylate to yield methyl ketones (Goh et al., 2014; Nie et al., 2008). Alternatively, β-ketoacyl-CoA transferase (PcalJ) transfers the CoA moiety from short-chain substrates to succinate to form succinyl-CoA and the corresponding β-keto acid. The latter is enzymatically converted to a methyl ketone by acetoacetate decarboxylase (Adc) (Lan et al., 2013).

Over the last decade, several groups have applied metabolic engineering strategies to bacteria and yeast with the goal of increasing flux to desired methyl ketones. For instance, Zhu et al., built a chimeric *Saccharomyces cerevisiae* type I fatty acid synthase (FAS) by embedding a [Sh]Mks2 next to an ACP domain to increase the cleavage activities. An engineered strain that co-expressed [Sh]Mks1 and the FAS genes produced ~20 μg/g DCW $C_{11}$-$C_{15}$ methyl ketones (Zhu et al., 2017). Using *Escherichia coli* as a host, Goh et al., compared pathway efficiencies between the acyl-CoA methyl ketone synthase [Ec]FadM and the acyl-ACP methyl ketone synthase [Sh]MKS1 and [Sh]MKS2. The best strain (EGS895) overexpressed β-ketoacyl-CoA thioesterase ([Ec]FadM), acyl-CoA oxidase (Mlut_11700), acyl-ACP thioesterase ([Ec]TesA), and a bifunctional hydratase and dehydrogenase ([Ec]FadB). This strain produced significantly higher 2-tridecanone than that of the [Sh]MKS2 overexpression strain (Goh et al., 2012). In a follow-up study, the authors increased the $C_{11}$-$C_{15}$ methyl ketone titer up to 3.4 g/L in a fed-batch fermentation by overexpressing native FadR and FadD, deleting key acetate forming pathways, and consolidating the pathway from two plasmids into one (Goh et al., 2014). In addition, the authors further improved the methyl ketone titer up to 5.4 g/L by overexpression of NADH-dependent β-ketoacyl-ACP reductase FabG from *Acholeplasma laidlawii* to mitigate the NADPH imbalance caused by the endogenous FabG (Goh et al., 2018). Thus far, the FadM pathway is the most frequently used pathway for methyl ketone production due to its high activity. Recent efforts have focused on transferring methyl ketone pathways into non-model organisms such as oleaginous yeast, *Yarrowia lipolytica* (Hanko et al., 2018), soil bacteria, *Pseudomonas putida* (Dong et al., 2019) and chemolithoautotrophs, *Ralstonia eutropha* (Muller et al., 2013). Other studies designed metabolic pathways to make shorter chain-length methyl ketones. For instance, Lan et al., constructed an *E. coli* strain that overexpressed *Ralstonia eutropha* thiolase BktB and *Pseudomonas putida* 3-oxoadipate CoA-succinyl transferase PcalJ. The strain produced ~240 mg/L 2-pentanone from ~12 g/L glucose (Lan et al., 2013). Yuzawa et al., engineered a type I modular polyketide synthase (PKS) to produce short chain methyl ketones by inactivating the ketone reductase (KR) domain and switching to a malonyl-CoA preferred acyltransferase homologue domain. When the engineered PKS was overexpressed in *Streptomyces albus*, the culture generated ~140 mg/L 2-butanone and 2-pentanone (Yuzawa et al., 2018). Although various protein engineering strategies have been applied to control chain-length specificities for oleochemicals such as fatty acids (Yan and Pfleger, 2019), few studies have been reported for the production of 2-heptanone, 2-nonanone, or 2-undecanone (Park et al., 2012; Zhu et al., 2019).

Figure 1:
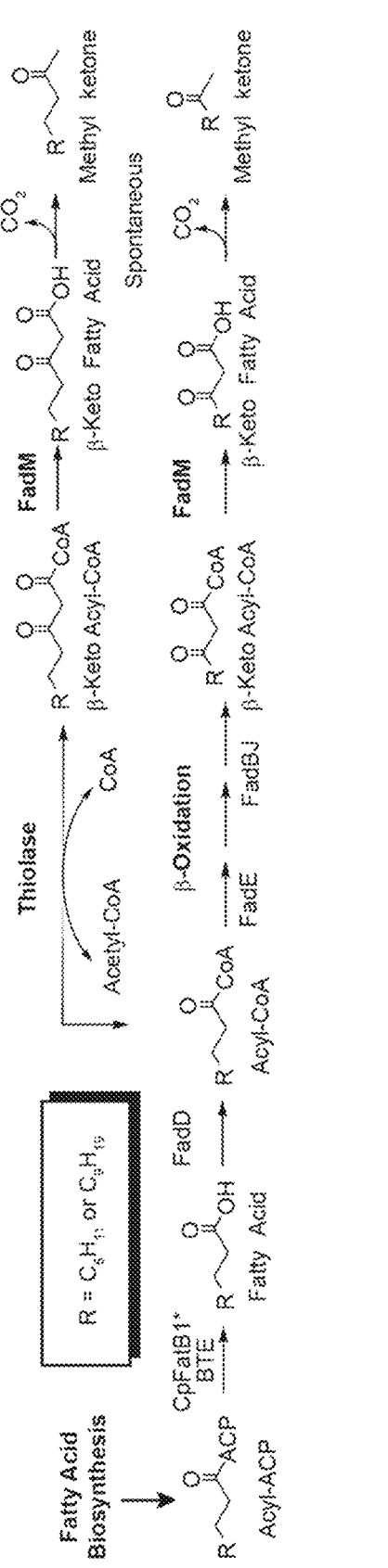
FIG. 1: Metabolic pathways designed for producing 2-heptanone, 2-nonanone and 2-undecanone in *E. coli*. Each pathway starts with a $C_8$- or $C_{12}$-specific thioesterases (CpFatB1* or BTE) which makes octanoate or dodecanoate from fatty acid biosynthesis. Free fatty acids are reactivated to octanoyl-CoA or dodecanoyl-CoA by fatty acid synthetases (<sup>Mt</sup>FadD6 or <sup>Ec</sup>FadD), respectively. Octanoyl-CoA or dodecanoyl-CoA undergoes an oxidation process by an acyl-CoA dehydrogenase (<sup>Ec</sup>FadE), and a bi-functional enoyl-CoA hydratase/3-hydroxyacyl-CoA dehydrogenase <sup>Ec</sup>FadBJ to generate β-keto-octanoyl-CoA or β-keto-dodecanoyl-CoA (pathways as marked in black). Alternatively, octanoyl-CoA and acetyl-CoA are condensed to generate β-ketodecanoyl-CoA by a thiolase <sup>Ec</sup>FadA. The β-ketoacyl-CoAs are converted to β-keto acids by a methyl ketone synthase <sup>Ec</sup>FadM, then spontaneously decarboxylated to methyl ketones.

In the present examples, we describe efforts to engineer *E. coli* to produce medium-chain length methyl ketones. Our work leverages highly-active and selective thioesterases that target 8- and 12-carbon substrates as well as two routes of converting fatty acids to the β-keto acid precursors of our target products. In prior work, we isolated a $C_8$-specific *Cuphea palustris* FatB1 thioesterase variant, annotated as CpFatB1.2-M4-287, hereafter CpFatB1*, that exhibited a 15-fold increase in $k_{cat}$ compared to the native variant while maintaining >90% selectivity towards producing octanoic acid (Hernández Lozada et al., 2018). An engineered *E. coli* strain that overexpressed the CpFatB1* from a single chromosomal copy produced 1.7 g/L octanoic acid from 20 g/L glycerol. In other studies, we leveraged the Cu-specific thioesterase from *Umbellularia californica* (BTE) to produce dodecanoic acid and other 12-carbon oleochemicals at ~g/L titers (Lennen et al., 2010; Agnew et al., 2012; Youngquist et al., 2013). Here, we used the selectivity of these thioesterases and permissive acyl-CoA synthetases to generate pools of acyl-CoAs with narrow chain-length distributions. We then compared a thiolase-mediated condensation and a β-oxidation pathway (FIG. 1) for generating β-ketoacyl-CoAs with similar chain-length distributions. In order to maximize conversion to methyl ketones, we compared fifteen homologs of the *E. coli* methyl ketone synthase FadM in search of variants with higher activities to medium chain substrates. Lastly, we used a condenser and dodecane overlay to capture volatilized methyl ketones from a bioreactor, thereby achieving the highest reported 2-heptanone titer in a fed-batch fermentation.

Materials and Methods

Bacterial Strains, Plasmids, Oligonucleotides, and Reagents

All bacterial strains used in the present examples are listed in Table 2. Phusion DNA Polymerase was purchased from New England Biolabs (Ipswich, MA). Plasmid extractions were performed with QIAGEN (Valencia, CA) miniprep reagents. DNA, including oligonucleotide primers and short gBlocks, was synthesized by Integrated DNA Technologies (IDT), Inc. (San Diego, CA). Fatty acids and methyl ketone standards used in the examples were purchased from Sigma-Aldrich (St. Louis, MO).

*E. coli* DH5α cells were used for cloning and assembling DNA molecules. Lysogeny broth (LB) was used to cultivate cells during the cloning and DNA assembly process. *E. coli* NHL17 (K12 MG1655 ΔaraBAD 4fadD::trcCpFatB1*), *E. coli* ΔRABIJ (MG1655 ΔaraBAD ΔfadR ΔfadA ΔfadB ΔfadI ΔfadJ) and *E. coli* TY34 (MG1655 ΔaraBAD ΔfadE:: $P_{trc}$-BTE ΔfadAB::$P_{trc}$-BTE ΔackApta::$P_{trc}$-BTEΦ($P_{trc}$-fadD)) were created as part of prior studies (Agnew et al., 2012; Hernández Lozada et al., 2018; Youngquist et al., 2013) and were used as base strains for production of 2-heptanone (NHL17), 2-nonanone (ΔRABIJ) and 2-undecanone (TY34). Pre-cultures were prepared in test tubes containing 5 mL LB and the appropriate antibiotics (final concentrations: carbenicillin, 100 µg/mL; chloramphenicol, 34 µg/mL; kanamycin 50 µg/mL).

Plasmid and Strain Construction

All plasmids used in the present examples are summarized in Table 2. Cloning of native *E. coli* genes into expression plasmids was performed by PCR amplification. Plasmids were constructed by annealing linearized DNAs using an isothermal assembly method (Gibson et al., 2009). Chromosomal expression cassettes were created using a combination of lambda red recombination and CRISPR/Cas9-mediated selection as described in prior work (Hernandez Lozada et al., 2018; Mehrer et al., 2018). All cloned sequences, integration cassettes, and gene deletions were confirmed by Sanger sequencing performed by Functional Biosciences (Madison, WI).

Sequences of FadM homologs were acquired from the Thyme database (www.enzyme.cbirc.iastate.edu/) (Cantu et al., 2011). Protein similarities were performed using the BLAST alignment tool from NCBI. Terminal signal peptide sequences were identified using SignalP 3.0 (www.cbs.dtu.dk/services/SignalP-3.0/) (Dyrløv Bendtsen et al., 2004) and were subsequently truncated when genes were designed for synthesis. Constructs expressing FadA and FadB homologs were obtained from a prior study (Mehrer et al., 2018). Genes encoding FadM homologs,

[Re]BktB and [Ml]ACO were codon-optimized and DNA sequences were chemically synthesized as gBlocks (IDT DNA).

Characterization of FadM Activity In Vivo

The relative activity of FadM homologs on various chain length substrates was measured by feeding free fatty acids to cultures of *E. coli* cells expressing a FadM homolog. These cultures were inoculated to starting $OD_{600}$ of 0.05 in 50 mL of LB supplemented with a defined amount of saturated fatty acid. All fatty acids were pre-dissolved in ethanol and supplemented to cultures at the following final concentrations: 1 g/L octanoic acid, 1 g/L decanoic acid, 200 mg/L dodecanoic acid, 100 mg/L tetradecanoic acid, or 100 mg/L hexadecenoic acid. Cultures were then grown at 37° C. with shaking at 250 rpm until an $OD_{600}$ of approximately 0.2 was reached. At this point, cultures were supplemented with a final concentration of 1 mM IPTG and cultivated at 30° C. with shaking at 250 rpm for an additional 24 h. After induction, samples were taken periodically to measure titers of fatty acids and methyl ketones.

Methyl Ketone Production in Shake Flasks

To demonstrate methyl ketone production in shake flasks, overnight cultures of *E. coli* strains (Table 2) were inoculated to a starting $OD_{600}$ of 0.05 in Clomburg medium (Clomburg et al., 2012) with 10% (v/v) dodecane and appropriate antibiotics and incubated at 37° C. with shaking at 250 rpm. Once the cultures reached an $OD_{600}$ of approximately 0.2, cultures were supplemented to a final concentration of 1 mM IPTG and incubated for an additional 24 hours at 30° C. with shaking at 250 rpm.

Extraction and Quantification of Methyl Ketones and Fatty Acids

Fatty acids and methyl ketones were extracted from culture according to an acid-based esterification method described previously (Grisewood et al., 2017; Hernandez Lozada et al., 2018). Individual species were separated using a Shimadzu GC equipped with an Agilent RTX-5 column (Santa Clara, CA) and quantified by FID. Quantification of fatty acids was normalized by inclusion of 50 µL of 12.5 mg/mL nonanoic acid, and/or 1.25 mg/mL pentadecanoic acid internal standards dissolved in ethanol. Octanoic acid, decanoic acid and dodecanoic acid were quantified based on the nonanoic acid internal standard, and tetradecanoic acid and hexadecenoic acid were quantified based on the pentadecanoic acid. Quantification of methyl ketones was normalized by inclusion of 50 µL of 62.5 mg/mL 2-octanone and/or 62.5 mg/mL 2-dodecanone dissolved in ethanol. 2-heptanone and 2-nonanone were quantified by 2-octanone, and 2-undecanone and longer chain methyl ketones were quantified by 2-dodecanone. In order to evaluate methyl ketone concentration in the distinct organic or aqueous phases, 50 mL cell cultures were centrifuged at 4500×g for 10 min and 0.5 mL samples from the dodecane layer and 2.5 mL samples aqueous phase were collected and evaluated separately.

To test for the rates of methyl ketone evaporation in our culturing apparatus, a final concentration of ~5.0 g/L 2-heptanone, 3.5 g/L 2-nonanone, and 6 g/L 2-undecanone was dissolved in 50 mL LB medium in 250 mL shake flasks. The concentration of each species was monitored for 48-hours during which the flasks were incubated at 30° C. with shaking at 250 rpm. In order to evaluate the effect of dodecane for reducing methyl ketone loss, 10-20% (v/v) dodecane was added to flasks and the 2-heptanone, 2-nonanone and 2-undecanone titers were measured every 12 hrs. MK standards (manufacturer) were run at the following concentrations to generate a peak area-based standard curve: 1000 mg/L, 500 mg/L, 250 mg/L, 100 mg/L, 50 mg/L, 25 mg/L.

Fed-Batch Bioreactor Fermentation

Fed-batch cultivation was performed using a 1-L Infors Multifors bioreactor. Overnight pre-cultures were inoculated to an initial $OD_{600}$ of 0.05 into a bioreactor containing 500 mL Clomburg medium with ~65 g/L glycerol. The bioreactor was operated at the following conditions: temperature was controlled at 30° C. at post-induction, air flow was 1.5 L/min, stirrer rate was varied between 250 rpm and 1000 rpm to control dissolved oxygen at a value of 40%, pH was maintained at 7.0 using 3 M phosphoric acid and pure ammonia hydroxide. When the $OD_{600}$ reached 0.2, IPTG was added to achieve a final concentration of 1 mM and 100 mL dodecane was fed in the bioreactor. At 24 h of post-induction, ~500 g/L glycerol was one-time bolus-fed into the bioreactor and fermentation terminated 96 h post-induction. Measurements of methyl ketone, fatty acid, glycerol, optical density, and $CO_2$ evolution were recorded for 96 hrs total.

The bioreactor outlet gas stream was directed through a heat exchange system to condense methyl ketone vapors stripped from the culture broth. The condenser was constructed with coiled quarter-inch outer diameter stainless steel tubing to ensure sufficient residence time in a water-ice bath. A water chiller supplied 6° C. to the outer shell of the condenser. The condensate was channeled to a bored-through union to facilitate the collection of the liquefied sample from the gaseous effluent.

Analysis of Glycerol Consumption

Glycerol was quantified on an HPLC (Shimadzu) equipped with an autosampler, quaternary pump, degasser and a refractive index detector. 1 mL fermentation broth samples were prepared by centrifuging at 15,000×g, and filtering the supernatant through a 0.22 μm membrane filter. For each sample, 10 μL was injected and separated for 25 min on a Restek Organic Acids column with a mobile phase of 5 mM $H_2SO_4$ at a flow rate of 0.6 mL/min. Glycerol standards (manufacturer) were run at the following concentrations to generate a peak area-based standard curve: 100 g/L, 50 g/L, 25 g/L, 10 g/L, 5 g/L, 1 g/L.

TABLE 2

Strains and plasmids used in the examples.

| Strain/Plasmid | Genotype | Source |
| --- | --- | --- |
| Strains | | |
| *E. coli* DH5a | F- Φ80lacZΔM15 Δ(lacZYA-argF) U169 recA1 endA1 hsdR17 (rk−, mk+) phoA supE44 λ− thi-1 gyrA96 relA1 | Invitrogen |
| NHL17 | K12 MG1655 ΔaraBAD ΔfadD::P$_{trc}$CpFatB1* | (Hernández et al., 2018) |
| ΔRAI | MG1655 ΔaraBAD ΔfadR ΔfadA ΔfadI | (Agnew et al., 2012) |
| ΔRBJ | MG1655 ΔaraBAD ΔfadR ΔfadB ΔfadJ | (Agnew et al., 2012) |
| ΔRABIJ | MG1655 ΔaraBAD ΔfadR ΔfadA ΔfadB ΔfadI ΔfadJ | (Agnew et al., 2012) |
| TRS12 | NHL17 strain ΔfadAEIR | Present examples |
| TY34 | MG1655 ΔaraBAD ΔfadE::P$_{trc}$-BTE ΔfadAB::trcBTE ΔackApta::Pt$_{rc}$-BTEΦ(P$_{trc}$-fadD) | (Youngquist et al., 2013) |
| Plasmids | | |
| pMP11 | pKD46 with constitutively expressed Cas9 and an aTc gRNA targeting the ColE1 origin | Present examples |
| pgRNA | Constitutively expressed sgRNA targeting a desired gene | Present examples |
| pBTRCK | Trc promoter, pBRR1 origin, Kan$^R$ | (Mehrer et al., 2018) |
| pBTRCK-CpFatB1* | Trc promoter, containing CpFatB1* an C$_8$– specific thioesterase mutant isolated in the lab | (Hernández et al., 2018) |
| pBTRCK-MlACO | Trc promoter, containing Mlut_11700 an Acyl-CoA oxidase from *Micrococcus luteus* | Present examples |
| pACYC | Trc promoter, pACYC origin, CmR | (Mehrer et al., 2018) |
| pACYC-MlACO | Trc promoter, containing Mlut_11700 an Acyl-CoA oxidase from *Micrococcus luteus* | Present examples |
| pACYC-AbFadA | Trc promoter, containing $^{Ab}$FadA a thiolase from *Alcanivorax borkumensis* | Present examples |
| pACYC-MaFadA | Trc promoter, containing $^{Ma}$FadA a thiolase from *Marinobacter aquaeolei* | Present examples |
| pACYC-SeFadA | Trc promoter, containing $^{Se}$FadA a thiolase from *Salmonella enterica* | Present examples |
| pACYC-ReBktB | Trc promoter, containing $^{Re}$BktB a thiolase from *Ralstonia eutropha* | Present examples |
| pACYC -PpFadA | Trc promoter, containing $^{Pp}$FadA a thiolase from *Pseudomona putida* | Present examples |
| pACYC -EcFadA | Trc promoter, containing $^{Ec}$FadA a thiolase from *E. coli* | Present examples |
| pACYC-VfFadA | Trc promoter, containing $^{Vf}$FadA a thiolase from *Vibrio fisheri* | Present examples |
| pACYC-AbFadB | Trc promoter, containing $^{Ab}$FadB a bi-functional 3-hydroxyacyl-CoA dehydrogenase from *Alcanivorax borkumensis* | Present examples |

TABLE 2-continued

Strains and plasmids used in the examples.

| Strain/Plasmid | Genotype | Source |
|---|---|---|
| pACYC-MaFadB | Trc promoter, containing $^{Ma}$FadB a bi-functional 3-hydroxyacyl-CoA dehydrogenase from *Marinobacter aquaeolei* | Present examples |
| pACYC-SeFadB | Trc promoter, containing $^{Se}$FadB a bi-functional 3-hydroxyacyl-CoA dehydrogenase from *Salmonella enterica* | Present examples |
| pACYC-PpFadB | Trc promoter, containing $^{Pp}$FadB a bi-functional 3-hydroxyacyl-CoA dehydrogenase from *Pseudomona putida* | Present examples |
| pACYC-EcFadB | Trc promoter, containing $^{Ec}$FadB a bi-functional 3-hydroxyacyl-CoA dehydrogenase from *E. coli* | Present examples |
| pACYC-VfFadB | Trc promoter, containing $^{Vf}$FadB a bi-functional 3-hydroxyacyl-CoA dehydrogenase from *Vibrio fisheri* | Present examples |
| pTRC99a | Trc promoter, pBR322 origin, AmpR | (Mehrer et al., 2018) |
| pTRC99a-FadD6-BaFadM | Trc promoter, fadD6 from *Mycobacterium tuberculosis* in front of FadM (GI: WP_034493719) from *Buttiauxella agrestis* | |
| pTRC99a-FadD6-BbFadM | Trc promoter, fadD6 in front of FadM (GI: KGQ11242) from *Beauveria bassiana* | |
| pTRC99a-FadD6-EclFadM | Trc promoter, fadD6 in front of FadM (GI: CZU17062) from *Enterobacter cloacae* | |
| pTRC99a-FadD6-CtFadM | Trc promoter, fadD6 in front of FadM (GI: WP_012815543) from *Cronobacter turicensis* | Present examples |
| pTRC99a-FadD6-EcFadM | Trc promoter, fadD6 in front of FadM (GI: WP_001194534) from *E. coli* | |
| pTRC99a-FadD6-Mt1FadM | Trc promoter, FadD6 in front of fadM1 (GI: WP_046024041) from *Mycobacterium tuberculosis* | Present examples |
| pTRC99a-FadD6-Mt2FadM | Trc promoter, FadD6 in front of FadM2 (GI: WP_063014014) from *M. tuberculosis* | Present examples |
| pTRC99a-FadD6-Mt3FadM | Trc promoter, FadD6 in front of FadM3 (GI: WP_066852574) from *M. tuberculosis* | Present examples |
| pTRC99a-FadD6-Mt4FadM | Trc promoter, FadD6 in front of FadM4 (GI: WP_076060981)from *M. tuberculosis* | Present examples |
| pTRC99a-FadD6-Mt5FadM | Trc promoter, FadD6 in front of FadM5 (GI: WP_090604673) from *M. tuberculosis* | Present examples |
| pTRC99a-FadD6-MuFadM | Trc promoter, FadD6 in front of FadM (GI: WP_036160439) from *Marinomonas ushuaiensis* | Present examples |
| pTRC99a-FadD6-NgFadM | Trc promoter, FadD6 in front of FadM (GI: WP_113852040) from *Neisseria gonorrhoeae* | Present examples |
| pTRC99a-FadD6-PaFadM | Trc promoter, FadD6 in front of FadM (GI: WP_141239354) from *Pseudomonas aeruginosa* | Present examples |
| pTRC99a-FadD6-PsFadM | Trc promoter, FadD6 in front of FadM (GI: WP008916720) from *Providencia sneebia* | Present examples |
| pTRC99a-FadD6-SeFadM | Trc promoter, FadD6 in front of FadM (GI: EBS6353971) from *Samonella enterica* | Present examples |
| pTRC99a-FadD6-SoFadM | Trc promoter, FadD6 in front of FadM (GI: WP_004954593) from *Serratia odorifera* | Present examples |

Results and Discussion

Bio Prospecting for Methyl Ketone Synthases

Figure 2A:
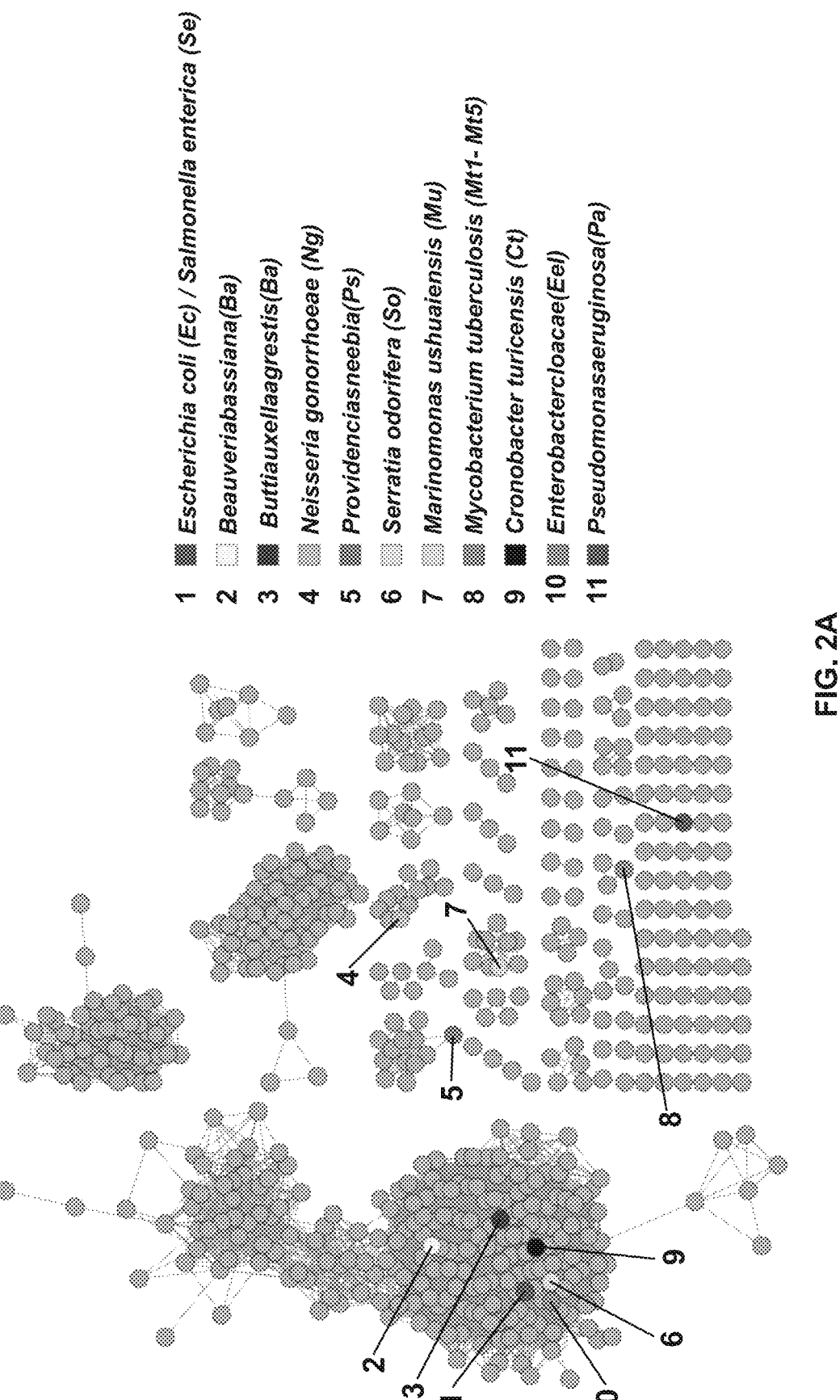
Figure 4A:
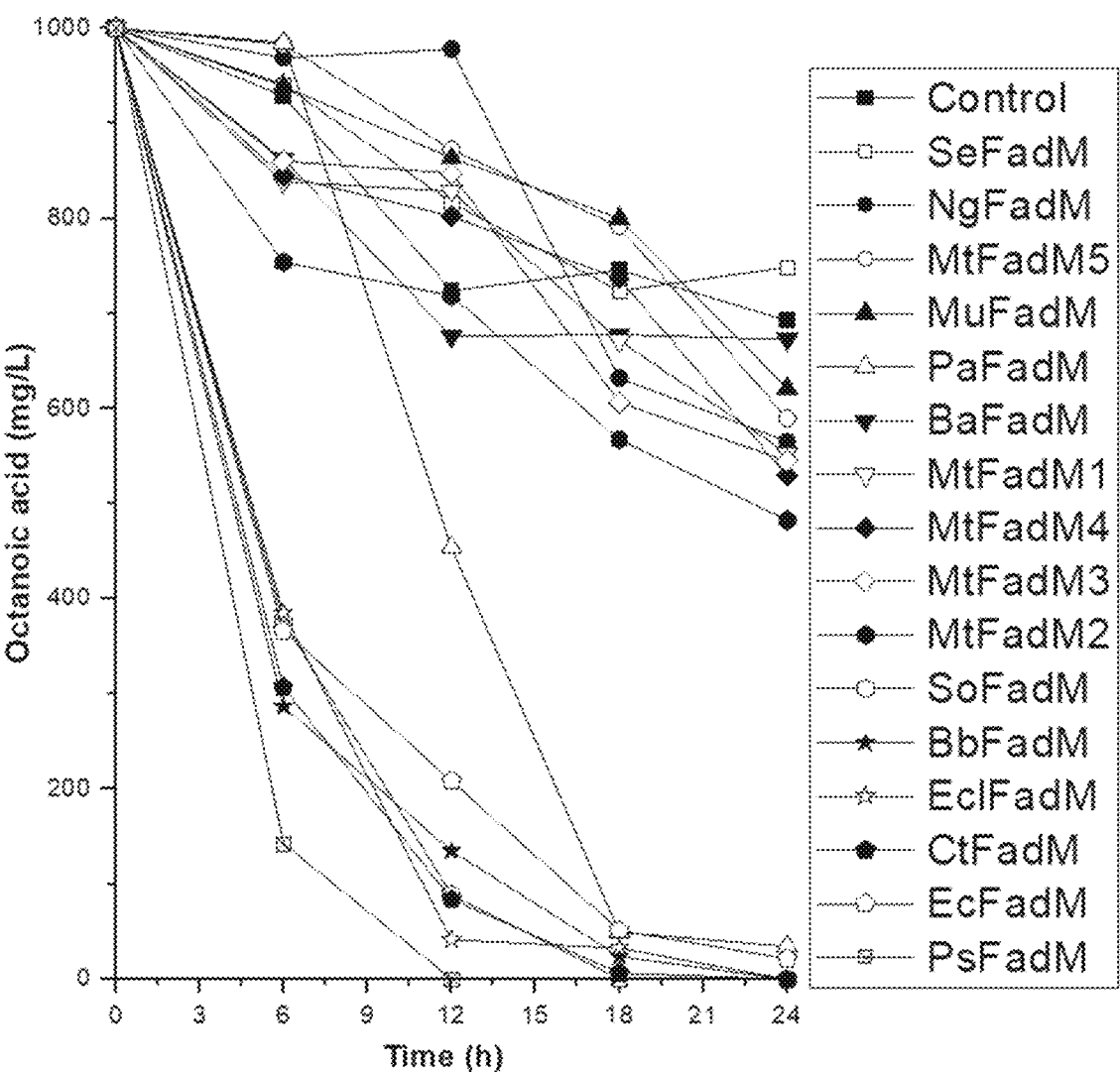
FIGS. 4A-4E: Timecourse of fatty acid consumption experiments used to calculate the consumption rates presented in FIG. 3. Cells were fed 1 g/L octanoic acid, 1 g/L decanoic acid 200 mg/L dodecanoic acid, 100 mg/L tetradecanoic acid, or 100 mg/L hexadecanoic acid. Each dot represented values calculated from three biological replicates. Fatty acid consumption rate (mg/L/h) was calculated by following equation.
Figure 4B:
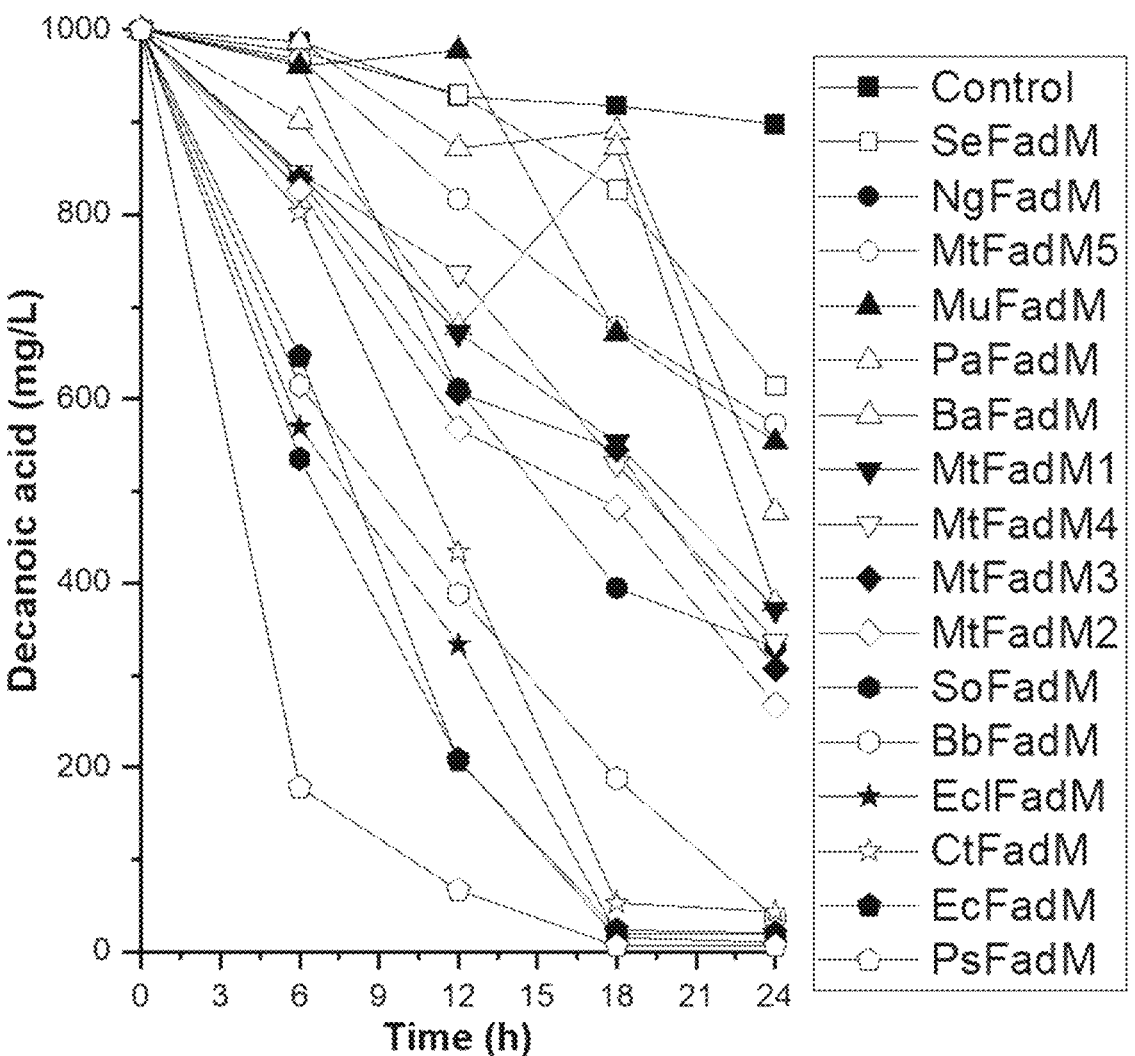
Figure 4C:
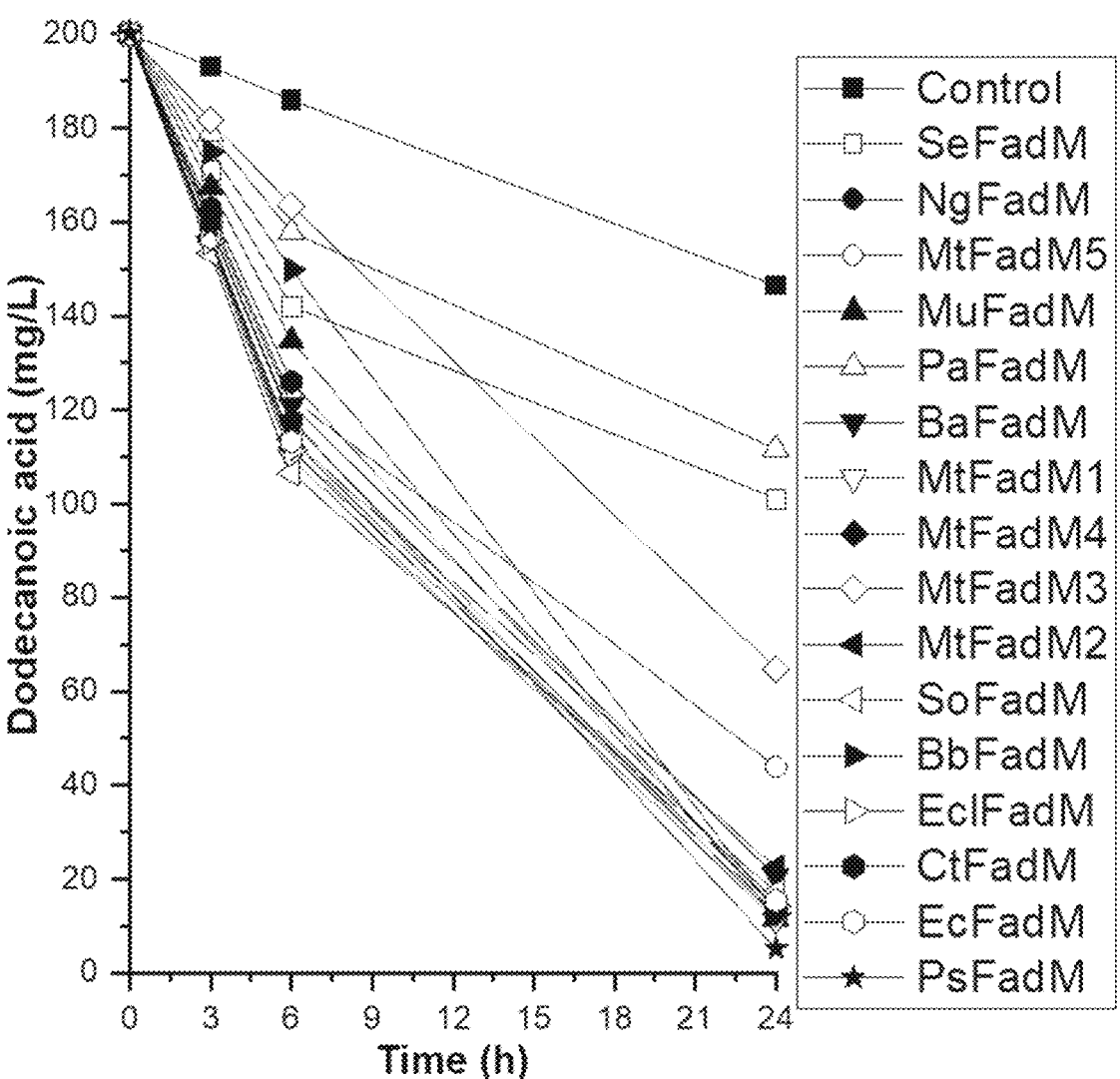
Figure 4D:
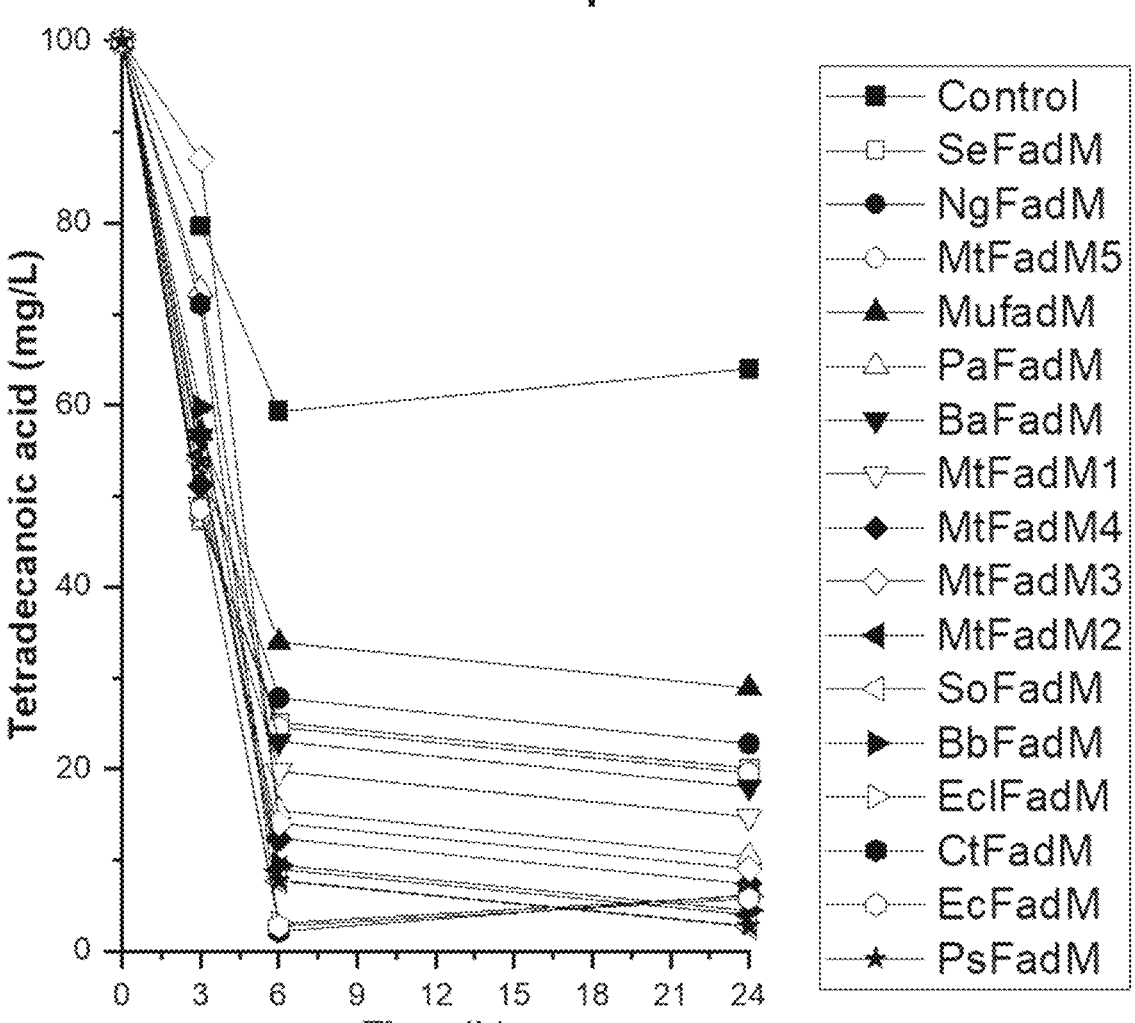
Figure 4E:
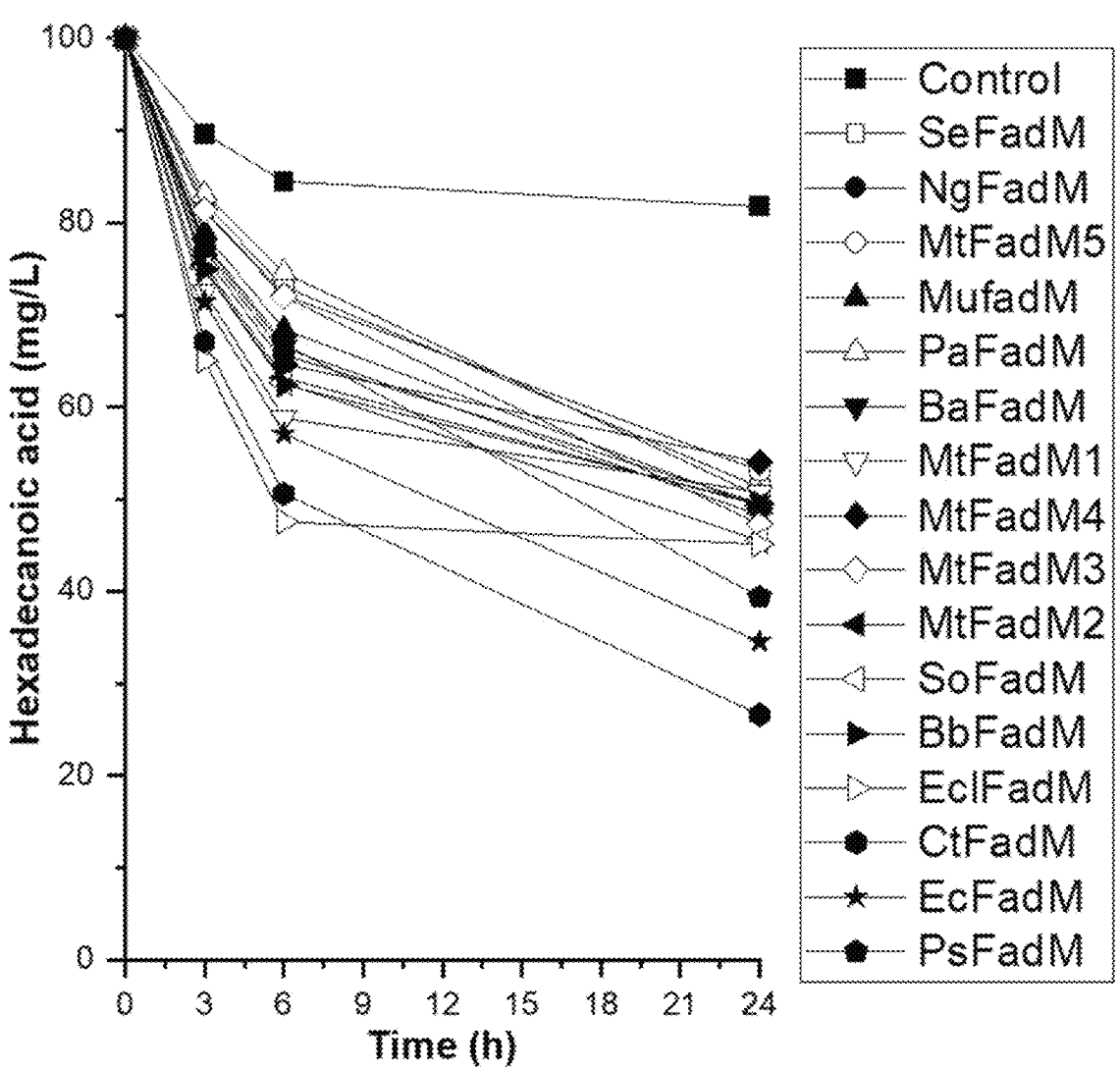

*E. coli* FadM had significantly lower activity on C8-C12 saturated acyl-CoAs than C14-C16 acyl-CoAs in in vitro kinetic studies using saturated, unsaturated, and hydroxylated acyl-CoA substrates, (Nie et al., 2008). In the present examples, we targeted production of medium-chain methyl-ketones and therefore started with a bioprospecting study to identify FadM homologs with high activity towards substrates (acyl-CoA or acyl-ACP) with twelve or less carbons. We conducted a homology search with the Basic Local Alignment Search Tool to identify candidate protein sequences. The search generated a wide range of biological diversity that we sorted using the Enzyme Similarity Tool. We selected fifteen FadM homologs which had a protein sequence similarity range of 30-95% based on a pairwise comparison of each thioesterase, shown in FIG. 2A. We were particularly interested in homologs from *Salmonella enterica* (SeFadM) and *Pseudomonas aeruginosa* (PaFadM)

because these species were known to have strong β-oxidation activities (Chakrabarty et al., 1973; Iram and Cronan, 2006) and have been sources of active enzymes used in prior studies (Mehrer et al., 2018). *Mycobacterium tuberculosis* possessed several type III thioesterases that have been previously shown activities towards acyl-CoAs (Wang et al., 2007) and five different homologs (Mt1-Mt5 FadM) were found that shares 26-58% similarities to the $^{Ec}$FadM (FIG. 2B).

The activity of the FadM homologs was assayed in vivo by feeding fatty acids of varied chain length to *E. coli* ΔfadAIR+pTRC99a-FadD6-"FadM", and monitoring fatty acid consumption and methyl ketone production (FIG. 3). $^{Mt}$TadD6 was overexpressed to increase the acyl-CoA synthetase activity required to activate the exogenous fatty acids fed to cells. $^{Mt}$FadD6 has been shown to act on medium-chain free fatty acids with greater activity than native FadD from *E. coli* (Youngquist et al., 2013, Herneandez-Lozada et al., Under Review). The 4fadR deletion was included to deregulate expression of FadE and FadB, which are responsible for the conversion of saturated acyl-CoA to the corresponding 3-ketoacyl-CoA. The ΔfadAI deletions were included to block the thiolase reaction that would otherwise lead to the shortening of the 3-ketoacyl-CoA. Given the metabolic engineering strategy used, any fatty acid consumption would be coupled to production of the corresponding methyl ketone. In FIG. 3, we report both the fatty acid consumption rate (timecourses available in FIGS. 4A-4E) and the measured titer of methyl ketones because many medium-chain methyl ketones are volatile and lost from the headspace of the flask. In general, the trend of fatty acid consumption rate between enzyme variants tracked with the trend of methyl ketone production (FIG. 3). We found that *Providencia* sneebia FadM showed the highest activities toward medium-chain substrates and produced ~50 mg/L 2-heptanone, ~43 mg/L 2-nonanone, and 50 mg/L 2-undecanone. In general, the *P. sneebia* FadM showed high activity against each chain length tested, within error of the best enzymes producing pentadecanone and heptadecanone (FIG. 3).

Metabolic Engineering to Improve 2-Heptanone Production

After identifying promising FadM variants, we next developed a strain to produce 2-heptanone utilizing the modified β-oxidation pathway outlined in FIG. 5A and a previously characterized acyl-ACP thioesterase with strong activity towards octanoyl-ACP. The base strain for this example was *E. coli* NHL17 (MG1655 ΔaraBAD ΔfadD::trc-CpFatB1*) which has been shown to produce up to 1.7 g/L of octanoic acid (Hernandez Lozada et al., 2018). To improve the flux towards 2-heptanone, fadA, fadI, and fadR were deleted from NHL17 to generate the strain TRS12. These deletions were included for the same reasons described above—blocking thiolase reactions and upregulating FadE and FadB. The FadM activity in TRS12 solely came from the chromosomal expression of the native $^{Ec}$FadM. This strain generated low titers, <1 mg/L, of 2-heptanone (data not shown). To improve production further, we overexpressed $^{Ec}$FadM from the high copy plasmid, pTRC99a-FadD6-EcFadM. This strain generated a titer of 2.4 mg/L of 2-heptanone (FIGS. 5A-5B). In order to increase the flux from acyl-CoA to enoyl-CoA we overexpressed $^{Ec}$FadE. This modification led to a ten-fold increase in 2-heptanone concentration, to a final titer of 21.9 mg/L (FIGS. 5A-5B). We next replaced $^{Ec}$FadM with $^{Ps}$FadM, the most active variant from our bioprospecting study, to make the expression plasmid, pTRC99a-FadD6-PsFadM. When co-expressed with $^{Ec}$FadE, the strain generated a final titer of 78.4 mg/L 2-heptanone (FIGS. 5A-5B). Lastly, $^{Ec}$FadE was replaced with the acyl-CoA oxidase from *M. luteus* (Goh et al. 2012), and was co-expressed from the pACYC-Mlut_11700 plasmid alongside pTRC99a-FadD6-PsFadM. Replacing the membrane protein $^{Ec}$FadE with the soluble heterologous acyl-CoA oxidase increased the 2-heptanone titer to 215.2 mg/L (FIGS. 5A-5B) with 97% selectivity. We suspect that this titer is underestimated, because when we incubated a defined 5 g/L 2-heptanone/water solution with 10% dodecane (v/v) in the same shake flasks, we observed that ~70% of the 2-heptanone was lost (FIG. 6A) after 24 hours.

Coupling Bioreactor with Condenser to Reduce 2-Heptanone Loss

To benchmark methyl ketone production, we conducted fed-batch cultivations by periodically feeding glycerol boluses to cells grown in a stirred bioreactor. We applied two strategies to reduce the loss of 2-heptanone in the off-gas: adding 20% dodecane to the culture (FIG. 6A) and coupling a condenser to the bioreactor to harvest vaporized 2-heptanone (FIG. 7). After 72 h of induced cultivation, cells consumed 111.5 g/L of glycerol, reached a biomass density of $OD_{600}$ ~40, and produced 3.34 g/L methyl ketone titer (FIG. 8A). When a condenser was added to the off-gas line, we observed a similar trend of glycerol consumption, biomass formation and methyl ketone production with modestly increased titers. After 72 h of induced cultivation, cells consumed 126 g/L glycerol, reached a biomass density of $OD_{600}$ ~50, produced 4.4 g/L methyl ketone at the maximum titer (FIG. 8B). At longer times, the titer of methyl ketones decreased, likely due to the rate of evaporation exceeding the rate of generation, which one would expect to be low as the carbon source, glycerol, is exhausted. After 96 hours, we observed a small amount (~25 mL of 2.3 g/L) of a MK containing solution in the condensed phase, representing ~5% of total MK titer (FIG. 8C). We suspect that we may either be failing to provide sufficient cooling duty or we may be stripping MK from the condensed phase with our current design (FIG. 7). The volatility and ability of MK to be stripped from culture may be advantageous when scaling up the process.

Metabolic Engineering to Improve 2-Nonanone Production

Our initial experiments suggested that the oxidation of saturated acyl-CoAs was a limiting factor in converting free fatty acids to methyl-ketones (i.e. acyl-CoA oxidase improved production). Therefore, we considered an alternative pathway in which oxidation was replaced by thiolase-mediated extension of the saturated acyl-CoA to a β-ketoacyl-CoA with two extra carbons. This idea is modeled off of the reverse β-oxidation pathway that has been shown to produce long chain acyl-CoAs in *E. coli* fermentations (Dellomonaco et al., 2011; Mehrer et al., 2018). The thiolase route avoids the need to generate NADH when cells are actively metabolizing glycerol and already have a highly reduced ratio of NADH/NAD+. To test this approach, we cloned a family of seven thiolase enzymes into a pACYC vector and coexpressed each with pTRC99a-FadD6-PsfadM in *E. coli* 4fadABIJR. The activity of the $^{Ec}$FadA homologs was assayed in vivo by feeding 0.5 g/L octanoic acid to *E. coli* ΔfadABIJR+pTRC99a-FadD6-PsFadM+pACYC-"FadA", and monitoring octanoic acid consumption and 2-nonanone production (FIG. 9A). In general, all seven thiolase enzymes conferred the ability to consume octanoic acid and produce 2-nonanone (FIGS. 9B and 10A). In terms of ranking, we found strains expressing $^{Re}$BktB and $^{Se}$FadA exhibited the highest consumption rates (over 80% octanoic acid consumed within 18 h) and 2-nonanone titers (~280 mg/L) (FIGS. 9B and 10B).

Next, we evaluated 2-nonanone production from glycerol in the background strain ΔfadAIR pTRC99a-FadD6-PsFadM+pACYC-ReBktB+pBTRCK-CpFatB1*. After 24 h in a batch shake flask culture, strains produced ~1.15 g/L 2-nonanone representing 75% of total methyl ketones from the 45 g/L glycerol fed (FIGS. 9C and 9D). We also suspect that the titer is underestimated, because when we incubated a defined 3.3 g/L 2-nonanone/water solution in the same shake flasks, we observed that 90% of the 2-nonanone was lost within 24 h (FIG. 6A).

To benchmark 2-nonanone production, we conducted fed-batch cultivations by bolus feeding glycerol to cells grown in a stirred bioreactor. In order to reduce the loss of 2-nonanone in the off-gas, we applied the two strategies: adding 20% dodecane to the culture and coupling a condenser to the bioreactor to harvest vaporized 2-nonanone (FIG. 7). After 72 h post-induction, cells consumed 107.1 g/L of glycerol, reached a biomass density of $OD_{600}$ ~52, and produced a 3.0 g/L methyl ketone titer (FIG. 9E). When a condenser was applied to the off-gas line, we observed a similar trend of glycerol consumption, biomass formation and methyl ketone production (data not shown). After 96 h post-induction, we found ~23 mL liquid containing ~120 mg/L methyl ketones collected in the condenser, representing less than 1% total MK. Overall, our results showed the thiolase-mediated condensation route is capable of producing 2-nonanone. Further optimization can be employed to avoid the loss of octanoic acid intermediates from the cell (FIG. 10C).

Metabolic Engineering to Improve 2-Undecanone Production

The *Umbellularia californica* acyl-ACP thioesterase BTE has high activity towards C12 acyl-ACPs. BTE has been used in metabolic pathways to produce dodecanoate, 1-dodecanol, and polyhydroxydodecanoate, etc (Agnew et al., 2012; Lennen et al., 2010; Youngquist et al., 2013). Therefore, we used BTE to generate dodecanoate as an intermediate to enzymatically produce 2-undecanone. To test this approach, we chose a base strain TY34 (ΔfadE::trcBTE ΔfadAB::trcBTE ΔackApta::trcBTEΦ(PTrc-fadD) from Youngquist et al., 2013, in which 1-dodecanol was produced in titers over 1 g/L. To this strain, we introduced Mlut_11700, $^{Ps}$FadM, and increased expression of $^{Ec}$FadD. Mlut_11700 was selected for its higher activity in catalyzing the dehydrogenation of acyl-CoA to 2-enoyl-CoA. $^{Ps}$FadM was selected from the 15 homologs tested in FIG. 3 for its strong activity towards twelve carbon substrates. We selected $^{Ec}$FadD instead of $^{Mt}$FadD6 because $^{Ec}$FadD was previously shown higher activities converting dodecanoate to dodecanoyl-CoA (Youngquist et al., 2013). We chose to overexpress a FadB homolog because the endogenous $^{Ec}$fadAB operon in TY34 strain was replaced by one copy of BTE.

In prior work, we observed that the source of the FadAB complex affected the product profile from reverse β-oxidation cycles activities (Mehrer et al., 2018), indicating that there may be chain length preferences. We chose six FadB homologs from which have previously shown functional FadAB complexes when testing reversed β-oxidation pathways (Mehrer et al., 2018). We evaluated each by comparing 2-undecanone titers in TY34 strains harboring three plasmids: pACYC-"FadB", pBTRCK-Mlu_11700, and pTRC99a-PsFadM (FIG. 11A). While control strains harboring a pACYC empty vector could not produce 2-undecanone, strains expressing each FadB homolog showed substantial quantities of 2-undecanone (FIG. 11B). The strain harboring FadB from *Pseudomonas putida* generated the highest titer (350 mg/L) of methyl ketones and the highest specificity (58%) towards 2-undecanone. This result is not surprising considering *P. putida* naturally accumulates medium-chain length polyhydroxyalkanoate (PHA) and likely maintains a relatively higher $C_8$-$C_{12}$ activity to provide sufficient 3-hydroxylacyl-CoA pools, the most common substrates for PHA synthases PhaC1/C2 (Hoffmann and Rehm, 2004, 2005).

Next, we evaluated 2-undecanone synthesis in a time course experiment by growing strains in a shake flask in batch mode. We monitored cell growth, glycerol consumption, methyl ketone production, and fatty acid intermediates. As can be seen in FIGS. 11C and 11D, 25 g/L glycerol was depleted after 36 h. Cell growth reached a plateau after ~12 h, and the highest 2-undecanone concentration 335 mg/L was observed at ~48 h. The 2-undecanone titer represented ~62% of the total amount of methyl ketones. Overall, these data showed that we have successfully designed and optimized strains and metabolic enzymes to improve 2-undecanone production. Interestingly, the titers of 2-undecanone were significantly lower than those observed for 2-heptanone and 2-nonanone. This may be due to the difference in activity between the CpFatB1* and BTE thioesterases; residual levels of dodecanoic acid and tetradecanoic acid were substantially lower than residual octanoic acid (FIG. 12).

CONCLUSION

In these examples, we demonstrated metabolic engineering strategies for selective synthesis of 2-heptanone, 2-nonanone and 2-undecanone in *E. coli*. Through bioprospecting, we identified a FadM variant from *Providencia sneebia* that demonstrated higher activity on medium-chain substrates. When co-expressed with selective thioesterases it was capable of producing three different chain length MK products. In each case, the MK product profile was consistent with the selectivity of the thioesterase used. We demonstrated a novel thiolase-condensation route for converting acyl-CoAs to β-ketoacyl-CoA, the FadM substrate. When co-expressed with the CpFatB1*, a strain produced 2-nonanone with a titer up to 3.0 g/L; the highest reported titer to date (Table 3). Interestingly, this strain also excreted substantial amounts of octanoic acid, indicating that further optimization could further improve titers. In each of our studies, we observed substantial product loss due to evaporation and stripping. We coupled a rudimentary, water-cooling condenser to a bioreactor and found that it helped to increase titers over the timecourse. While the evaporative loss is a challenge that leads to underestimation of product titers, it may be an advantage when scaling up MK production.

TABLE 3

| Summary of reported titer, yield and rate of methyl ketone production by microorganisms. | | | | | | |
|---|---|---|---|---|---|---|
| Product | Titers (g/L) | Yield (g/g) | Rate (g/L/h) | Cultivation Strategies | Species | References |
| 2-heptanone | 4.4 | 0.035 g/g consumed glycerol | 0.061 | bioreactor, fed-batch | *E. coli* | Present examples |
| 2-nonanone | 3.0 | 0.028 g/g consumed glycerol | 0.042 | bioreactor, fed-batch | *E. coli* | Present examples |
| 2-undecanone | 0.34 | 0.014 g/g consumed glycerol | 0.007 | shake flask, batch | *E. coli* | Present examples |
| $C_{11}$-$C_{15}$ MK | 5.4 | ~0.05 g/g consumed glucose | 0.05 | bioreactor, fed-batch | *E. coli* | Goh et al., 2018 |
| 2-pentanone | 0.24 | 0.024 g/g consumed glucose | 0.0033 | shake flask, batch | *E. coli* | Lan et al., 2013 |
| $C_{13}$-$C_{23}$ MK | 0.31 | 0.0074 g/g fed glucose | 0.00155 | bioreactor, fed-batch | *Y. lipolytica* | Hanko et al., 2018 |
| $C_{11}$-$C_{15}$ MK | 10$^a$ | NR | NR | shake flask, batch | *S. cerevisiae* | Zhu et al., 2017 |
| 2-butanone 2-heptanone | 0.24 | 0.0028 g/g fed hydrolysate | 0.0011 | bioreactor, batch | *S. albus* | Yuzawa et al., 2018 |

TABLE 3-continued

Summary of reported titer, yield and rate of methyl ketone production by microorganisms.

| Product | Titers (g/L) | Yield (g/g) | Rate (g/L/h) | Cultivation Strategies | Species | References |
|---|---|---|---|---|---|---|
| $C_{13}$-$C_{15}$ MK | 1.1 | 0.169 g/g fed glucose | 0.023 | shake flask, batch | *P. putida* | Dong et al., 2019 |
| $C_{13}$-$C_{15}$ MK | 0.18 | NR | 0.0015 | bioreactor, batch | *R. eutropha* | Muller et al., 2013 |

NR = Not reported

[a]µg/DCW

[b]Yield is calculated as either g/g fed carbon source or g/g consumed carbon source, where former is quantified by dividing the reported titer (g/L) over the initial carbon concentration and the latter is directly reported in the original papers.

REFERENCES

Agnew, D. E., Stevermer, A. K., Youngquist, J. T., Pfleger, B. F., 2012. Engineering *Escherichia coli* for production of C12-C14 polyhydroxyalkanoate from glucose. *Metab. Eng.* 14, 705-713.

Cantu, D. C., Chen, Y., Lemons, M. L., Reilly, P. J., 2011. ThYme: a database for thioester-active enzymes. Nucleic Acids Res. 39, D342-D346.

Chakrabarty, A. M., Chou, G., Gunsalus, I. C., 1973. Genetic Regulation of Octane Dissimilation Plasmid in *Pseudomonas*. Proc. Natl. Acad. Sci. 70, 1137-1140.

Collins, Y. F., McSweeney, P. L. H., Wilkinson, M. G., 2003. Lipolysis and free fatty acid catabolism in cheese: a review of current knowledge. Int. Dairy J. 13, 841-866.

Clomburg, J. M., Vick, J. E., Blankschien, M. D., Rodri-guez-Moyá, M., Gonzalez, R., 2012. A Synthetic Biology Approach to Engineer a Functional Reversal of the β-Oxidation Cycle. ACS Synth. Biol. 1, 541-554.

Dellomonaco, C., Clomburg, J. M., Miller, E. N., Gonzalez, R., 2011. Engineered reversal of the β-oxidation cycle for the synthesis of fuels and chemicals. Nature 476, 355-359.

Dong, J., Chen, Y., Benites, V. T., Baidoo, E. E. K., Petzold, C. J., Beller, H. R., Eudes, A., Scheller, H. V., Adams, P. D., Mukhopadhyay, A., Simmons, B. A., Singer, S. W., 2019. Methyl ketone production by *Pseudomonas putida* is enhanced by plant-derived amino acids. *Biotechnol. Bioeng.* 116, 1909-1922.

Dyrløv Bendtsen, J., Nielsen, H., von Heijne, G., Brunak, S., 2004. Improved Prediction of Signal Peptides: SignalP 3.0. J. Mol. Biol. 340, 783-795.

Forney, F., Markovetz, A., 1971. The biology of methyl ketones. J. Lipid Res. 12, 383-395.

Frias, J. A., Richman, J. E., Erickson, J. S., Wackett, L. P., 2011. Purification and Characterization of OleA from *Xanthomonas campestris* and Demonstration of a Non-decarboxylative Claisen Condensation Reaction. J. Biol. Chem. 286, 10930-10938.

Harrison, K. W., Harvey, B. G., 2018. High cetane renew-able diesel fuels prepared from bio-based methyl ketones and diols. Sustain. Energy Fuels 2, 367-371.

Hernández Lozada, N. J., Lai, R.-Y., Simmons, T. R., Thomas, K. A., Chowdhury, R., Maranas, C. D., Pfleger, B. F., 2018. Highly Active C 8-Acyl-ACP Thioesterase Variant Isolated by a Synthetic Selection Strategy. ACS Synth. Biol. 7, 2205-2215.

Hoekman, S. K., Broch, A., Robbins, C., Ceniceros, E., Natarajan, M., 2012. Review of biodiesel composition, properties, and specifications. Renew. Sustain. Energy Rev. 16, 143-169.

Gibson, D. G., Young, L., Chuang, R.-Y., Venter, J. C., Hutchison, C. A., Smith, H. O., 2009. Enzymatic assem-bly of DNA molecules up to several hundred kilobases. Nat. Methods 6, 343-345.

Goh, E.-B., Baidoo, E. E. K., Keasling, J. D., Beller, H. R., 2012. Engineering of Bacterial Methyl Ketone Synthesis for Biofuels. *Appl. Environ. Microbiol.* 78, 70-80.

Goh, E.-B., Baidoo, E. E. K., Burd, H., Lee, T. S., Keasling, J. D., Beller, H. R., 2014. Substantial improvements in methyl ketone production in *E. coli* and insights on the pathway from in vitro studies. *Metab. Eng.* 26, 67-76.

Goh, E.-B., Chen, Y., Petzold, C. J., Keasling, J. D., Beller, H. R., 2018. Improving methyl ketone production in *Escherichia coli* by heterologous expression of NADH-dependent FabG. *Biotechnol. Bioeng.* 115, 1161-1172.

Grisewood, M. J., Hernandez-Lozada, N. J., Thoden, J. B., Gifford, N. P., Mendez-Perez, D., Schoenberger, H. A., Allan, M. F., Floy, M. E., Lai, R.-Y., Holden, H. M., Pfleger, B. F., Maranas, C. D., 2017. Computational Redesign of Acyl-ACP Thioesterase with Improved Selectivity toward Medium-Chain-Length Fatty Acids. ACS Catal. 7, 3837-3849.

Hanko, E. K. R., Denby, C. M., Sanchez i Nogué, V., Lin, W., Ramirez, K. J., Singer, C. A., Beckham, G. T., Keasling, J. D., 2018. Engineering β-oxidation in *Yarrowia hpolytica* for methyl ketone production. Metab. Eng. 48, 52-62.

Harrison, K. W., Harvey, B. G., 2018. High cetane renew-able diesel fuels prepared from bio-based methyl ketones and diols. Sustain. Energy Fuels 2, 367-371.

Hernańdez Lozada, N. J., Lai, R.-Y., Simmons, T. R., Thomas, K. A., Chowdhury, R., Maranas, C. D., Pfleger, B. F., 2018. Highly Active C 8-Acyl-ACP Thioesterase Variant Isolated by a Synthetic Selection Strategy. ACS Synth. Biol. 7, 2205-2215.

Hernandez Lozada, N. J., Simmons, T. R., Xu, K., Jindra, M. A., Pfleger, B. F., 2020. Production of 1-octanol in *Escherichia coli* by a high flux thioesterase route. doi: Under review. Hoffmann, N., Rehm, B. H., 2004. Regu-lation of polyhydroxyalkanoate biosynthesis in *Pseudomonas putida* and *Pseudomonas aeruginosa*. FEMS Microbiol. Lett. 237, 1-7.

Hoffmann, N., Rehm, B. H. A., 2005. Nitrogen-dependent regulation of medium-chain length polyhydroxyalkanoate biosynthesis genes in pseudomonads. Biotechnol. Lett. 27, 279-282.

Iram, S. H., Cronan, J. E., 2006. The β-Oxidation Systems of *Escherichia coli* and *Salmonella enterica* Are Not Functionally Equivalent. J. Bacteriol. 188, 599-608.

Kennedy, G. G., 2003. Tomato, pests, parasitoids, and preda-tors: tritrophic interactions involving the genus *Lycopersicon*. Annu. Rev. Entomol. 48, 51-72.

Kornberg, A., Ochoa, S., Mehler, A. H., 1948. Spectropho-tometric studies on the decarboxylation of β-keto acids. J. Biol. Chem. 174, 159.

Kim, E.-J., Son, H. F., Kim, S., Ahn, J.-W., Kim, K.-J., 2014. Crystal structure and biochemical characterization of beta-keto thiolase B from polyhydroxyalkanoate-producing bacterium *Ralstonia eutropha* H16. Biochem. Biophys. Res. Commun. 444, 365-369.

Lan, E. I., Dekishima, Y., Chuang, D. S., Liao, J. C., 2013. Metabolic engineering of 2-pentanone synthesis in *Escherichia coli*. AIChE J. 59, 3167-3175.

Lennen, R. M., Braden, D. J., West, R. M., Dumesic, J. A., Pfleger, B. F., 2010. A process for microbial hydrocarbon synthesis: Overproduction of fatty acids in *Escherichia coli* and catalytic conversion to alkanes. *Biotechnol. Bioeng.* 106, 193-202.

Lian, J., Zhao, H., 2015. Reversal of the β-Oxidation Cycle in *Saccharomyces cerevisiae* for Production of Fuels and Chemicals. ACS Synth. Biol. 4, 332-341.

Mehrer, C. R., Incha, M. R., Politz, M. C., Pfleger, B. F., 2018. Anaerobic production of medium-chain fatty alcohols via a β-reduction pathway. *Metab. Eng.* 48, 63-71.

Mehrer, C. R., Rand, J. M., Incha, M. R., Cook, T. B., Demir, B., Motagamwala, A. H., Kim, D., Dumesic, J. A., Pfleger, B. F., 2019. Growth-coupled bioconversion of levulinic acid to butanone. *Metab. Eng.* 55, 92-101.

Muller, J., MacEachran, D., Burd, H., Sathitsuksanoh, N., Bi, C., Yeh, Y.-C., Lee, T. S., Hillson, N. J., Chhabra, S. R., Singer, S. W., Beller, H. R., 2013. Engineering of *Ralstonia eutropha* H16 for Autotrophic and Heterotrophic Production of Methyl Ketones. *Appl. Environ. Microbiol.* 79, 4433-4439.

Nie, L., Ren, Y., Schulz, H., 2008. Identification and Characterization of *Escherichia coli* Thioesterase III That Functions in Fatty Acid β-Oxidation. Biochemistry 47, 7744-7751.

Park, J., Rodriguez-Moya, M., Li, M., Pichersky, E., San, K.-Y., Gonzalez, R., 2012. Synthesis of methyl ketones by metabolically engineered *Escherichia coli*. J. Ind. Microbiol. Biotechnol. 39, 1703-1712.

Srirangan, K., Liu, X., Akawi, L., Bruder, M., Moo-Young, M., Chou, C. P., 2016. Engineering *Escherichia coli* for Microbial Production of Butanone. *Appl. Environ. Microbiol.* 82, 2574-2584.

Voelker, T. A., Davies, H. M., 1994. Alteration of the specificity and regulation of fatty acid synthesis of *Escherichia coli* by expression of a plant medium-chain acyl-acyl carrier protein thioesterase. J. Bacteriol. 176, 7320-7327.

Wang, F., Langley, R., Gulten, G., Wang, L., Sacchettini, J. C. 2007. Identification of a type III thioesterase reveals the function of an operon crucial for Mtb virulence. Chem. Biol. 14, 543-551

Yan, Q., Pfleger, B. F., 2019. Revisiting metabolic engineering strategies for microbial synthesis of oleochemicals. *Metab. Eng.*

Youngquist, J. T., Schumacher, M. H., Rose, J. P., Raines, T. C., Politz, M. C., Copeland, M. F., Pfleger, B. F., 2013. Production of medium chain length fatty alcohols from glucose in *Escherichia coli. Metab. Eng.* 20, 177-186.

Yu, G., Nguyen, T. T. H., Guo, Y., Schauvinhold, I., Auldridge, M. E., Bhuiyan, N., Ben-Israel, I., Iijima, Y., Fridman, E., Noel, J. P., Pichersky, E., 2010. Enzymatic Functions of Wild Tomato Methyl ketone Synthases 1 and 2. Plant Physiol. 154, 67-77.

Yuzawa, S., Deng, K., Wang, G., Baidoo, E. E. K., Northen, T. R., Adams, P. D., Katz, L., Keasling, J. D., 2017. Comprehensive in Vitro Analysis of Acyltransferase Domain Exchanges in Modular Polyketide Synthases and Its Application for Short-Chain Ketone Production. ACS Synth. Biol. 6, 139-147.

Yuzawa, S., Mirsiaghi, M., Jocic, R., Fujii, T., Masson, F., Benites, V. T., Baidoo, E. E. K., Sundstrom, E., Tanjore, D., Pray, T. R., George, A., Davis, R. W., Gladden, J. M., Simmons, B. A., Katz, L., Keasling, J. D., 2018. Short-chain ketone production by engineered polyketide synthases in *Streptomyces albus*. Nat. Commun. 9, 4569.

Zhu, M., Xu, X., Li, Y., Wang, P., Niu, S., Zhang, K., Huang, X., 2019. Biosynthesis of the Nematode Attractant 2-Heptanone and Its Co-evolution Between the Pathogenic Bacterium *Bacillus nematocida* and Non-pathogenic Bacterium *Bacillus subtilis*. Front. Microbiol. 10.

Zhu, J., Dhammi, A., van Kretschmar, J. B., Vargo, E. L., Apperson, C. S., Michael Roe, R., 2018. Novel use of aliphatic n-methyl ketones as a fumigant and alternative to methyl bromide for insect control. Pest Manag. Sci. 74, 648-657.

Zhu, Z., Zhou, Y. J., Krivoruchko, A., Grininger, M., Zhao, Z. K., Nielsen, J., 2017. Expanding the product portfolio of fungal type I fatty acid synthases. Nat. Chem. Biol. 13, 360-362.

---

What is claimed is:

1. A recombinant cell for producing methyl ketones comprising:
   a recombinant β-ketoacyl-CoA thioesterase gene;
   a recombinant acyl-ACP thioesterase gene;
   a recombinant acyl-CoA synthetase gene;
   a recombinant 3-ketoacyl-CoA thiolase gene; and
   a functional deletion of at least one of a native enoyl-CoA hydratase gene and a native 3-hydroxyacyl-CoA dehydrogenase gene.

2. The recombinant cell of claim 1, further comprising a functional deletion of a native fadR gene or a homolog thereof.

3. The recombinant cell of claim 1, further comprising a functional deletion of a native acyl-CoA dehydrogenase gene.

4. The recombinant cell of claim 1, wherein the recombinant cell exhibits enhanced production of methyl ketone with respect to a corresponding native cell.

5. The recombinant cell of claim 4, wherein the methyl ketone comprises medium-chain methyl ketone.

6. The recombinant cell of claim 5, wherein the medium-chain methyl ketone comprises at least one of 2-heptanone, 2-nonanone, and 2-undecanone.

7. A recombinant cell for producing methyl ketones comprising:
   a recombinant β-ketoacyl-CoA thioesterase gene, wherein the recombinant β-ketoacyl-CoA thioesterase gene encodes a protein comprising an amino acid sequence with at least 95% sequence identity to SEQ ID NO:8;
   a recombinant acyl-ACP thioesterase gene, wherein the recombinant acyl-ACP thioesterase gene encodes a protein comprising an amino acid sequence with at least 95% sequence identity to SEQ ID NO:2;
   a recombinant acyl-CoA synthetase gene, wherein the recombinant acyl-CoA synthetase gene encodes a protein comprising an amino acid sequence with at least 95% sequence identity to SEQ ID NO:12;
   a functional deletion of a native acyl-CoA dehydrogenase gene;
   a functional deletion of at least one of a native enoyl-CoA hydratase gene and a native 3-hydroxyacyl-CoA dehydrogenase gene; and at least one of:
   a functional deletion of a native fadR gene or a homolog thereof; and
   a recombinant 3-ketoacyl-CoA thiolase gene that encodes a protein comprising an amino acid sequence with at least 95% sequence identity to SEQ ID NO: 22 or SEQ ID NO:242,
wherein the recombinant cell exhibits enhanced production of 2-nonanone with respect to a corresponding native cell.

8. The recombinant cell of claim 1, wherein the recombinant cell is a bacterium.

9. The recombinant cell of claim 1, wherein the recombinant cell is an E coli.

10. A recombinant cell for producing methyl ketones comprising:
   a recombinant β-ketoacyl-CoA thioesterase gene, wherein the recombinant β-ketoacyl-CoA thioesterase gene encodes a protein comprising an amino acid sequence with at least 95% sequence identity to SEQ ID NO:8;
   a recombinant acyl-ACP thioesterase gene, wherein the acyl-ACP thioesterase gene encodes a protein comprising an amino acid sequence with at least 95% sequence identity to SEQ ID NO: 2;
   a recombinant acyl-CoA synthetase gene, wherein the recombinant acyl-CoA synthetase gene encodes a protein comprising an amino acid sequence with at least 95% sequence identity to SEQ ID NO:12;
   a functional deletion of a native acyl-CoA dehydrogenase gene;
   a recombinant acyl-CoA dehydrogenase gene that encodes a protein comprising an amino acid sequence with at least 95% sequence identity to SEQ ID NO:30;
   a functional deletion of a native 3-ketoacyl-CoA thiolase gene; and
   at least one of:
      a functional deletion of a native fadR gene or a homolog thereof;
      a recombinant enoyl-CoA hydratase gene; and
      a recombinant 3-hydroxyacyl-CoA dehydrogenase gene,
wherein the recombinant cell exhibits enhanced production of 2-heptanone with respect to a corresponding native cell.

11. A recombinant cell for producing methyl ketones comprising:

a recombinant β-ketoacyl-CoA thioesterase gene, wherein the recombinant β-ketoacyl-CoA thioesterase gene encodes a protein comprising an amino acid sequence with at least 95% sequence identity to SEQ ID NO:8;

a recombinant acyl-ACP thioesterase gene, wherein the acyl-ACP thioesterase gene encodes a protein comprising an amino acid sequence with at least 95% sequence identity to SEQ ID NO: 4;

a recombinant acyl-CoA synthetase gene, wherein the recombinant acyl-CoA synthetase gene encodes a protein comprising an amino acid sequence with at least 95% sequence identity to SEQ ID NO:10;

a functional deletion of a native acyl-CoA dehydrogenase gene;

a recombinant acyl-CoA dehydrogenase gene that encodes a protein comprising an amino acid sequence with at least 95% sequence identity to SEQ ID NO:30;

a functional deletion of a native 3-ketoacyl-CoA thiolase gene; and at least one of:

a functional deletion of a native fadR gene or a homolog thereof;

a recombinant enoyl-CoA hydratase gene encoding a protein comprising an amino acid sequence with at least 95% sequence identity to SEQ ID NO:16; and a recombinant 3-hydroxyacyl-CoA dehydrogenase gene encoding a protein comprising an amino acid sequence with at least 95% sequence identity to SEQ ID NO: 16, wherein the recombinant cell exhibits enhanced production of 2-undecanone with respect to a corresponding native cell.

* * * * *